United States Patent [19]

Takiguchi et al.

[11] Patent Number: 4,985,361
[45] Date of Patent: Jan. 15, 1991

[54] HUMAN PANCREATIC ELASTASE

[75] Inventors: Yo Takiguchi; Tokio Tani; Ichiro Kawashima; Jun Ohsumi; Hidehiko Furukawa; Toshinori Ohmine, all of Tokyo, Japan

[73] Assignee: Sankyo Company, Limited, Tokyo, Japan

[21] Appl. No.: 111,094

[22] Filed: Oct. 13, 1987

Related U.S. Application Data

[63] Continuation-in-part of Ser. No. 846,934, Apr. 1, 1986, abandoned.

[30] Foreign Application Priority Data

Apr. 5, 1985 [JP] Japan ................................ 60-72308
Apr. 27, 1985 [JP] Japan ................................ 60-91986
Jul. 26, 1985 [JP] Japan ................................ 60-163964
Oct. 23, 1985 [JP] Japan ................................ 60-236686

[51] Int. Cl.$^5$ .................... C12N 9/66; C12P 21/06; C12P 21/02; C12P 21/04

[52] U.S. Cl. .................. 435/218; 435/69.1; 435/69.8; 435/70.1; 435/70.3; 435/71.2; 435/91; 435/172.3; 435/252.31; 435/252.33; 435/320; 435/240.2; 536/27; 530/350; 935/18; 935/29; 935/32; 935/41; 935/48; 935/56; 935/58; 935/61

[58] Field of Search .................. 435/68, 70, 91, 218, 435/171.1, 171.2, 320, 252.1, 252.3, 256, 69.1, 69.8, 70.1, 70.3, 71.2, 252.33, 252.31, 240.2; 536/27; 530/350; 935/18, 28, 29, 41, 47, 48, 56, 58, 60, 69, 70, 73, 74, 82

[56] References Cited

PUBLICATIONS

Sziegoleit, A. et al., Eur. J. Biochem. 151: 595-599 (1985).
Largman, C. et al., Biochemistry, vol. 15, pp. 2491-2500 (1976).
Largman, C., Biochemistry, vol. 22, pp. 3763-3770 (1983).
MacDonald, R. J. et al., Biochemistry, vol. 21, pp. 1453-1463 (1982).

Primary Examiner—Robin L. Teskin
Assistant Examiner—Joan Ellis
Attorney, Agent, or Firm—Frishauf, Holtz, Goodman & Woodward

[57] ABSTRACT

Human pancreatic elastase can now be obtained from a genetically engineered source.

4 Claims, 19 Drawing Sheets

Fig. 9.

```
                    Signal peptidase recognition site
   HpaII                          ↓                            HhaI
5' [ CG  GCG  GCT  GCG  TGT  GGG  GTC  TCC  ACT  TAC  GCG ] 3'
   3' [ CGC  CGA  CGC  ACA  CCC  CAG  AGG  TGA  ATG  C ] 5'

Ala  Ala  Ala  Cys  Gly  Val  Ser  Thr  Tyr  Ala
```

Fig.13.

```
                                    Recognition site of the signal peptidase
  HpaII                                         ↓
   5' CG  GCG  GCT  GCG  AGT  GCT  GTT  GCT  CAT  GGT
   3'  CGC  CGA  CGC  TCA  CGA  CAA  CAG  GTA  CCA
         Ala  Ala  Ala  Ser  Ala  Val  Val  His  Gly GAG  GAT  GCG  GTC  CCC  TAC  AGC  TGG  CCC  TGG
      CTC  CTA  CGC  CAG  GGG  ATG  TCG  ACC  GGG  ACC
      Glu  Asp  Ala  Val  Pro  Tyr  Ser  Trp  Pro  Trp
                                                              HindIII
      CAG  GTT  TCC  CTG  CAG  TAT  GAG  AAA  AGT  GGA 3'
      GTC  CAA  AGG  GAC  GTC  ATA  CTC  TTT  TCA  CCT  TCG  A  5'
      Gln  Val  Ser  Leu  Gln  Tyr  Glu  Lys  Ser  Gly
```

Fig. 18.

```
                             Recognition site of the signal peptidase
                                                 ↓
       Pro  Ala  Ala  Ala  Val  Val  Asn  Gly  Glu  Asp
  5'  CG   GCG  GCT  GCG  GTT  GTC  AAT  GGT  GAG  GAT
  3'  CGC  CGA  CGC  CAA  CAG  TTA  CCA  CTC  CTA
      ↑
Recognition site of HpaII Ala  Val  Pro  Tyr  Ser  Trp  Pro  Trp  Gln  Val
   GCG  GTC  CCC  TAC  AGC  TGG  CCC  TGG  CAG  GTT
   CGC  CAG  GGG  ATG  TCG  ACC  GGG  ACC  GTC  CAA Ser  Leu  Gln  Tyr  Glu  Lys  Ser  Gly  Ser
   TCC  CTG  CAG  TAT  GAG  AAA  AGC  GGA  -3'
   AGG  GAC  GTC  ATA  CTC  TTT  TCG  CCT  TCG  A-5'
                                                 ↑
                                    Recognition site of HindIII
```

HUMAN PANCREATIC ELASTASE

BACKGROUND OF THE INVENTION

This case is a continuation-in-part of U.S. Ser. No. 06/846,934, now abandoned.

This invention relates to human pancreatic elastase.

Elastase is a serine protease, capable of hydrolyzing the fibrous insoluble protein known as elastin. Elastin is a scleroprotein forming connective tissues. tendons, aortic integuments and cervical bundles of higher animals. Elastin is only slightly degraded by pepsin and trypsin.

In the course of their study on arteriosclerbsis, Balo' et al observed degradation of the elastin fibers of blood vessel walls and postulated the presence of a degrading enzyme [Balo', J and Banga, I: Schweiz Z Patho Bacteriol. 12, 350 (1949)]. Subsequently, Banga discovered an enzyme in the pancreas which specifically degrades elastin. The enzyme was isolated in the form of crystals and names "elastase" [Banga, I: Acta Physiol Acad Sci Hung, 3, 317 (1952)].

Elastase has been confirmed to exist in the pancreas of most animals, including humans, monkeys, cats, rabbits, etc. The level is about 3.1 mg/g-pancreas in human beings, about 2.2 mg/g in bovine animals and about 10.2 mg/g in rats. A correlation is recognized between elastase activity and the age of a human being: a marked lowering in elastase activity is observed in the pancreas and plasma of males over 40 and females over 60 years [Loeven, W A and Baldwin, Maureen M: Gerontologia, 17, 170 (1971)].

In the case of patients with arteriosclerosis, the elastase activity in the pancreas was found to be markedly lower than that of healthy people, and in some cases it had completely disappeared [Balo', J, and Banga, I: Nature, 178, 310 (1956)]. Subsequent studies have also demonstrated that elastase not only degrades elastin but also promotes elasrin biosynthesis.

Studies on the pharmacological action of elastase have been carried out in rats and rabbits, and have revealed the following effects:

(1) inhibition of the deposition of lipids and calcium on arterial walls;
(2) elimination of cholesterol and calcium from arterial walls;
(3) selective degradation of denatured elastin;
(4) promotion of synthesis of elastin fibers in the
(5) lowering of serum lipids;
(6) improvement of lipoprotein metabolism.

In clinical studies conducted on the basis of the studies mentioned above, the following effects have become apparent after oral administration of elastase:

(1) restoration of elasticity and expandability of arterial walls;
(2) improvement of serum lipid abnormality;
(3) improvement of serum lipoprotein metabolism.

Elastase extracted and purified from porcine pancreas was used for the above studies. However, with administration of porcine elastase to human beings, there is the risk of antibody formation due to the foreign protein, and the danger of anaphylaxis with repeated administration (Japanese patent Application Laid-open No. 11180/1984). Accordingly, human elastase is preferable for human use. However lt has been extremely difficult to procure human elastase in sufficient quantities from traditional sources.

At present, two kinds of human pancreatic elastase are known, elastase I and elastase II. They have not been fully characterized. For example, for pancreatic elastase II, a partial sequence of 16 amino acid residues representing 12 amino acid residues in the activation peptide and 4 amino acid residues at the N-terminal end of the elastase have been sequenced [Largman. C et al; Biochim Biophys Acta, 623, 208 (1980)]. This partial sequence is Cys Gly Asp Pro Thr Tyr Pro Pro Tyr Val Thr Arg Val Val Gly Gly.

OBJECTS OF THE PRESENT INVENTION

It is an object of this invention to make human pancreatic elastase more readily available, with the possibility of obtaining the elastase in substantially pure form. It is a further object of this invention to eliminate the continuing dependency on human pancreas for adequate supplies of human pancreatic elastase. It is a yet further object to produce new elastase compounds and elastase-like compounds.

SUMMARY FO THE INVENTION

This invention embraces the use of genetic engineering for the production of human pancreatic elastase. Recombinant DNA technology is employed, in order to provide a base sequence coding for a human pancreatic elastase or a functionally similar compound. Correspondingly, human pancreatic elastase and functionally similar compounds now become readily available for the first time. Indeed, novel elastases have been discovered and are part of this invention. Thus, through the use of genetic engineering, it is now possible in accordance with the present invention to provide a DNA which codes for a compound capable of functioning as a human pancreatic elastase. Novel human pancreatic elastases are provided, as well as derivative compounds which function as human pancreatic elastases. Such compounds, which include compounds arising from silent mutations, fusion proteins and other compounds functionally effective as a human pancreatic elastase, are included. Thus, any substantially similar protein effective as, a human pancreatic elastase, including compounds corresponding to human pancreatic elastases with one or more deleted, replaced or altered amino acids, and compounds corresponding to human pancreatic elastases with one or more extra amino acids, are also included. More especially, precursor compounds such as proelastases and preproelastases, especially when expressed by a recombinant DNA sequence, as well as elastases obtained by activation of such precursor compounds, are part of this invention. Further examples of precursor compounds within this invention include fusion proteins comprising an elastase (optionally in the form of a proelastase or preproelastase) and an amino acid sequence derived from another protein. In particular, such fusion proteins can be obtained when the DNA coding for an elastase is inserted into an expression gene downstream of a promoter.

PREFERRED EMBODIMENTS OF THIS INVENTION

In particular, the present invention provides new human pancreatic elastases which include forms of elastase which herein are termed elastase IIA, IIB, IIIA and IIIB.

For convenience, the preferred aspects of the present invention are considered in four aspects, corresponding to the human pancreatic elastases IIA, IIB, IIIA and IIIB. In considering the following amino acid sequences for these elastases, it is to be borne in mind that the present invention embraces any substantially similar protein effective as a human pancreatic elastase, including compounds with one or more deleted, replaced, altered or extra amino acids.

Elastase IIA

The present invention provides human pancreatic elastase IIA having the following amino acid sequence of formula (I):

(N)-Cys Gly Asp Pro Thr Tyr Pro Pro Tyr Val
Thr Arg Val Val Gly Gly Glu Glu Ala Arg
Pro Asn Ser Trp Pro Trp Gln Val Ser Leu
Gln Tyr Ser Ser Asn Gly Lys Trp Tyr His
Thr Cys Gly Gly Ser Leu Ile Ala Asn Ser
Trp Val Leu Thr Ala Ala His Cys Ile Ser
Ser Ser Arg Thr Tyr Arg Val Gly Leu Gly
Arg His Asn Leu Tyr Val Ala Glu Ser Gly
Ser Leu Ala Val Ser Val Ser Lys Ile Val
Val His Lys Asp Trp Asn Ser Asn Gln Ile
Ser Lys Gly Asn Asp Ile Ala Leu Leu Lys
Leu Ala Asn Pro Val Ser Leu Thr Asp Lys
Ile Gln Leu Ala Cys Leu Pro Pro Ala Gly
Thr Ile Leu Pro Asn Asn Tyr Pro Cys Tyr
Val Thr Gly Trp Gly Arg Leu Gln Thr Asn
Gly Ala Val Pro Asp Val Leu Gln Gln Gly
Arg Leu Leu Val Val Asp Tyr Ala Thr Cys
Ser Ser Ser Ala Trp Trp Gly Ser Ser Val
Lys Thr Ser Met Ile Cys Ala Gly Gly Asp
Gly Val Ile Ser Ser Cys Asn Gly Asp Ser
Gly Gly Pro Leu Asn Cys Gln Ala Ser Asp
Gly Arg Trp Gln Val His Gly Ile Val Ser
Phe Gly Ser Arg Leu Gly Cys Asn Tyr Tyr
His Lys Pro Ser Val Phe Thr Arg Val Ser
Asn Tyr Ile Asp Trp Ile Asn Ser Val Ile
Ala Asn Asn -(C)

For the human pancreatic elastase IIA itself, the N-terminal end simply terminates with a hydrogen atom. For derivatives of human pancreatic elastase IIA, the protein can be preceded with an amino acid sequence such as Met or all or part of (N) Met Ile Arg Thr Leu Leu Leu Ser Thr Leu Val Ala Gly Ala Leu Ser (C).

The invention also provides a DNA coding for human pancreatic elastase IIA. Such a DNA can have a base sequence represented by the following formula (II):

(5')-TGT GGG GAC CCC ACT TAC CCA CCT TAT GTG
ACT AGG GTG GTT GGC GGT GAA GAA GCG AGG
CCC AAC AGC TGG CCC TGG CAG GTC TCC CTG
CAG TAC AGC TCC AAT GGC AAG TGG TAC CAC
ACC TGC GGA GGG TCC CTG ATA GCC AAC AGC
TGG GTC CTG ACG GCT GCC CAC TGC ATC AGC
TCC TCC AGG ACC TAC CGC CGC GGG CTG GGC
CCG CAC AAC CTC TAC GTT GCG GAG TCC GGC
TCG CTG GCA GTC AGT GTC TCT AAG ATT GTG
GTG CAC AAG GAC TGG AAC TCC AAC CAA ATC
TCC AAA GGG AAC GAC ATT GCC CTG CTC AAA
CTG GCT AAC CCC GTC TCC CTC ACC GAC AAG
ATC CAG CTG GCC TGC CTC CCT CCT GCC GGC
ACC ATT CTA CCC AAC AAC TAC CCC TGC TAC
GTC ACG GGC TGG GGA AGG CTG CAG ACC AAC
GGG GCT CTC CCT GAT GAT CTG CAG CAG GGC
CGG TTG CTG GTT GTG GAC TAT GCC ACC TGC
TCC AGC TCT GCC TGG TGG GGC AGC AGT GTG
AAA ACC AGT ATG ATC TGT GCT GGG GGT GAT
GGC GTG ATC TCC AGC TGC AAC GGA GAC TCT
GGT GGG CCA CTG AAC TGT CAG GCG TCT GAC
GGC CGG TGG CAG GTG CAC GGC ATC GTC AGC
TTC GGG TCT CGC CTC GGC GGC AAC TAC TAC
CAC AAG CCC TCC GTC TTC ACG CGG GTC TCC
ATT TAC ATC GAC TGG ATC AAT TCG GTG ATT

GCA AAT ACC - X (3')

wherein X represents a stop codon, that is TAA, TGA or TAG. It is to be recognized that the amino acid sequence of formula (I) can arise from a different DNA base sequence to that of formula (II), and such a modified DNA sequence is also part of this invention.

The DNA of this invention may optionally have ATG at its 5'-end, which will then code for an additional Met at the N-terminal end of the amino acid sequence. As another option, the DNA may have at its 5'-end a part or all of the sequence (5=) - ATG ATA AGG ACG CTG CTG CTG TCC ACT TTG GTG GCT GGA GCC CTC AGT - (3'), which will then code for an extra sequence at the N-terminal end of the amino acid sequence comprising a part or all of (N) Met Ile Arg Thr Leu Leu Leu Ser Thr Leu Val Ala Gly Ala Leu Ser (C).

Elastase IIB

This invention further provides human pancreatic elastase IIB having the following amino acid sequence of formula (III):

(N)-Cys Gly Val Ser Thr Tyr Ala Pro Asp Met
Ser Arg Met Leu Gly Gly Glu Glu Ala Arg
Pro Asn Ser Trp pro Trp Gln Val Ser Leu
Gln Tyr Ser Ser Asn Gly Gln Trp Tyr His
Thr Cys Gly Gly Ser Leu Ile Ala Asn Ser
Trp Val Leu Thr Ala Ala His Cys Ile Ser
Ser Ser Arg Ile Tyr Arg Val Met Leu Gly
Gln His Asn Leu Tyr Val Ala Glu Ser Gly
Ser Leu Ala Val Ser Val Ser Lys Ile Val
Val His Lys Asp Trp Asn Ser Asn Gln Val
Ser Lys Gly Asn Asp Ile Ala Leu Leu Lys
Leu Ala Asn Pro Val Ser Leu Thr Asp Lys
Ile Gln Leu Ala Cys Leu Pro Pro Ala Gly
Thr Ile Leu Pro Asn Asn Tyr Pro Cys Tyr
Val Thr Gly Trp Gly Arg Leu Gln Thr Asn
Gly Ala Leu Pro Asp Asp Leu Lys Gln Gly
Arg Leu Leu Val Val Asp Tyr Ala Thr Cys
Ser Ser Ser Gly Trp Trp Gly Ser Thr Val
Lys Thr Asn Met Ile Cys Ala Gly Gly Asp
Gly Val Ile Cys Thr Cys Asn Gly Asp Ser
Gly Gly Pro Leu Asn Cys Gln Ala Ser Asp
Gly Arg Trp Glu Val His Gly Ile Gly Ser
Leu Thr Ser Val Leu Gly Cys Asn Tyr Tyr
Tyr Lys Pro Ser Ile Phe Thr Arg Val Ser
Asn Tyr Asn Asp Trp Ile Asn Ser Val Ile
Ala Asn Asn-(C)

For the human pancreatic elastase IIB itself, the N-terminal end simply terminates with a hydrogen atom. For derivatives of human pancreatic elastase IIB, the protein can be extended with an amino acid sequence such as Met or all or part of (N) Met Ile Arg Thr Leu Leu Leu Ser Thr Leu Val Ala Gly Ala Leu Ser (C).

The invention also provides a DNA coding for human pancreatic elastase IIB. Such a DNA can have a base sequence represented by the following formula (IV):

(5')-TGT GGG GTC TCC ACT TAC GCG CCT GAT ATG
TCT AGG ATG CTT GGA GGT GAA GAA GCG AGG
CCC AAC AGC TGG CCC TGG CAG GTC TCC CTG
CAG TAC AGC TCC AAT GGC CAG TGG TAC CAC
ACC TGC GGA GGG TCC CTG ATA GCC AAC AGC
TGG GTC CTG ACG GCT GCC CAC TGC ATC AGC
TCC TCC AGG ATC TAC CGC GTG ATG CTG GGC
CAG CAT AAC CTC TAC GTT GCA GAG TCC GGC
TCG CTG GCC GTC AGT GTC TCT AAG ATT GTG

-continued

```
GTG CAC AAG GAC TGG AAC TCC AAC CAG GTC
TCC AAA GGG AAC GAC ATT GCC CTG CTC AAA
CTG GCT AAC CCC GTC TCC CTC ACC GAC AAG
ATC CAG CTG GCC TGC CTC CCT CCT GCC GGC
ACC ATT CTA CCC AAC AAC TAC CCC TGC TAC
GTC ACA GGC TGG GGA AGG CTG CAG ACC AAC
GGG GCT CTC CCT GAT GAC CTG AAG CAG GAC
CGG TTG CTG GTT GTG GAC TAT GCC ACC TGC
TCC AGC TCT GGC TGG TGG GGC AGC ACC GTG
AAG ACG AAT ATG ATC TGT GCT GGG GGT GAT
GGC GTG ATA TGC ACC TGC AAC GGA GAC TCC
GGT GGG CCG CTG AAC TGT CAG GCA TCT GAC
GGC CGG TGG GAG GTG CAT GGC ATC GGC AGC
CTC ACG TCG GTC CTT GGT TGC AAC TAC TAC
TAC AAG CCC TCC ATC TTC ACG CGG GTC TCC
AAC TAC AAC GAC TGG ATC AAT TCG GTG ATT
GCA AAT AAC - X (3')
``` wherein X represents a stop codon, that is TAA, TGA or TAG. It is to be recognized that the amino acid sequence of formula (III) can arise from a different DNA base sequence to that of formula (IV), and such a modified DNA sequence is also part of this invention.

The DNA may optionally have ATG at its 5'-end, which will then code for an additional Met at the N-terminal end of the amino acid sequence. As another option, the DNA may have at its 5'-end a part or all of the sequence (5') - ATG ATT AGG ACC CTG CTG CTG TCC ACT TTG GTG GCT GGA GCC CTC AG - (3'), which will then code for an extra sequence at the N-terminal end of the amino acid sequence comprising a part or all of (N) Met Ile Arg Thr Leu Leu Leu Ser Thr Leu Val Ala Gly Ala Leu Ser (C).

Both the type IIA and the type IIB human pancreatic elastases of this invention may exist in a two-chain configuration formed by a disulfide-bond between Cys at position 1 and an inner Cys in the molecule when the bond is broken between amino acid 12 and amino acid 13. The present invention includes these two-chain elastases.

Elastase III

This invention provides human pancreatic elastase IIIA having the following amino acid sequence of formula (V):

```
(N)-Val Val His Gly Glu Asp Ala Val Pro Tyr
    Ser Trp Pro Trp Gln Val Ser Leu Gln Tyr
    Glu Lys Ser Gly Ser phe Tyr His Thr Cys
    Gly Gly Ser Leu Ile Ala Pro Asp Trp Val
    Val Thr Ala Gly His Cys Ile Ser Arg Asp
    Leu Thr Tyr Gln Val Val Leu Gly Glu Tyr
    Asn Leu Ala Val Lys Glu Gly Pro Glu Gln
    Val Ile Pro Ile Asn Ser Glu Glu Leu Phe
    Val His Pro Leu Trp Asn Arg Ser Cys Val
    Ala Cys Gly Asn Asp Ile Ala Leu Ile Lys
    Leu Ser Arg Ser Ala Gln Leu Gly Asp Ala
    Val Gln Leu Ala Ser Leu Pro Pro Ala Gly
    Asp Ile Leu Pro Asn Lys Thr Pro Cys Tyr
    Ile Thr Gly Trp Gly Arg Leu Tyr Thr Asn
    Gly Pro Leu Pro Asp Lys Leu Gln Gln Ala
    Arg Leu Pro Val Val Asp Tyr Lys His Cys
    Ser Arg Trp Asn Trp Trp Gly Ser Thr Val
    Lys Lys Thr Met Val Cys Ala Gly Gly Tyr
    Ile Arg Ser Gly Cys Asn Gly Asp Ser Gly
    Gly Pro Leu Asn Cys Pro Thr Glu Asp Gly
    Gly Trp Gln Val His Gly Val Thr Ser Phe
    Val Ser Ala Phe Gly Cys Asn Phe Ile Trp
    Lys Pro Thr Val Phe Thr Arg Val Ser Ala
    Phe Ile Asp Trp Ile Glu Glu Thr Ile Ala
    Ser His-(C)
```

For the human pancreatic elastase IIIA itself, the N-terminal end simply terminates with a hydrogen atom. For derivatives of human pancreatic elastase IIIA, the protein can be preceded with an amino acid sequence such as Met or a part of all of (N) Met Met Leu Arg Leu Leu Ser Ser Leu Leu Leu Val Ala Val Ala Ser Gly Tyr Gly Pro Pro Ser Ser His Ser Ser Ser Arg (C).

This invention also provides a DNA coding for human pancreatic elastase IIIA. Such a DNA can have a base sequence represented by the following formula (VI):

```
(5')-GTT GTC CAT GGT GAG GAT GCG GTC CCC TAC
     AGC TGG CCC TGG CAG ,GTT TCC CTG CAG TAT
     GAG AAA AGT GGA AGC TTC TAC CAC ACG TGT
     GGC GGT AGC CTC ATC GCC CCC GAT TGG GTT
     GTG ACT GCC GGC CAC TGC ATC TCG AGG GAT
     CTG ACC TAC CAG GTG GTG TTG GGT GAG TAC
     AAC CTT GCT GTG AAG GAG GGC CCC GAG CAG
     GTG ATC CCC ATC AAC TCT GAG GAG CTG TTT
     GTG CAT CCA CTC TGG AAC CGC TCG TGT GTG
     GCC TGT GGC AAT GAC ATC GCC CTC ATC AAG
     CTC TCA CGC AGC GCC CAG CTG GGA GAT GCC
     GTC CAG CTC CTC TCA CTC CCT CCC GCT GGT
     GAC ATC CTT CCC AAC AAG ACA CCC TGC TAC
     ATC ACC GGC TGG GGC CGT CTC TAT ACC AAT
     GGG CCA CTC CCA GAC AAG CTG CAG CAG GC
     CGG CTG CCC GTG GTG GAC TAT AAG CAC TGC
     TCC AGG TGG AAC TGG TGG GGT TCC ACC GTG
     AAG AAA ACC ATG GTG TGT GCT GGA GGG TAC
     ATC CGC TCC GGC TGC AAC GGT GAC TCT GGA
     GGA CCC CTC AAC TGC CCC ACA GAG GAT GGT
     GGC TGG CAG GTC CAC GGT GTG ACC AGC TTT
     GTT TCT GCC TTT GGC TGC AAC TTC ATC TGG
     AAG CCC ACG GTG TTC ACT CGA GTC TCC GCC
     TTC ATC GAC TGG ATT GAG GAG ACC ATA GCA
     AGC CAC - X (3')
``` wherein X represents a stop codon, that is TAA, TGA or TAG. It is to be recognized that the amino acid sequence of formula (V) can arise from a different DNA base sequence to the one of formula (VI), and such a modified DNA sequence is also part of this invention.

The DNA may optionally have ATG at its 5'-end, which will then code for an additional Met at the N-terminal end of the amino acid sequence. As another option, the DNA may optionally have at its 5'-end a part or all of the sequence (5') - ATG ATG CTC CGG CTG CTC AGT TCC CTC CTC CTT GTG GCC GTT GCC TCA GGC TAT GGC CCA CCT TCC TCT CAC TCT TCC AGC CGC - (3'). which will then code for an extra sequence at the N-terminal end of the amino acid sequence comprising a part or all of (N) Met Met Leu Arg Leu Leu Ser Ser Leu Leu Leu Val Ala Val Ala Ser Gly Tyr Gly Pro Pro Ser Ser His Ser Ser Ser Arg (C).

Elastase IIIB

This invention provides human pancreatic elastase IIIB having the following amino acid sequence of formula (VII):

```
(N)-Val Val Asn Gly Glu Asp Ala Val Pro Tyr
    Ser Trp Pro Trp Gln Val Ser Leu Gln Tyr
    Glu Lys Ser Gly Ser Phe Tyr His Thr Cys
    Gly Gly Ser Leu Ile Ala Pro Asp Trp Val
    Val Thr Ala Gly His Cys Ile Ser Ser Ser
    Arg Thr Tyr Gln Val Val Leu Gly Glu Tyr
    Asp Arg Ala Val Lys Glu Gly Pro Glu Gln
    Val Ile Pro Ile Asn Ser Gly Asp Leu Phe
    Val His Pro Leu Trp Asn Arg Ser Cys Val
```

-continued

```
Ala Cys Gly Asn Asp Ile Ala Leu Ile Lys
Leu Ser Arg Ser Ala Gln Leu Gly Asp Ala
Val Gln Leu Ala Ser Leu Pro Pro Ala Gly
Asp Ile Leu Pro Asn Glu Thr Pro Cys Tyr
Ile Thr Gly Trp Gly Arg Leu Tyr Thr Asn
Gly Pro Leu Pro Asp Lys Leu Gln Glu Ala
Leu Leu Pro Val Val Asp Tyr Glu His Cys
Ser Arg Trp Asn Trp Trp Gly Ser Ser Val
Lys Lys Thr Met Val Cys Ala Gly Gly Asp
Ile Arg Ser Gly Cys Asn Gly Asp Ser Gly
Gly Pro Leu Asn Cys Pro Thr Glu Asp Gly
Gly Trp Gln Val His Gly Val Thr Ser Phe
Val Ser Ala Phe Gly Cys Asn Thr Arg Arg
Lys Pro Thr Val Phe Thr Arg Val Ser Ala
Phe Ile Asp Trp Ile Glu Glu Thr Ile Ala
Ser His-(C)
```

For the human pancreatic elastase IIIB itself, the N-terminal end simply terminates with a hydrogen atom. For derivatives of human pancreatic elastase IIIB, the protein can be preceded with an amino acid sequence such as Met or a part or all of (N) Met Met Leu Arg Leu Leu Ser Ser Leu Leu Leu Val Ala Val Ala Ser Gly Tyr Gly Pro Pro Ser Ser Arg Pro Ser Ser Arg (C).

The invention also provides a DNA coding for human pancreatic elastase IIIB. 8uch a DNA can have a base sequence represented by the following formula (VIII):

```
(5')-GTT GTC AAT GGT GAG GAT GCG GTC CCC TAC
    AGC TGG CCC TGG CAG GTT TCC CTG CAG TAT
    GAG AAA AGC GGA AGC TTC TAC CAC ACC TGT
    GGC GGT AGC CTC ATC GCC CCC GAC TGG GTT
    GTG ACT GCC GGC CAC TGC ATC TCG AGC TCC
    CGG ACC TAC CAG GTG GTG TTG GGC GAG TAC
    GAC CGT GCT GTG AAG GAG GGC CCC GAG CAG
    GTG ATC CCC ATC AAC TCT GGG GAC CTC TTT
    GTG CAT CCA CTC TGG AAC CGC TCG TGT GTG
    GCC TGT GGC AAT GAC ATC GCC CTC ATC AAG
    CTC TCA CGC AGC GCC CAG CTG GGA GAC GCC
    GTC CAG CTC GCC TCA CTC CCT CCG GCT GGT
    GAC ATC CTT CCC AAC GAG ACA CCC TGC TAC
    ATC ACC GGC TGG GGC CGT CTC TAT ACC AAC
    GGG CCA CTC CCA GAC AAG CTG CAG GAG GCC
    CTG CTG CCG GTG GTG GAC TAT GAA CAC TGC
    TCC AGG TGG AAC TGG TGG GGT TCC TCC GTG
    AAG AAG ACC ATG GTG TGT GCT GGA GGG GAC
    ATC CGC TCC GGC TGC AAT GGT GAC TCT GGA
    GGA CCC CTC AAC TGC CCC ACA GAG GAT GGT
    GGC TGG CAG GTC CAT GGC GTG ACC AGC TT
    GTT TCT GCC TTT GGC TGC AAC ACC CGC AGG
    AAG CCC ACG GTG TTC ACT CGA GTC TCC GCC
    TTC ATT GAC TGG ATT GAG GAG ACC ATA GCA
    AGC CAC - X (3')
``` wherein X represents a stop codon, that is TAA, TGA or TAG. It is to be recognized that the amino acid sequence of formula (VII) can arise from a different DNA base sequence to the one of formula (VIII), and such a modified DNA sequence is also part of this invention.

The DNA may optionally have ATG at its 5'-end, which will then code for an additional Met at the N-terminal end of the amino acid sequence. As another option, the DNA may have at its 5'-end a part or all of the sequence (5') - ATG ATG CTC CGG CTG CTC AGT TCC CTC CTC CTT GTG GCC GTT GCC TCA GGC TAT GGC CCA CCT TCC TCT CGC CCT TCC AGC CGC - (3'), which will then code for an extra sequence at the N-terminal end of the amino acid sequence comprising a part or all of (N) Met Met Leu Arg Leu Leu Ser Ser Leu Leu Leu Val Ala Val Ala Ser Gly Tyr Gly Pro Pro Ser Ser Arg Pro Ser Ser Arg (C).

PROCESSES OF THIS INVENTION

The DNA of this invention, including the base sequences represented by the formulae (II), (IV), (VI) and (VIII) with optional extensions, can be produced for example in accordance with the steps (a) to (d):
(a) separation of mRNA from human pancreas;
(b) formation from the mRNA of a bank of cDNA in a suitable host;
(c) isolation from the cDNA plasmid bank of plasmids including cDNA coding for human elastase, for example by using cDNA of human elastase I or of rat elastase II as a probe;
(d) isolation of the desired cloned DNA from the plasmid.

From the DNA, the corresponding prorein can then be prepared, for example by the steps of:
(1) inserting the DNA into an expression vector;
(2) transforming a host organism;
(3) culturing the transformed host unde conditions resulting in expression of the DNA sequence; and
(4) isolating a compound including the protein.

Considering the process in some more detail, several methods are available which may be used in the extraction of mRNA from the human pancreas, including for instance the guanidine-thiocyanate-hot-phenol method, the guanidine thiocyanate-ceasium chloride method, or the guanidine-thiocyanate-guanidine hydrochloride method. The last-mentioned method is preferred since it is superior to the other two methods in the following respects: the operation is simpler; recovery of extraction is high; extraction from a relatively large number of organs is possible; no contaminating DNA is entrained and degradation of mRNA is low.

Most of the mRNA existing in the cytoplasm of eukaryotic cells is known to have a poly(A) sequence at the 3'-end. Utilizing this specific feature, mRNA can be purified by adsorbing it onto a column of an oligo(dT) cellulose, and then eluting it.

Using the mRNA obtained as a template, complementary double-stranded DNA can be synthesized with the use of a reverse transcriptase. Several methods can be employed for synthesizing the double stranded DNA, including for example the S1 nuclease method [Efstratiadis, A et al: Cell, 7, 279 (1976)], the Land method [Land, H et al: Nucleic Acids Res, 9, 2251 (1981)], the Okayama-Berg method [Okayama, H and Berg, P: Mol Cell Biol, 2, 161 (1982)], the O Joon Yoo method [O Joon Yoo et al: Proc Natl Acad Sci USA, 79 1049 (1982)], etc. For the present invention, the Okayama-Berg method is preferred.

The double stranded cDNA is thus inserted into a suitable vector. The vector typically takes the form of a plasmid, especially a plasmid with a unique restriction endonuclease site, more especially a restriction site within a phenotypic sequence. Various techniques can be employed for inserting the cDNA into the vector, including homopolymer tailing and the direct ligation of "sticky ends" produced following digestion of both the cDNA and the vector with a restriction endonuclease.

The recombinant plasmids containing the cDNA can then be introduced into a suitable host, for example a strain of E. coli for transformation and thereby give the cDNA bank. The transformed hosts may then be selected on the basis of a phenotype modification used as a marker, for example antibiotic resistance such as tetracycline resistance or ampicillin resistance.

It is then necessary to select from amongst the transformants the clones which contain DNA coding for a human pancreatic elastase. This selection can be achieved by several methods, including the direct sequencing method and the colony hybridization method. In the present invention the colony hybridization method is preferred. For example, cDNA of porcine elastase I (Japanese provisional patent publication No 207583/1985 corresponding to EP157604A published Oct. 9, 1985 and further corresponding to U.S. Ser. No. 716,189 filed Mar. 26, 1985) labelled with $^{32}$P or cDNA of rat elastase II labelled with $^{32}$P can be used as the probe for human elastase.

The base sequence contained in the selected clone may, if desired, be determined. Determination can be effected, for example, by dideoxynucleotide termination sequencing using phage M13 [Messing, J et al: Nucleic Acid Res, 9, 309 (1981)] or by the Maxam-Gilbert method [Maxam, A M and Gilbert, W: Proc Natl Acad Sci USA, 74, 560 (1977)]. In the present invention, the dideoxynucleotide termination method is preferred, in order that clones having a complete DNA coding for a human pancreatic elastase can be identified.

The elastase cDNA may then be isolated from the plasmid DNA of the selected clone, inserted into an appropriate expression vector and introduced into an appropriate host in order to allow expression therein.

The expression vector originally created may be cut with approp iate restriction endonucleases to construct further vectors containing the elastase cDNA.

Bacteria such as *E. coli* or *B. subtilis*, yeasts, and mammalian cells can be employed as the host.

The DNA of the present invention may be introduced into the host of *E. coli* by transformation using any of several methods, including the Hanahan method [Hanahan, D: J Mol Biol, 166, 557 (1983)], the calcium chloride method [Dagert, M and Ehrlick, S D: Gene, 6, 23 (1979)]. the low pH method [page 49 of the Manual of Genetic Manipulation, edited by Yasuyuki Takagi, Kodansha Soientitic (1982)], etc. The Hanahan method is currently preferred.

The host thus obtained (the transformed host) can be cultured in a suitable medium to produce and accumulate the elastase or a substance having the same effect, followed by recovery thereof.

Typical media for culturing the transformed host include those comprising glucose, casamino acids, and other known components, for example, M9 medium [Miller, J: Experiments in Molecular Genetics, 431 to 433, Cold Spring Harbor Lab, New York (1972)]

The transformed host is generally cultured at 15° to 43° C. for 3 to 24 hours, with aeration or stirring, if necessary. However, when mammalian cells are used as the host, it is usually necessary to carry out the culture for 3 to 10 days.

After culturing, the transformed host can be harvested in a conventional manner, for example by centrifugation or other known techniques. When *B. subtilis*, yeast or mammalians cells are employed as the host, the elastase produced is generally secreted from the cell into the supernatant. However, when *E. coli* is employed as the host, the elastase is mainly present as an undissolved protein in inclusion bodies within the cells. In cases in which *E. coli* is used as the host, the elastase may be obtained by disruption of the cells. For example, the elastase can be obtained as a precipitate after suspending the cells in a buffer, rupturing the cells and centrifugation. The cells may be ruptured by conventional procedures, including sonication treatment, lysozyme treatment or freeze-thaw treatment.

Isolation of elastase from the supernatant or the precipitate may be practised according to the conventional methods known in the art for the purification of proteins.

The typical elastases produced by the present invention include proelastases and other elastas derivatives. After any appropriate activation, the elastases generally exhibit comparable biological activity to those purified from human pancreatic fluid. They can be used for the same purposes and in the same ways as the extracted elastases. Thus, the present invention further provides pharmaceutical compositions which comprise an elastase of this invention, together with a pharmaceutically acceptable carrier or diluent.

EXAMPLES OF THE PRESENT INVENTION

The present invention is further illustrated by the following non-limiting Examples.

SUMMARY OF THE DRAWINGS

In the Examples, reference is made to the accompanying drawings, in which:

FIG. 9 sets out a synthetic DNA linker containing part of the signal peptide coding region in the α-amylase gene of *Bacillus subtilis* and the activation peptide N-terminal coding region of elastase IIB CDNA as employed in Example 2.

FIG. 13 sets out a synthetic DNA linker containing part of the signal peptide region in the α-amylase gene of *Bacillus subtilis* and the activation peptid N-terminal of elastase IIIA cDNA, as employed in Example 3.

FIG. 18 sets out a synthetic DNA linker containing part of the signal peptide region in the α-amylase gene of *Bacillus subtilis* and the activation peptide N-terminal of elastase IIIB cDNA, as employed in Example 4.

Figure 1:
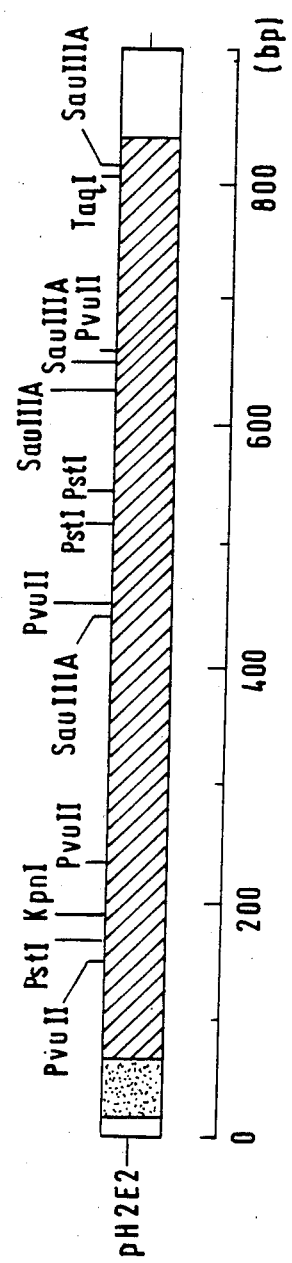
FIG. 1 is a restriction endonuclease cleavage map of part of plasmid pH2E2 obtained in Example 1, wherein the stippled portion indicates the section coding a peptide considered to be the signal peptide, and the striped portion indicates the section coding the mature elastase protein.

EXAMPLE 1:

Elastase IIA (1) Separation of mRNA from human pancreas

Human pancreas (autopsy sample) weighing 5.5 g was homogenised and denatured in a homogeniser (a polytron homogeniser from Kinematica GmbH, Germany, polytron being a Trade Mark) in an adequate amount of guanidine thiocyanate solution (4M guanidine thiocyanate; 1% detergent, Sarcosyl from Sigma Chemical Co, USA; 20 mM ethylenediaminetetraacetic acid (EDTA); 25 mM sodium citrate, pH 7.0; 100 mM 2-mercaptoethanol and 0.1% antifoaming agent, Antifoam A from Sigma Chemical Co USA), followed by centrifugation, to obtain a supernatant.

One volume of supernatant was added to 0.025 volumes of 1M acetic acid and 0.75 volumes of ethanol, and the mixture cooled to −20° C. for several hours, followed by centrifugation, to obtain a precipitate. The precipitate was suspended in a guanidine hydrochloride solution (7.5M guanidine hydrochloride; 25 mM sodium citrate, pH 7.0; and 5 mM dithiothreitol, DTT). To 1 volume of the suspension was added 0.025 volumes of 1M acetic acid and 0.5 volumes of ethanol, and the resultant mix cooled to −20° C. for several hours, followed by centrifugation. The resultant precipitate was suspended again in more of the guanidine hydrochloride solution, mixed as before with acetic acid and ethanol, cooled to −20° C. and centrifuged, followed by collection of the precipitate. Next, the precipitate was washed several times with ethanol to remove guanidine hydrochloride, and then dissolved in distilled water, followed by precipitation of the RNA with ethanol. The precipitate was collected by centrifugation to give 53.9 mg of RNA.

The RNA thus obtained was adsorbed onto an oligo(dT) cellulose column in a high concentration salt solution (0.5M NaCl; 20 mM Tris-HCl, pH 7.5; 1 mM EDTA; and 0.1% sodium dodecyl sulfate, SDS), and the mRNA-containing poly(A) was eluted with an elution buffer (10 mM Tris-HCl, pH 7.5; 1 mM EDTA; and 0.05% SDS) to give 255 μg of mRNA.

(2) Preparation of cDNA bank

The preparation of a cDNA bank was carried out according to the Okayama-Berg method. 5 μg of the mRNA and 24 units of a reverse transcriptase were incubated at 42° C. for 60 minutes in 20 μl of a reaction mixture (50 mM of Tris-HCl, pH 8.3; 8 mM of MgCl$_2$; 30 mM of KCl; 0.3 mM of DTT; 2 mM each of dATP, dGTP, dCTP and dTTP; 10 μCi of α-$^{32}$P-dCTP; and 1.4 μg of vector primer DNA, purchased from PL-Pharmacia).

The reaction was stopped by the addition of 2 μl of 0.25M EDTA and 1 μl of 10% SDS. Deproteinization was carried out with 20 μl of phenol-chloroform. After centrifugation of the reaction mixture, the aqueous layer was collected. 20 μl of 4M ammonium acetate and 80 μl of ethanol were added to the aqueous layer and the mixture cooled to −70° C. for 15 minutes. The precipitate was then collected by centrifugation and washed with 75% aqueous ethanol and dried under reduced pressure.

The resultant precipitate was dissolved in 15 μl of terminal transferase reaction mixture (140 mM potassium cacodylate, of formula $C_2H_6AsKO_2$; 30 mM Tris-HCl, pH 6.8; 1 mM cobalt chloride; 0.5 mM DTT; 0.2 μg of poly(A); and 100 mM of dCTP). After incubating the solution at 37° C. for 3 minutes, 18 units of terminal deoxynucleotidyl transferase were added and allowed to react for 5 minutes.

The above reaction was stopped by addition of 1 μl of 0.25M EDTA and 0.5 μl of 10% SDS. Deproteinization was then carried out With phenol-chloroform. After centrifugation of the reaction mixture, the aqueous layer was collected. 15 μl of 4M ammonium acetate and 60 μl of ethanol were added to the aqueous layer and mixed well. After cooling the mixture to −70° C. for 15 minutes, the precipitate was collected by centrifugation.

The precipitate was dissolved in 10 μl of a buffer for restriction endonuclease (50 mM NaCl; 10 mM Tris-HCl, pH 7.5; 10 mM MgCl ; and 1 mM DTT). 2.5 units of the restriction enzyme HindIII were added to the solution and the solution digested at 37° C. for about 1 hour. After deproteinization with phenol-chloroform, precipitation was carried out with ethanol.

After cooling to −70° C. for 15 minutes, the precipitate was collected by centrifugation and dissolved in 10 μl of TE (10 mM Tris-HCl, pH 7.5; 1 mM EDTA). 1 μl of the above sample solution was then added to a reaction solution (10 mM Tris-HCl, pH 7.5; 1 mM EDTA; and 100 mM NaCl), followed by addition of 10 ng of linker (purchased from PL-Pharmacia) bearing oligo dG. The resulting mixture was heated at 65° C. for 5 minutes and maintained at 42° C. for 30 minutes.

After cooling the reaction solution in ice water, 10 μl of 10-fold ligase buffer solution (10 mM ATp; 660 mM Tris-HCl, pH 7.5; 66 mM MgCl$_2$; and 100 mM DTT), 78 μl of distilled water and 8 units of T4 DNA ligase were added to the solution and the reaction mixture maintained at 12° C. overnight.

Then, to the thus prepared mixture, 10 μl of 1M KCl, 1 unit of ribonuclease H, 33 units of DNA polymerase I, 4 units of T4 DNA ligase, 0.5 μl of nucleotide solution (20 mM dATP, 20 mM dGTP, 20 mM dCTP and 20 mM dTTP) and 0.1 μl of 50 μg/μl bovine serum albumin (BSA) were added and the mixture maintained at 12° C. for 1 hour and then at 25° C. for 1 hour.

After diluting the reaction solution 5-fold, *E. coli* strain RR1 was transformed according to the method of Hanahan [Hanahan, D; J Mol Biol 166, 557 (1983)] to prepare a human pancreatic cDNA bank.

(3) Selection of transformed bacteria containing human pancreatic elastase IIA cDNA The DNA from 4,700 clones of the human pancreactic cDNA bank was fixed onto nitrocellulose filter according to the method of Grunstein, M and Hogness, D S [Proc Natl Acad Sci, USA, 72, 3961 (1975)].

In order to select a clone including a plasmid containing human pancreatic elastase IIA cDNA, a rat pancreatic elastase II cDNA fragment was employed as a probe. The rat pancreatic elastase II cDNA was obtained by the following method. Firstly, a cDNA bank was prepared using mRNA extracted from rat pancreas. Then, an oligodeoxynucleotide 5'd(GGCATAGT-CCACAACCA)3' comprising 17 bases was synthesized complementary to a part of the known base sequence of rat pancreatic elastase II mRNA [MacDonald, R et al Biochem, 21, 1453 (1982)]. The oligodeoxynucleotide corresponds to the amino acid sequence from amino acid 151 to amino acid 156 of the rat pancreatic elastase II. The 5'-end of the oligodeoxynucleotide was labelled with $^{32}$P by the method of Maxam, A M and Gilbert, W [Proc Natl Acad Sci, USA 74, 560 (1977)] to give a probe. Using the probe, a rat pancreatic elastase II cDNA clone was selected from the rat pancreatic cDNA bank. Then a fragment containing 200 bases was excised from the rat pancreatic elastase II cDNA with restriction endnucleases AatII and HindIII and labelled with $^{32}$P according to the nick translation method [Rigby, p W et al: J Mol Biol 113, 237 (1977)]. The DNA fragment was then used as a probe for hybridization with the DNA fixed on the nitrocellulose filter, according to the method of Alwine, S C et al [Proc Natl Acad Sci, USA 74, 5350 (1977)].

8 clones reactive with the probe were identified by autoradiography. A plasmid from one of the strains was named "pH2E2".

The restriction endonuclease cleavage map of the DNA inserted in pH2E2 was determined and is shown in FIG. 1. The base sequence was determined and is of the formula (5')-TT TTA CAG AAC TCC
CAC GGA CAC ACC ATG ATA AGG ACG CTG CTG
CTG TCC ACT TTG GTG GCT GGA GCC CTC AGT
TGT GGG GAC CCC ACT TAC CCA CCT TAT GTG
ACT AGG GTG GTT GGC GGT GAA GAA GCG AGG
CCC AAC AGC TGG CCC TGG CAG GTC TCC CTG
CAG TAC AGC TCC AAT GGC AAG TGG TAC CAC
ACC TGC GGA GGG TCC CTG ATA GCC AAC AGC
TGG GTC CTG ACG GCT GCC CAC TGC ATC AGC
TCC TCC AGG ACC TAC CGC GTG GGG CTG GGC
CGG CAC AAC CTC TAC GTT GCG GAG TCC GGC
TCG CTG GCA GTC AGT GTC TCT AAG ATT GTG
GTG CAC AAG GAC TGG AAC TCC AAC CAA ATC
TCC AAA GGG AAC GAC ATT GCC CTG CTC AAA
CTG GCT AAC CCC GTC TCC CTC ACC GAC AAG
ATC CAG CTG GCC TGC CTC CCT CCT GCC GGC
ACC ATT CTA CCC AAC AAC TAC CCC TGC TAC
GTC ACG GGC TGG GGA AGG CTG CAG ACC AAC
GGG GCT GTT CCT GAT GTC CTG CAG CAG GGC
CGG TTG CTG GTT GTG GAC TAT GCC ACC TGC
TCC AGC TCT GCC TGG TGG GGC AGC AGC GTG
AAA ACC AGT ATG ATC TGT GCT GGG GGT GAT -continued GGC GTG ATC TCC AGC TGC AAC GGA GAC TCT
GGC GGG CCA CTG AAC TGT CAG GCG TCT GAC
GGC CGG TGG CAG GTG CAC GGC ATC GTC AGC
TTC GGG TCT CGC CTC GGC TGC AAC TAC TAC
CAC AAG CCC TCC GTC TTC ACG CGG GTC TCC
AAT TAC ATC GAC TGG ATC AAT TCG GTG ATT
GCA AAT AAC TAA CCA AAA GAA GTC CCT GGG
ACT GTT TCA GAC TTG GAA AGG TCA CAG AAG
GAA AAT AAT ATA ATA AAG TGA CAA CTA TGC
-(3')

Beginning at the underlined ATG triplet, the encoded amino acid sequence is of the formula:

(N)- Met Ile Arg Thr Leu Leu
Leu Ser Thr Leu Val Ala Gly Ala Leu Ser
Cys Gly Asp Pro Thr Tyr Pro Pro Tyr Val
Thr Arg Val Val Gly Gly Glu Glu Ala Arg
Pro Asn Ser Trp Pro Trp Gln Val Ser Leu
Gln Tyr Ser Ser Asn Gly Lys Trp Tyr His
Thr Cys Gly Gly Ser Leu Ile Ala Asn Ser
Trp Val Leu Thr Ala Ala His Cys Ile Ser
Ser Ser Arg Thr Tyr Arg Val Gly Leu Gly
Arg His Asn Leu Tyr Val Ala Glu Ser Gly
Ser Leu Ala Val Ser Val Ser Lys Ile Val
Val His Lys Asp Trp Asn Ser Asn Gln Ile
Ser Lys Gly Asn Asp Ile Ala Leu Leu Lys
Leu Ala Asn Pro Val Ser Leu Thr Asp Lys
Ile Gln Leu Ala Cys Leu Pro Pro Ala Gly
Thr Ile Leu Pro Asn Asn Tyr Pro Cys Tyr
Val Thr Gly Trp Gly Arg Leu Gln Thr Asn
Gly Ala Val Pro Asp Val Leu Gln Gln Gly
Arg Leu Leu Val Val Asp Tyr Ala Thr Cys
Ser Ser Ser Ala Trp Trp Gly Ser Ser Val
Lys Thr Ser Met Ile Cys Ala Gly Gly Asp
Gly Val Ile Ser Ser Cys Asn Gly Asp Ser
Gly Gly Pro Leu Asn Cys Gln Ala Ser Asp
Gly Arg Trp Gln Val His Gly Ile Val Ser
Phe Gly Ser Arg Leu Gly Cys Asn Tyr Tyr
His Lys Pro Ser Val Phe Thr Arg Val Ser
Asn Tyr Ile Asp Trp Ile Asn Ser Val Ile
Ala Asn Asn -(C)

It can be seen that plasmid pH2E2 has a region coding for a signal peptide comprising 16 amino acids and a region coding for the mature elastase protein termed elastase IIA. The elastase IIA comprises 253 amino acids. plasmid pH2E2 also contains 5' and 3' non-translated regions.

There is as much as 84% homology between the amino acid sequence coded by the DNA insertion of plasmid pH2E2, and that of rat pancreatic elastase II reported by MacDonald, R J et al [Biochem, 21, 1453 (1982)]. Accordingly, plasmid pH2E2 is believed to contain cDNA coding a human pancreatic elastase II. With regard to the known sequence for human pancreatic elastase II, the 16 amino acid residue at the N-terminal of pH2E2 coding protein is identical to that of the human pancreatic elastase II reported by Largman, C, et al [Biochim Biophys Acta 623, 208 (1980)].

Since pH2E2 contains an entire DNA coding for human pancreatic elastase IIA, it is possible to produce large amounts of the elastase IIA by transferring the cDNA to an appropriate expression vector and using, for example, *E coli, B. subtilis.* Yeast or mammalian cells as the host.

(4) production of human pancreatic elastase IIA using mammalian cells

Construction of expression plasmid pSV2-E2A

Figure 2:
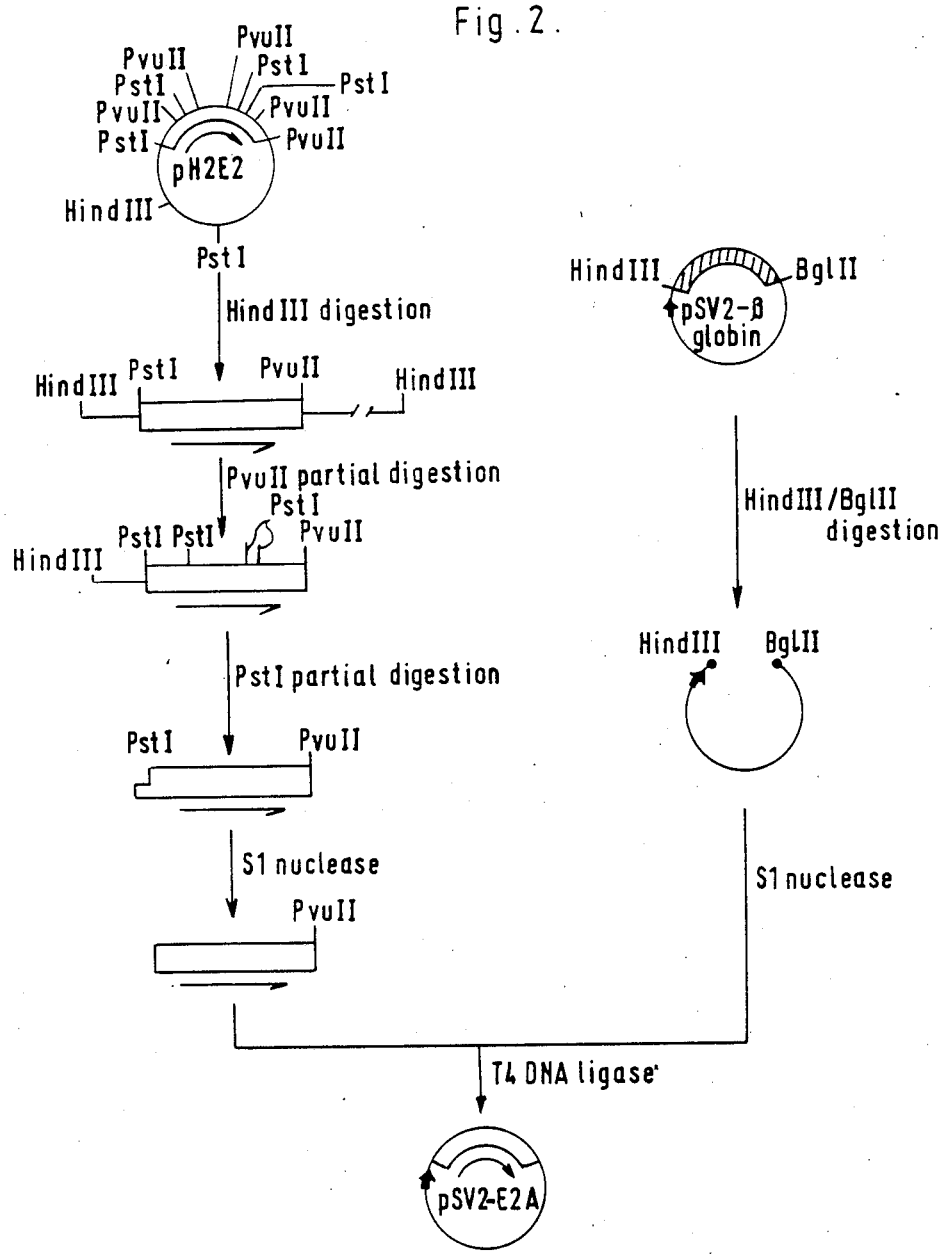
FIG. 2 illustrates the construction of plasmid pSV2-E2A in Example 1.

In order to produce human elastase IIA using mammalian cells as host, the cDNA was ligated to an expression vector according to the procedure indicated in FIG. 2. The known pSV2 plasmid containing the SV40 promoter, enhancer, poly(A) signal and introns of the Small T antigen SV40 gene was used for construction of the expression vector. pSV2-$\beta$-globin is a plasmid based on the pSV2 vector with inserted $\beta$-globin cDNA. plasmid pH2E2 is the plasmid with inserted human elastase IIA cDNA. The reactions for with S1 nuclease, etc. were carried out according to the methods described in "Molecular Cloning" [Maniatis, T et al (ed) "Molecular Cloning" Cold Spring Harbor Lab (1982)]. The broad arrows in FIG. 2 represent the promoter derived from SV40, and the narrow arrows show the direction of transcription.

From analysis of the restriction endonuclease digestion pattern, an expression plasmid (pSV2-E2A) was selected in which vector and cDNA were ligated in the correct orientation for transcription.

Transfection of COS 1 cells with expression plasmid pSV2-E2A

The constructed expression plasmid pSV2-E2A was transfected into COS 1 (mammalian cells) by the calcium phosphate method described in the literature [Graham and van der Eb: Virology 52 456 (1973)].

Thus, $1\times10^6$ of COS 1 cells were seeded on petri Dulbecco-modified Eagle medium containing 10% fetal calf serum.

Plasmid pSV2-E2A (300 $\mu$g) was suspended in sterile distilled water (12.55 ml), then 2.5M CaCl$_2$ (0.75 ml) was added and the suspension mixed thoroughly. A pipette was used to bubble air through the system in order to maintain agitation, and 1.5 ml of 10$\times$HeBS solution (HEPES, 210 mM; NaCl, 1.37M; KCl 4.7 mM; Na 10.6 mM; glucose, 55.5 mM; pH 7.05) was dropped into the resulting solution to precipitate the DNA and calcium phosphate.

The precipitate was allowed to stand at room temperature for 30 minutes to mature the precipitate, and 1 ml of the solution for each petri dish was added to the COS 1 cells cultured in fresh medium containing 10% fetal calf serum.

After cultivation of these cells for 12 hours at 37° C. in the presence of 5% CO$_2$, the culture medium was discarded in favour of a fresh, Dulbecco-modified Eagle medium containing no fetal calf serum. The cells were cultured for a further 48 hours at 37° C. in the presence of 5% CO$_2$. The transfected COS 1 cells obtained by this procedure were tested to detect the presence of human elastase IIA mRNA, while the supernatant of the culture medium was tested for elastase activity.

Extraction of mRNA from COS 1 cells

In order to confirm the existence of human elastase IIA mRNA transcribed from the expression plasmid in the transfected COS 1 cells, mRNA was extracted from the COS 1 cells and assayed by Northern blot hybridization according to the following procedure.

After cultivation of the COS 1 cells for 48 hours, 1 ml of guanidine thiocyanate solution (4M guanidine thiocyanate; 1% Sarcosyl; 20 mM EDTA; 25 mM sodium citrate, pH 7.0; 100 mM 2-mercaptoethanol; 0.1% Antifoam A) was added to each petri dish in order to lyse the cells.

High molecular DNA molecules were degraded to low molecular ones by passing the solution several times through a 21 guage injection needle. The resultant solution was layered on a solution containing 5.7M cesium chloride and 0.1M EDTA, and the solution centrifuged at 20° C., 30,000 rpm for 17 hours using a Hitachi RPS 40 swing rotor. The resultant RNA precipitate was washed with a small amount of ethanol and dissolved in distilled water (300 $\mu$l). According to the method of Aviv and Leder [Proc Natl Acad Sci, USA 69, 1408 (1972)], the extracted total RNA was purified on an oligo(dT) cellulose column to give several $\mu$g of purified mRNA. Half of the purified mRNA was used for Northern blot hydridization by the Thomas method [Proc Natl Acad Sci, USA 77 5201 (1980)]. $^{32}$P-Labelled human elastase IIA cDNA was used as a probe by the nick translation method [Rigby, p W et al: J Mol Biol 113, 237 (1977)]. A major band at about 1.8 Kb and a minor band at about 1.0 Kb which hydridized with the probe were detected only in the mRNA of COS 1 cells transfected with plasmid pSV2-E2A. It was assumed that in the transcription of the plasmid pSV2-E2A, the 1.8 Kb mRNA is formed on termination of transcription at the poly(A) signal cohtained in the vector, while the 1.0 Kb mRNA is formed on termination of transcription at the poly(A) signal in the cDNA. The results from the Northern blot hybridization coincided with these assumptions.

The results thus show that using SV40 promoter in COS 1 cells, the plasmid pSV2-E2A can synthesize large quantities of human elastase IIA mRNA.

Elastase activity in supernatant of the culture broth

Since the human elastase IIA cDNA in pSV2-E2A has a signal peptide region, secretion of expressed elastase into the medium as a proelastase was expected. Elastase activity in the medium after 48 hours cultivation was accordingly determined. Tris-HCl buffer solution (pH 8.0) was added to the supernatant of the culture medium (1 ml) to a final concentration of 0.2M, 10 mg/ml trypsin (50 $\mu$l) was added, and an activation treatment of the proelastase was carried out for 15 minutes at 25° C. Next, 50 $\mu$l of soybean trypsin inhibitor solution (10 mg/ml) and a synthetic substrate, glutaryl-Ala-Ala-pro-Leu-p-nitroanilide were added, and the enzyme reaction was carried out by incubation at 25° C. After completion of the reaction, liberated p-nitroanilide was determined by measuring absorbance at 410 nm.

The elastase aotivity in the culture medium of COS 1 cells transfected with pSV2-E2A was distinctly detected, and the production of active human elastase IIA in COS 1 cells was found.

The activation treatment with trypsin or other activator was indispensable.

The production of human elastase IIA in COS 1 cells transfected with plasmid pSV2-E2A was transient. However, if plasmid pSV2-E2A is linked with a suitable selection marker (for example, the neo gene, dihydrofolate reductase gene, or other resistance marker) and is transfected in to CHO or other cells, a cell line suitable for sustained production of human elastase IIA can be prepared.

(5) Production of human pancreatic elastase IIA using Bacillus subtilis

Construction of expression vector pBSEX-E2A

Figure 3:
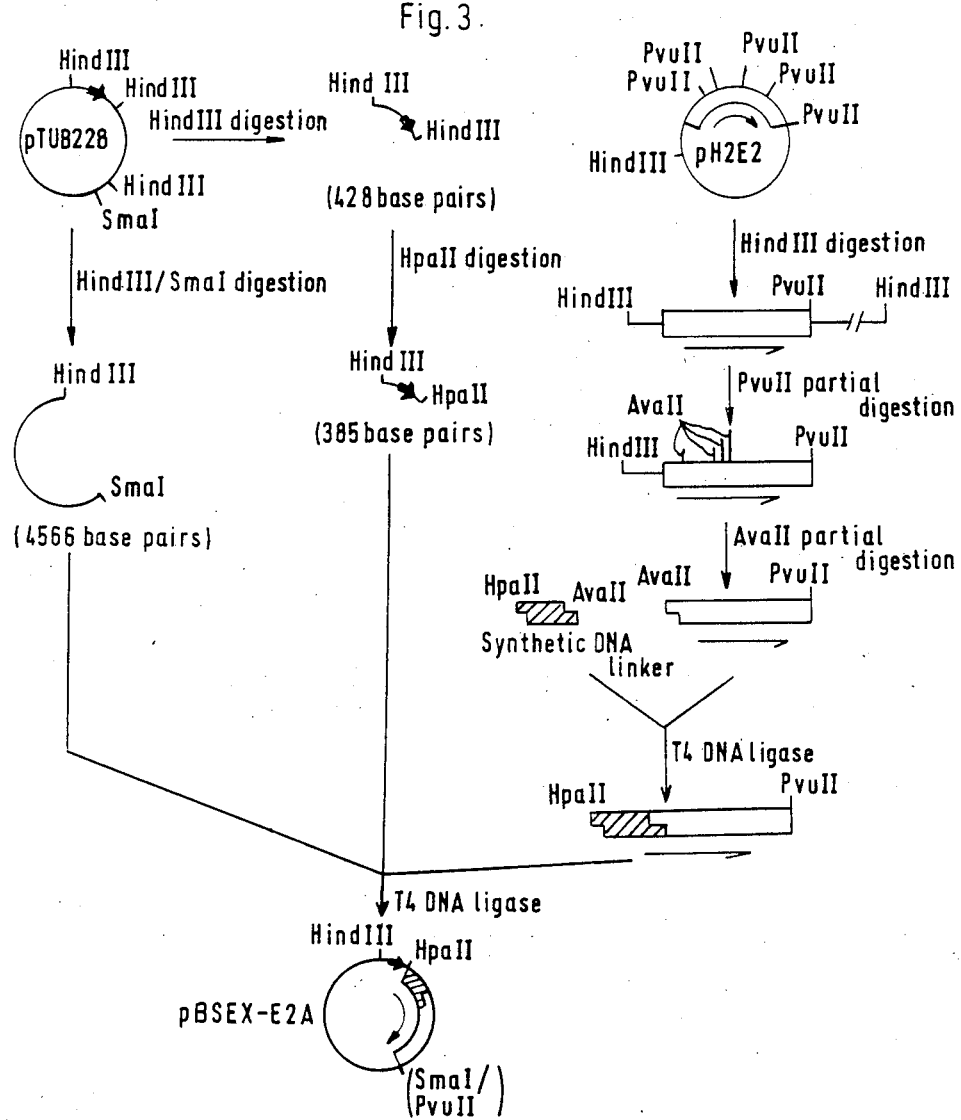
FIG. 3 illustrates the construction of plasmid pBSEX-E2A in Example 1.
Figure 4:
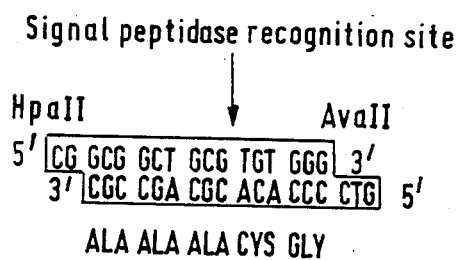
FIG. 4 sets out a synthetic DNA linker containing part of the signal peptide region in the α-amylase gene of *Bacillus subtilis* and the activation peptide N-terminal of elastase IIA cDNA, as employed in Example 1.

The construction method for the expression vector is illustrated in FIG. 3. plasmid pH2E2 containing human elastase IIA cDNA was digested with restriction endonuclease HindIII to a linear DNA, and then partially digested with restriction enzyme PvuII. A DNA fragment of about 1.3 Kb containing the elastase IIA cDNA was isolated. This fragment was partially digested with restriction endonuclease AvaII to give a fragment containing cDNA coding for the amino acid sequence beginning from the third amino acid counted from the N-terminal end of the elastase IIA activation peptide. The specific oligonucleotide sequence shown in FIG. 4 was synthesized. This sequence codes for part of the signal peptide of B. subtilis α-amylase, and two amino acids (Cys, Gly) at the N-terminal end of the elastase IIA activation peptide. The fragments were ligated with T4 DNA ligase.

On the other hand, plasmid pTUB228 [Ohmura, K et al: J Biochem 95 87 (1984)] containing the α-amylase gene of Bacillus subtilis was digested with restriction endonuclease HindIII to isolate a DNA fragment of 428 base pairs containing the α-amylase promoter and a part of the signal peptide, and separately a DNA fragment of 5,100 base pairs containing the replication origin. The DNA fragment of 428 base pairs and the DNA fragment of 5,100 base pairs were further digested with restriction endonuclease HpaII and SmaI, respectively, to give DNA fragments of 385 base pairs and of 4566 base pairs.

The three DNA fragments were ligated with T4 DNA ligase, and incorporated into protoplasts of Bacillus subtilis 207-25 strain (m$_{168}^-$ hsrM recE4 amyEO7 aroI906 leuA8 lys21; derived from Marburg strain) according to conventional procedures. After regeneration, cultivation on a medium containing 10 μg/ml of kanamycin allowed selection of the transformed strains which could grow on this medium. Selection of the desired plasmid was achieved through colony hybridization using as probe the synthetic oligonucleotide of FIG. 4. A positive clone was identified and the plasmid shown to be the intended one by determination of the base sequence.

The expression plasmid obtained in this manner was designated plasmid pBSEX-E2A.

Elastase activity in supernatant of the culture broth Bacillus subtilis 207-25 strain transformed with the human elastase IIA expression plasmid pBSEX-E2A was cultured on a reciprocal shaker in 1 l of LG medium (1% Bacto trypton, Difco; 0.5% yeast extract, Difco; 0.5% NaCl; 0.2% glucose; pH 7.0) containing 50 μg/ml of kanamycin. The culturing was performed at 35° C. for 48 hours.

After completion of the culture, the culture medium was cooled to 4° C. and centrifuged at 3000×G for 5 minutes, and the cells discarded. Ammonium sulfate was added to the supernatant to 55% saturation, and the solution was stirred at 4° C. for 12 hours. Insoluble material formed in this treatment was precipitated by centrifugation at 8000×G for 20 minutes, the supernatant was discarded, and the precipitate was dissolved in 20 ml of 0.2M Tris-HCl buffer solution (pH 8.0). This solution was dialyzed against 1 l of 0.2M Tris-HCl buffer solution (pH 8.0) for 16 hours, and insoluble material was removed by centrifugation at 8000×G for 20 minutes. The dialyzed solution was. taken as a crude elastase IIA sample solution, and the activity was determined by the following procedure.

Determination of Elastase Activity in the Sample Solution

Proelastase was activated by trypsin treatment of the sample solution, and allowed to react at 25° C. with a synthetic substrate, glutaryl-Ala-Ala-Pro-Leu-P-nitroanilide. Liberated p-nitroanilide was determined by measuring absorbance at 410 nm. Since elastase activity was distinctly detected in the sample solution from the 207-25 strain transformed with pBSEX-E2A, the production of active human elastase IIA in Bacillus subtilis was demonstrated.

(6) Production of human pancreatic elastase IIA using Escherichia coli

Various different promoters may be used, including for instance the tryptophan (trp) promoter, lactose (lac) promoter, tryptophan-lactose (tac) promoter, lipoprotein (lpp) promoter, lambda (λ) P$_L$ promoter derived from bacteriophage, or polypeptide chain elongation factor (tuf B) promoter. An example with the lactose promoter is as follows.

Figure 5:
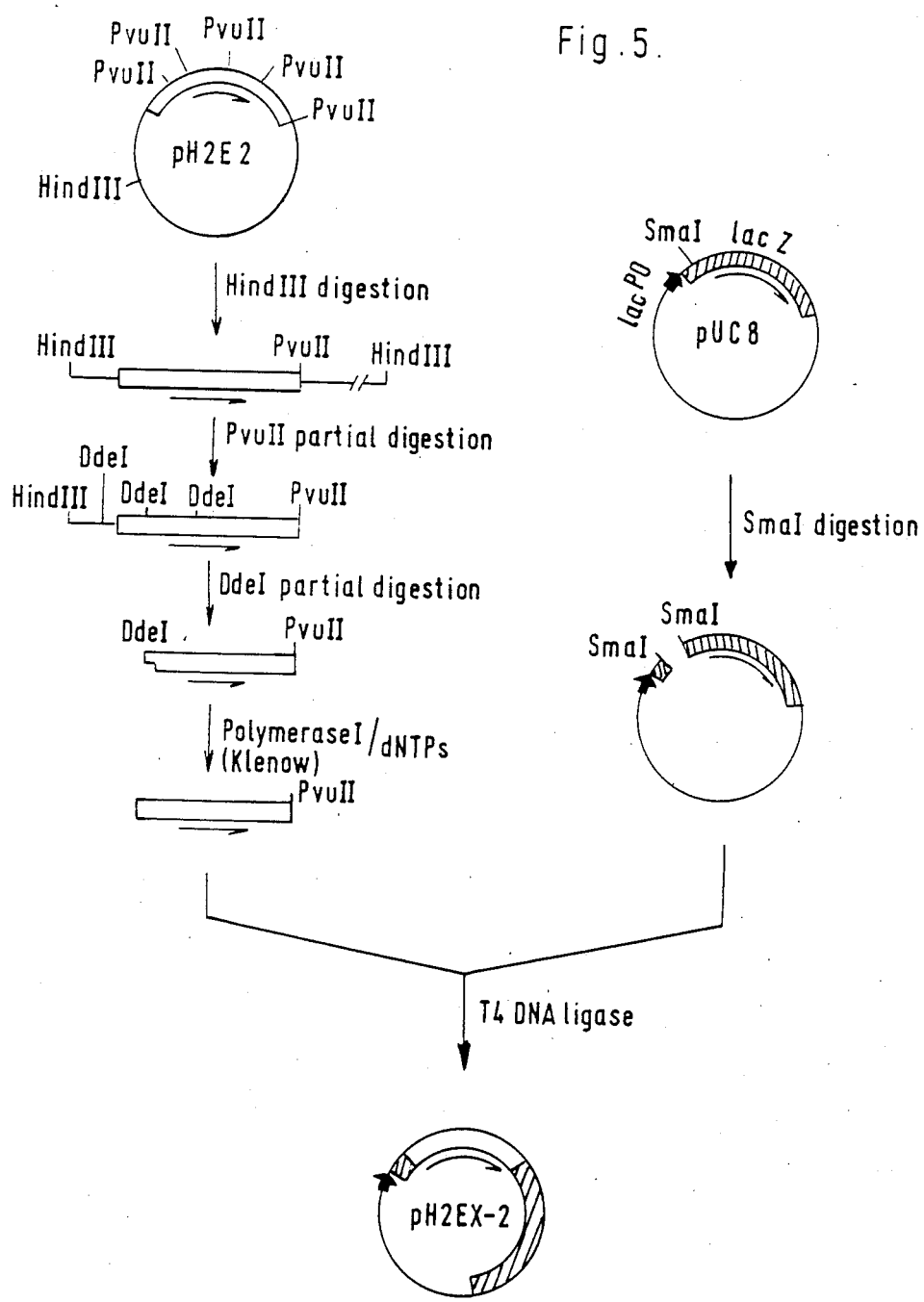
FIG. 5 illustrates the construction of plasmid pH2EX-2 in Example 1. The striped area represents the β-galactosidase gene. Broad arrows indicate the lactose promoter and operator, and narrow arrows show the direction of transcription.

As shown in FIG. 5, plasmid pH2E2 containing human elastase IIA cDNA was digested with restriction endonuclease HindIII to form a linear DNA, and then partially digested with restriction enzyme PvuII to isolate a DNA fragment of about 1.3 Kb containing elastase IIA cDNA.

This fragment was partially digested with restriction endonuclease DdeI to give a fragment containing cDNA coding for an amino acid sequence down stream from the activation peptide of elastase IIA. By treatment of this DNA fragment with DNA Polymerase Klenow fragment and four kinds of deoxyribonucleoside 5'-triphosphates (dATP, dCTP, dGTP, dTTP), both ends were converted to blunt ends. The resultant DNA fragment was inserted into the SmaI site of plasmid pUC8.

Escherichia coli strain JM103 was transformed with the plasmid. plasmid was extracted from several transformed strains, and through the use of restriction endonuclease mapping, plasmid with the same orientation of cDNA transcription and of the promoter for the lactose operon was selected . This elastase IIA expression plasmid was designated as pH2EX-2.

The base sequence and corresponding amino acid sequence for around the 5'-end of the elastase cDNA in pH2EX-2 are as follows.

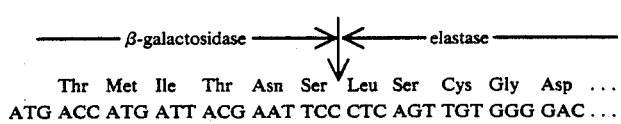

Therefore, the human elastase-IIA expressed by pH2EX-2 is shown to be a fused protein in which two amino acids (Leu, Ser) derived from the signal peptide and six amino acids derived from β-galactosidase combine at the N-terminal.

Several *Escherichia coli* strains were transformed with pH2EX-2 to give strains capable of producing human elastase IIA. The strains containing expression plasmid were inoculated in 2 x TY-ampicillin medium (1.6% Bacto trypton; 1% yeast extract; 0.5% NaCl; 50 μg/ml ampicillin) and cultured at 37° C. for 15 hours. After completion of the culture, cells were harvested by centrifugation of the culture medium, $2.4 \times 10^8$ cells were suspended in 15 μl of SDS solution (2% SDS, 5% 2-mercaptoethanol; 10% glycerin; 60 mM Tris-HCl, pH 6.8). The cell suspension was heated at 100° C. for 3 minutes, and protein was analyzed by SDS polyacrylamide gel electrophoresis, according to the method of Laemmli et al [Nature, 227 680 (1970)].

As a result, a large quantity of elastase production was found in strain YA21. The production yield of elastase the YA21 strain. Though a considerable production of elastase fusion protein in χ984 strain was observed, the production yield was less than half that in the YA21 strain The production yields in two other *Esherichia coli* strains (HB101 and MC4100 strains) were low.

Since the elastase fusion protein forms inclusion bodies in cells, purification was comparatively easy. Thus, from 1 l of a culture medium of YA21 strain transformed with plasmid pH2EX-2 , 6.5 g of cells forming inclusion bodies could be obtained. The obtained cells (6.5 g) were lysed in 50 mM Tris-HCl buffer solution (pH 8.0) containing 0.2 mg/ml lysozyme and 1 mg/ml deoxycholic acid. Intact cells were removed by low speed centrifugation ($1,500 \times G$, 10 minutes) and inclusion bodies were recovered as a precipitate by high speed centrifugation ($11,000 \times G$, 20 minutes), Since the precipitate still contained much cell debris, the precipitate was suspended in 50 mM Tris-HCl buffer solution containing 5 mg/ml octylphenoxy polyethoxyethanol surfactant (Triton X-100, Trade Mark) and washed by high speed centrifugation ($11,000 \times G$, 20 minutes). A washed pellet of inclusion bodies was suspended in a small amount of Tris-HCl buffer solution and stored at 4° C.

The purified inclusion body (300 mg) containing about 50% elastase IIA fusion protein could be obtained by this procedure. The inclusion body produced by YA21 strain transformed with pH2EX-2 was shown to contain the elastase fusion protein by immuno-blotting.

Though most of the elastase produced by *Escherichia coli* is in the insoluble fraction of the cells as inclusion bodies, a smaller proportion exists in a soluble state and retains enzyme activity. Determination of the enzyme activity was carried out as follows. The strain χ984 strain transformed with plasmid pH2EX-2 was cultured with shaking in 1 l of 2×TY-ampicillin medium at 37° C. for 15 hours. After completion of the culturing, the cells were harvested by centrifugation at $3000 \times G$ for 5 minutes and suspended in 20 ml of buffer solution A (50 mM Tris-HCl, pH 8.0; 1 mM EDTA; 50 mM NaCl). 10 mg of lysozyme was added, and the suspension incubated at 5° C. for 20 minutes. Deoxycholic acid to a final concentration of 1 mg/ml was added to the resultant suspension which was then incubated at 20° C. Deoxyribonuclease to a final concentration of 0.1 mg/ml was added. and the cells were disrupted in a polytron homogenizer. After removal of the cell debris by centrifugation at $80,000 \times G$, 40 minutes, the lysate was subjected to column chromatography on high molecular weight, cross-linked dextran (Sephadex G-78, a gel filtration material able to separate substances of molecular weight 1,000 to 5,000). The fractions having elastase activity were purified by antibody affinity chromatography, and used for the following determination of elastase activity.

Proelastase was activated by trypsin treatment of the sample solution. Next, p-nitroanilide liberated by the reaction with a synthetic substrate, glutaryl-Ala-Ala-Pro-Leu-P-nitroanilide, was determined by measuring the absorbance at 410 nm. The reaction was carried out by incubation at 25° C. in 0.2M Tris-HCl buffer solution (pH 8.0) containing the synthetic substrate. As a result, elastase activity was distinctly detected in the sample solution of strain χ984 transformed with plasmid pH2EX-2, and therefore the production of active human elastase IIA was demonstrated.

(7) Production of human pancreatic elastase IIA using Yeast

In the case of yeast as a hose (as as with a *Escherichia coli, Bacillus subtilis* or mammalian cells). human pancreatic elastase IIA cDNA could be linked with a suitable expression vector using known techniques, introduced into the host cells and expressed. Elastase activity in the culture medium was confirmed.

*Saccharomyces cerevisiae* described in "Japanese Guidelines for Recombinant DNA Research" may be used as host, but S288C strain and other strains are practically suitable. On the other hand, YEp13 and other vectors were appropriate as a vector. As promoter, the ADH1 gene coding for alcohol dehydrogenase gene, and other promoters, are suitable.

EXAMPLE 2:

Elastase iib (1)) Separation of mRNA from human pancreas

Human pancreas (autopsy sample) weighing 5.5 g was homogenised and denatured in a homogeniser (a polytron homogeniser from Kinematica GmbH, Germany, Polytron being a Trade Mark) in an adequate amount of guanidine thiocyanate solution (4M guanidine thiocyanate; 1% detergent, Sarcosyl from Sigma Chemical Co, USA; 20 mM ethylenediaminetetraacetic acid (EDTA); 25 mM sodium citrate, pH 7.0; 100 mM 2-mercaptoethanol and 0.1% antifoaming agent, Antifoam A from Sigma Chemical Co USA), followed by centrifugation, to obtain a supernatant.

One volume of supernatant was added to 0.025 volumes of 1M acetic acid and 0.75 volumes of ethanol, and the mixture cooled to −20° C. for several hours, followed by centrifugation, to obtain a precipitate. The precipitate was suspended in a guanidine hydrochloride solution (7.5M guanidine hydrochloride; 25 mM sodium citrate , pH 7.0; and 5 mM dithiothreitol, DTT). To 1 volume of the suspension was added 0.025 volumes of 1M acetic acid and 0.5 volumes of ethanol, and the resultant mix cooled to −20° C. for several hours, followed by centrifugation. The resultant precipitate was suspended again in more of the guanidine hydrochloride solution, mixed as before with acetic acid and ethanol, cooled to −20° C. and centrifuged, followed by collection of the precipitate. Next, the precipitate was washed several times with ethanol to remove guanidine hydrochloride, and then dissolved in distilled water, followed by precipitation of the RNA with ethanol. The precipitate was collected by centrifugation to give 53.9 mg of RNA.

The RNA thus obtained was adsorbed onto an oligo(dT) cellulose column in a high concentration salt solution (0.5M NaCl; 20 mM Tris-HCl, pH 7.5; 1 mM EDTA; and 0.1% sodium dodecyl sulfate, SDS), and the mRNA-containing poly(A) was eluted with an elution buffer (10 mM Tris-HCl, pH 7.5; 1 mM EDTA; and 0.05% SDS) to give 255 µg of mRNA.

(2) Preparation of cDNA bank

The preparation of a cDNA bank was carried out according to the Okayama-Berg method. 5 µg of the mRNA and 24 units of a reverse transcriptase were incubated at 42° C. for 60 minutes in 20 µl of a reaction mixture (50 mM of Tris-HCl, pH 8.3; 8 mM of $MgCl_2$; 30 mM of KCl; 0.3 mM of DTT; 2 mM each of dATP, dGTP, dCTP and dTTP; 10 µCi of $\alpha$-$^{32}$p-dCTP; and 1.4 µg of vector primer DNA, purchased from PL-Pharmacia).

The reaction was stopped by the addition of 2 µl of 0.25M EDTA and 1 µl of 10% SDS. Deproteinization was carried out with 20 µl of phenol-chloroform. After centrifugation of the reaction mixture, the aqueous layer was collected. 20 µl of 4M ammonium acetate and 80 µl of ethanol were added to the aqueous layer and the mixture cooled to $-70°$ C. for 15 minutes. The precipitate was then collected by centrifugation and washed with 75% aqueous ethanol and dried under reduced pressure.

The resultant precipitate was dissolved in 15 µl of terminal transferase reaction mixture (140 mM potassium cacodylate, of formula $C_2H_6AsKO_2$; 30 mM Tris-HCl, pH 6.8; 1 mM cobalt chloride; 0.5 mM DTT; 0.2 µg of poly(A); and 100 mM of dCTP). After incubating the solution at 37° C. for 3 minutes, 18 units of terminal deoxynucleotidyl transferase were added and allowed to react for 5 minutes.

The above reaction was stopped by addition of 1 µl of 0.25M EDTA and 0.5 µl of 10% SDS. Deproteinization was then carried out with phenol-chloroform. After centrifugation of the reaction mixture, the aqueous layer was collected. 15 µl of 4M ammonium acetate and 60 µl of ethanol were added to the aqueous layer and mixed well. After cooling the mixture to $-70°$ C. for 15 minutes, the precipitate was collected by centrifugation.

The precipitate was dissolved in 10 µl of a buffer for restriction endonuclease (50 mM NaCl; 10 mM Tris-HCl, pH 7.5; 10 mM $MgCl_2$; and 1 mM DTT). 2.5 units of the restriction enzyme HindIII were added to the solution and the solution digested at 37° C. for about 1 hour. After deproteinization with phenol-chloroform, precipitation was carried out with ethanol.

After cooling to $-70°$ C. for 15 minutes, the precipitate was collected by centrifugation and dissolved in 10 µl of TE (10 mM Tris-HCl, pH 7.5; 1 mM EDTA).

1 µl of the above sample solution was then added to a reaction solution (10 mM Tris-HCl, pH 7.5; 1 mM EDTA; and 100 mM NaCl), followed by addition of 10 ng of linker (purchased from PL-Pharmacia) bearing oligo dG. The resulting mixture was heated at 65° C. for 5 minutes and incubated at 42° C. for 30 minutes.

After cooling the reaction solution in ice water. 10 µl of 10-fold ligase buffer solution (10 mM ATP; 660 mM Tris-HCl, pH 7.5; 66mM $MgCl_2$; and 100 mM DTT), 78 µl of distilled water and 8 units of T4 DNA ligase were added to the solution and the reaction mixture incubated at 12° C. overnight.

Then, to the thus prepared mixture, 10 µl of 1M KCl, 1 unit of ribonuclease H, 33 units of DNA polymerase I, 4 units of T4 DNA ligase, 0.5 µl of nucleotide solution (20 mM dATP, 20 mM dGTP, 20 mM dCTP and 20 mM dTTP) and 0.1 µl of 50 µg/µl bovine serum albumin (BSA) were added and the mixture incubated at 12° C. for 1 hour and then at 25° C. for 1 hour.

After diluting the reaction solution 5-fold, E. coli strain RR1 was transformed according to the method of Hanahan [Hanahan, D; J Mol Biol 166, 557 (1983)] to prepare a human pancreatic cDNA bank.

(3) Selection of transformed bacteria containing human pancreatic elastase IIB cDNA The DNA from 4.700 clones of the human pancreatic cDNA bank was fixed onto nitrocellulose filter according to the method of Grunstein, M and Hogness, D S [Proc Natl Acad Sci, USA, 72, 3961 (1975)].

In order to select a clone including a plasmid containing human pancreatic elastase IIB cDNA, a rat pancreatic elastase II cDNA fragment was employed as a probe. The rat pancreatic elastase II cDNA was obtained by the following method. Firstly, a cDNA bank was prepared using mRNA extracted from rat pancreas. Then, an oligodeoxynucleotide 5'd(GGCATAGT-CCACAACCA)3' comprising 17 bases was synthesized complementary to a part of the known base sequence of rat pancreatic elastase II mRNA [MacDonald, R et al: Biochem, 21, 1453 (1982)]. The oligodeoxynucleotide corresponds to the amino acid sequence from amino acid 151 to amino acid 156 of the rat pancreatic elastase II. The 5'-end of the oligodeoxynucleotide was labelled with $^{32}$P by the method of Maxam, A M and Gilbert, W [Proc Natl Acad Sci, USA 74, 560 (1977)] to give a probe. Using the probe, a rat pancreatic elastase II cDNA clone was selected from the rat pancreatic cDNA bank. Then a fragment containing 200 bases was excised from the rat pancreatic elastase II cDNA with restriction endonucleases AatII and HindIII and labelled with $^{32}$P according to the nick translation method [Rigby, P W et al: J Mol Biol 3, 237 (1977)]. The DNA fragment was then used as a probe for hybridization with the DNA fixed on the nitrocellulose filter, according to the method of Alwine, S C et al [Proc Natl Acad Sci, USA 74, 5350 (1977)].

8 clones reactive with the probe were identified by autoradiography. A plasmid from one of the strains was named "pH2E8".

Figure 6:
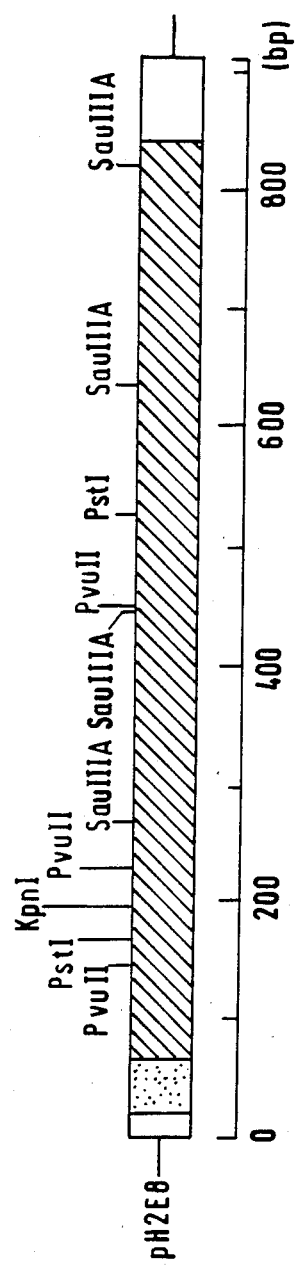
FIG. 6 is a restriction endonuclease cleavage map of part of plasmid pH2E8 obtained in Example 2, wherein the stippled portion indicates the section coding a peptide considered to be the signal peptide, and the striped portion indicates the section coding the mature elastase protein.

The restriction endonuclease cleavage map of the DNA inserted in pH2E8 was determined and is shown in FIG. 6. The base sequence was determined and is of the formula

```
(5')-C TTA CAG AAC TCC
CAC GGA CAC ACC ATG ATT AGG ACC CTG CTG
CTG TCC ACT TTG GTG GCT GGA GCC CTC AGT
TGT GGG GTC TCC ACT TAC GCG CCT GAT ATG
TAG ATG CTT GGA GGT GAA GAA GCG AGG
CCC AAC AGC TGG CCC TGG CAG GTC TCC CTG
CAG TAC AGC TCC AAT GGC CAG TGG TAC CAC
ACC TGC GGA GGG TCC CTG ATA GCC AAC AGC
TGG GTC CTG ACG GCT GCC CAC TGC ATC AGC
TCC TCC AGG ATC TAC CGC GTG ATG CTG GGC
CAG CAT AAC CTC TAC GTT GCA GAG TCC GGC
TCG CTG GCC GTC AGT GTC TCT AAG ATT GTG
GTG CAC AAG GAC TGG AAC TCC AAC CAG GTC
TCC AAA GGG AAC GAC ATT GCC CTG CTC AAA
CTG GCT AAC CCC GTC TCC CTC ACC GAC AAG
```

-continued

```
ATC CAG CTG GCC TGC CTC CCT CCT GCC GGC
ACC ATT CTA CCC AAC AAC TAC CCC TGC TAC
GTC ACA GGC TGG GGA AGG CTG CAG ACC AAC
GGG GCT CTC CCT GAT GAC CTG AAG CAG GGC
CGG TTG CTG GTT GTG GAC TAT GCC ACC TGC
TCC AGC TCT GGC TGG TGG GGC AGC ACC GTG
AAG ACG AAT ATG ATC TGT GCT GGG GGT GAT
GGC GTG ATA TGC ACC TGC AAC GGA GAC TCC
GGT GGG CCG CTG AAC TGT CAG GCA TCT GAC
GGC CGG TGG GAG GTG CAT GGC ATC GGC AGC
CTC ACG TCG GTC CTT GGT TGC AAC TAC TAC
TAC AAG CCC TCC ATC TTC ACG CGG GTC TCC
AAC TAC AAC GAC TGG ATC AAT TCG GTG ATT
GCA AAT AAC TAA CCA AAA GAA GTC CCT GGG
ACT GTT TCA GAC TTG GAA AGG TCA CAG AAG
GAA AAT AAT ATT ATA TAA AGT GAC AAC TAT
GCA AAT CAC -(3')
```

Beginning at the underlined ATG triplet, the encoded amino acid sequence is of the formula:

```
(N)- Met Ile Arg Thr Leu Leu
Leu Ser Thr Leu Val Ala Gly Ala Leu Ser
Cys Gly Val Ser Thr Tyr Ala Pro Asp Met
Ser Arg Met Leu Gly Gly Glu Glu Ala Arg
Pro Asn Ser Trp Pro Trp Gln Val Ser Leu
Gln Tyr Ser Ser Asn Gly Gln Trp Tyr His
Thr Cys Gly Gly Ser Leu Ile Ala Asn Ser
Trp Val Leu Thr Ala Ala His Cys Ile Ser
Ser Ser Arg Ile Tyr Arg Val Met Leu Gly
Gln His Asn Leu Tyr Val Ala Glu Ser Gly
Ser Leu Ala Val Ser Val Ser Lys Ile Val
Val His Lys Asp Trp Asn Ser Asn Gln Val
Ser Lys Gly Asn Asp Ile Ala Leu Leu Lys
Leu Ala Asn Pro Val Ser Leu Thr Asp Lys
Ile Gln Leu Ala Cys Leu Pro Pro Ala Gly
Thr Ile Leu Pro Asn Asn Tyr Pro Cys Tyr
Val Thr Gly Trp Gly Arg Leu Gln Thr Asn
Gly Ala Leu Pro Asp Asp Leu Lys Gln Gly
Arg Leu Leu Val Val Asp Tyr Ala Thr Cys
Ser Ser Ser Gly Trp Trp Gly Ser Thr Val
Lys Thr Asn Met Ile Cys Ala Gly Gly Asp
Gly Val Ile Cys Thr Cys Asn Gly Asp Ser
Gly Gly Pro Leu Asn Cys Gln Ala Ser Asp
Gly Arg Trp Glu Val His Gly Ile Gly Ser
Leu Thr Ser Val Leu Gly Cys Asn Tyr Tyr
Tyr Lys Pro Ser Ile Phe Thr Arg Val Ser
Asn Tyr Asn Asp Trp Ile Asn Ser Val Ile
Ala Asn Asn - (C)
```

It can be seen that plasmid pH2E8 had a region coding for a signal peptide comprising 16 amino acids and a region coding for the mature elastase protein termed elastase IIB. The elastase IIB comprises 253 amino acids. Plasmid pH2E8 also contains 5' and 3' non-translated regions.

There is as much as 77% homology between the amino acid sequence coded by the DNA insertion of plasmid pH2E8, and that of rat pancreatic elastase II reported by MacDonald, R J et al [Biochem, 21, 1453 (1982()].

Accordingly, plasmid pH2E8 is believed to contain cDNA coding a human pancreatic elastase II. With regard to the known sequence for human pancreatic elastase II, the 6 amino acid residue at the N-terminal of pH2E2 coding protein is clearly different to that of the human pancreatic elastase II reported by Largman, C, et al Biochim BioPhys Acta 623, 208 (1980)]. Thus the human pancreatic elastase IIB appears to be a novel protein.

Since pH2E8 contains an entire DNA coding for human pancreatic elastase IIB, it is possible to produce large amounts of the elastase IIB by transferring the cDNA to an appropriate expression vector and using, for example, E. coli, B. subtilis, yeast or mammalian cells as the host.

(4) Production of human pancreatic elastase IIB using mammalian cells

Construction of expression plasmid pSV2-E2B

Figure 7:
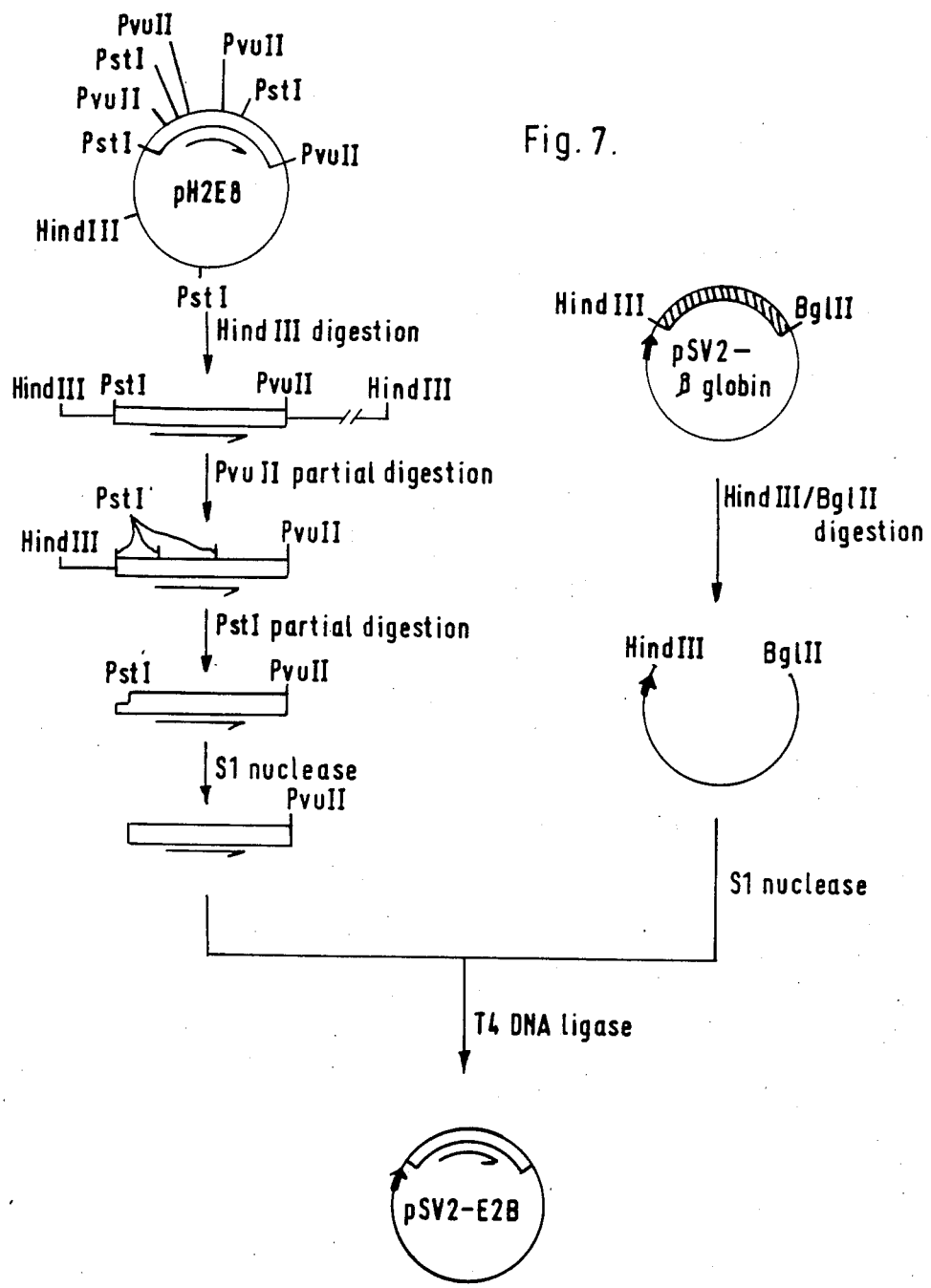
FIG. 7 illustrates the construction of plasmid pSV2-E2B in Example 2.

In order to produce human elastase IIB using mammalian cells as host, the cDNA was ligated to an expresion vector according to the procedure indicated in FIG. 7. The known pSV2 plasmid containing the SV40 promoter, enhancer, poly(A) signal and introns of the Small T antigen gene was used for construction of the expression vector. pSV2-β-globin is a plasmid based on the pSV2 vector with inserted β-globin cDNA. plasmid pH2E8 is the plasmid with inserted human elastase IIB cDNA. The reactions with S1 nuclease, etc, were carried out according to the methods described in "Molecular Cloning" [Maniatis, T et al (ed) "Molecular Cloning" Cold Spring Harbor Lab (1982)]. The broad arrows in FIG. 7 represent the promoter derived from SV40, and the narrow arrows show the direction of transcription.

From analysis of the restriction endonuclease digestion pattern, an expression plasmid (pSV2-E2B) was selected in which vector and cDNA were ligated in the correct orientation for transcription.

Transfection of COS 1 cells with expression plasmid pSV2-E2B

The constructed expression plasmid pSV2-E2B was transfected into COS 1 (mammalian cells) by the calcium phosphate method described in the literature [Graham and Van der Eb: Virology 52 456 (1973)].

Thus, $1 \times 10^6$ of COS 1 cells were sprayed on petri dishes (10 cm in diameter), and cultured overnight on Dulbecco-modified Eagle medium containing 10% fetal calf serum.

Plasmid pSV2-E2B (300 μg) was suspended in sterile distilled water (12.55 ml), then 2.5M $CaCl_2$ (0.75 ml) was added and the suspension mixed thoroughly. A pipette was used to bubble air through the system in order to maintain agitation, and 1.5 ml of 10×HeBS solution (HEPES, 210 mM: NaCl, 1.37M; KCl 4.7 mM; Na 10.6 mM; glucose, 55.5 mM; pH 7.05) was dropped into the resulting solution to precipitate the DNA and calcium phosphate.

The precipitate was allowed to stand at room temperature for 30 minutes to mature the precipitate, and 1 ml of the solution for each petri dish was added to the COS 1 cells cultured in fresh medium containing 10% fetal calf serum.

After cultivation of these cells for 12 hours at 37° C. in the presence of 5% $CO_2$. the culture medium was discarded in favour of a fresh, Dulbecco-modified Eagle medium containing no fetal calf serum. The cells were cultured for a further 48 hours at 37° C. in the presence of 5% $CO_2$. The transfected COS 1 cells obtained by this procedure were tested to detect the presence of human elastase IIB mRNA, while the supernatent of the culture medium was tested for elastase activity.

Extraction of mRNA from COS 1 cells

In order to confirm the existence of human elastase IIB mRNA transcribed from the expression plasmid in the transfected COS 1 cells, mRNA was extracted from the COS 1 cells and assayed by the Northern blot hybridization according to the following procedure.

After cultivation of the COS 1 cells for 48 hours, 1 ml of guanidine thiocyanate solution (4M guanidine thiocyanate; 1% Sarcosyl; 20 mM EDTA; 25 mM sodium citrate, pH 7.0; 100 mM 2-mercaptoethanol; 0.1% Antifoam A) was added to each petri dish in order to lyse the cells.

High molecular DNA molecules were degraded to low molecular ones by passing the solution several times through a 21 guage injection needle. The resultant solution was layered on a solution containing 5.7M cesium chloride and 0.1M EDTA, and the layered centrifuged at 20° C., 30,000 rpm for 17 hours using a Hitachi RPS 40 swing rotor. The resultant RNA precipitate was washed with a small amount of ethanol and dissolved in distilled water (300 μl).

According to the method of Aviv and Leder [Proc Natl Acad Sci. USA 69, 1408 (1972)], the extracted total RNA was purified on an oligo(dT) cellulose column to give several μg of purified mRNA. Half of the purified mRNA was used for Northern blot hydridization by the Thomas method [Proc Natl Acad Sci, USA 77 5201 (1980)]. $^{32}$P-Labelled human elastase IIB cDNA was used as a probe by the nick translation method [Rigby, P W et al: J Mol Biol 113, 237 (1977)]. A major band at about 1.8 Kb and a minor band at about 1.0 Kb which hydridized with the probe were detected only in the mRNA of COS 1 cells transfected with plasmid pSV2-E2B. It Was assumed that in the transcription of the plasmid pSV2-E2B, the 1.8 Kb mRNA is formed on termination of transcription at the poly(A) signal contained in the vector, while the 1.0 Kb mRNA is formed on termination of transcription at the poly(A) signal in the cDNA. The results from the Northern blot hybidization coincided with these assumptions.

The results thus show that using SV40 promoter in COS 1 cells, the plasmid pSV2-E2B can synthesize large guantities of human elastase IIB mRNA.

Elastase activity in suoernatant of the culture broth

Since the human elastase IIB cDNA in pSV2-E2B has a signal peptide region, secretion of expressed elastase into the medium as a proelastase was expected. Elastase activity in the medium after 48 hours cultivation was accordingly determined. Tris-HCl buffer solution (pH 8.0) was added to the supernatant of the culture medium (1 ml) to a final concentration of 0.2M, 10 mg/ml trypsin (50 μl) was added, and an activation treatment of the proelastase was carried out for 15 minutes at 25° C. Next, 50 μl of soybean trypsin inhibitor solution (10 mg/ml) and a synthetic substrate, glutaryl-Ala-Ala-Pro-Leu-P-nitroanilide were added, and the enzyme reaction was carried out by incubation at 25° C. After completion of the reaction, liberated P-nitroanilide was determined by measuring absorbance at 410 nm.

The elastase activity in the culture medium of COS 1 cells transfected with pSV2-E2B was distinctly detected, and the production of active human elastase IIB in COS 1 cells was found.

The activation treatment with trypsin or other activator was indispensable.

The production of human elastase IIB in COS 1 cells transfected with plasmid pSV2-E2B was transient. However, if plasmid pSV2-E2B is linked with a suitable selection marker (for example, the neo gene, dihydrofolate reductase gene, or other resistance marker) and is transfected in to CHO or other cells, a cell line suitable for sustained production of human elastase IIB can be prepared.

(5) Production of human pancreatic elastase IIB using *Bacillus subtilis*

Construction of expression vector pBSEX-E2B

Figure 8:
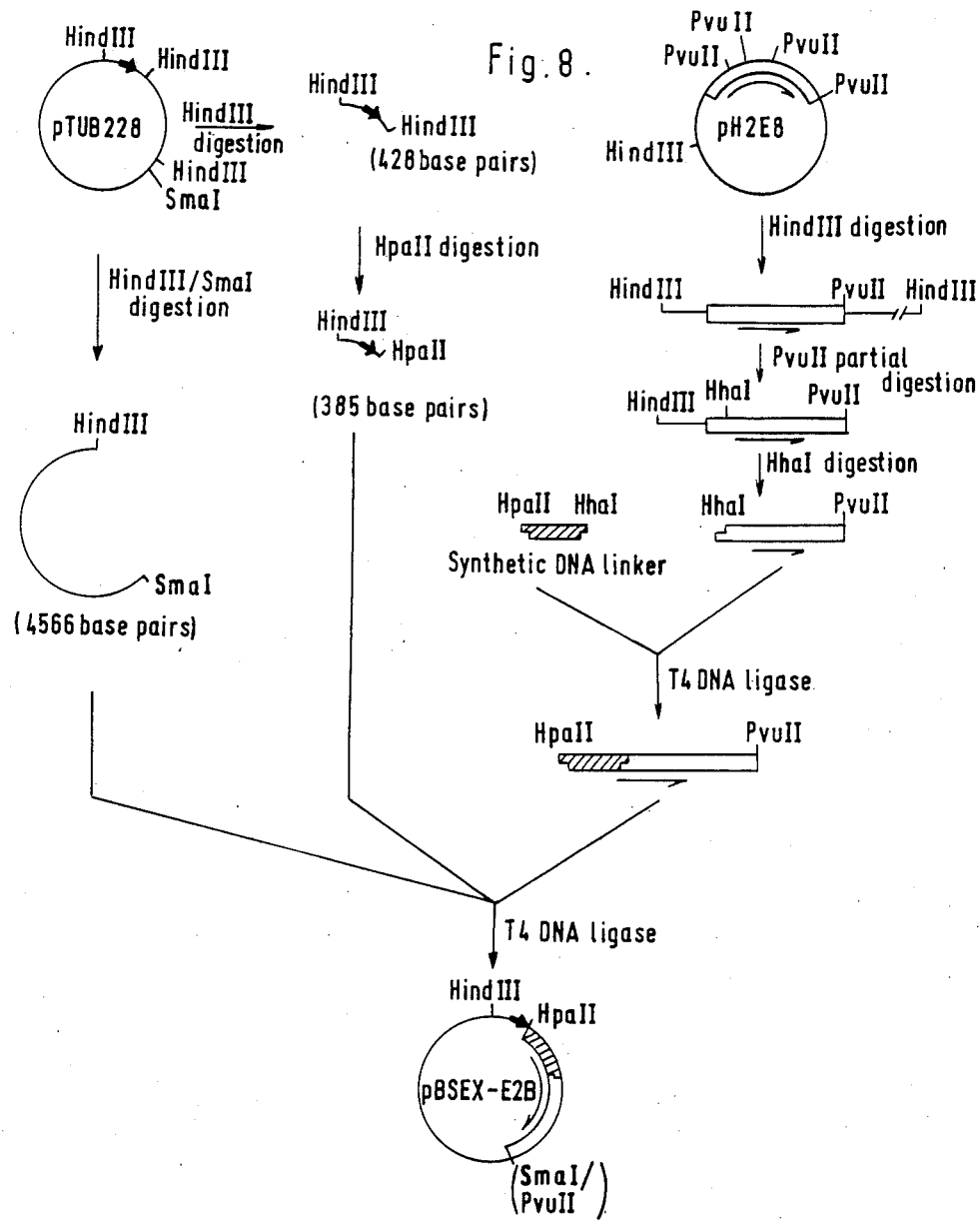
FIG. 8 illustrates the construction of plasmid pBSEX-E2B in Example 2.

The construction method for the expression vector is illustrated in FIG. 8. plasmid pH2E8 containing human elastase IIB cDNA was digested with restriction endonuclease HindIII to a linear DNA, and then partially digested with restriction enzyme PvuII. A DNA fragment of about 1.3 Kb containing the elastase IIB cDNA was isolated. This fragment was partially digested with restriction endonuclease HhaI to give a fragment containing cDNA coding for the amino acid sequence beginning from the eighth amino acid counted from the N-terminal end of the elastase IIB activation peptide. The specific oligonucleotide sequence shown in FIG. 9 was synthesized. This sequence codes for part of the signal peptide of *B. subtilis* α-amylase, and seven amino acids at the N-terminal end of the elastase IIB activation peptide. The fragments were ligated with T4 DNA ligase.

On the other hand, plasmid pTUB228 [Ohmura, K et al: J Biochem 95 87 (1984)] containing the α-amylase gene of *Bacillus subtilis* was digested with restriction endonuclease HindIII to isolate a DNA fragment of 428 base pairs containing the α-amylase promoter and a part of the signal peptide, and separately a DNA fragment of 5,100 base pairs containing the replication origin. The DNA fragment of 428 base pairs and the DNA fragment of 5,100 base pairs were further digested with restriction endonuclease HPaII and SmaI, respectively, to give DNA fragments of 385 base pairs and of 4566 base pairs.

The three DNA fragments were ligated with T4 DNA ligase, and incorporated into protoplasts of *Bacillus subtilis* 207-25 strain ($m_{168}^-$ hsrM recE4 amyEO7 aroI906 leuA8 lys21; derived from Marburg strain) according to conventional procedures. After regeneration, cultivation on a medium containing 10 μg/ml of kanamycin allowed selection of the transformed strains which could grow on this medium. Selection of the desired plasmid was achieved through colony hybridization using as probe the synthetic oligonucleotide of FIG. 9. A positive clone was identified and the plasmid shown to be the intended one by determination of the base sequence.

The expression plasmid obtained in this manner was designated plasmid pBSEX-E2B.

Elastase activity in supernatant of culture broth

*Bacillus subtilis* 207-25 strain transformed with the human elastase IIB expression plasmid pBSEX-E2B was cultured on a reciprocal shaker in 1 1 of LG medium (1% Bacto trypton, Difco; 0.5% yeast extract, Difco; 0.5% NaCl; 0.2% glucose; pH 7.0) containing 50 μg/ml of kanamycin. The culturing was performed at 35° C. for 48 hours.

After completion of the culture, the culture medium was cooled to 4° C. and centrifuged at 3000×G for 5 minutes, and the cells discarded. Ammonium sulfate was added to the supernatant to 55% saturation, and the solution was stirred at 4° C. for 12 hours. Insoluble material formed in this treatment was precipitated by centrifugation at 8000×G for 20 minutes, the supernatant was discarded, and the precipitate was dissolved in 20 ml of 0.2M Tris-HCl buffer solution (pH 8.0) This solution was dialyzed against 1 l of 0.2M Tris-HCl buffer solution (pH 8.0) for 16 hours, and insoluble material was removed by centrifugation at 8000×G for 20 minutes. The dialyzed lnner solution was taken as a crude elastase IIB sample solution, and the activity was determined by the following procedure.

Determination of Elastase Activity in the Sample Solution

Proelastase was activated by trypsin treatment of the sample solution, and allowed to react at 25° C. with a synthetic substrate, glutaryl-Ala-Ala-Pro-Leu-P-nitroanilide. Liberated P-nitroanilide was determined by measuring absorbance at 410 nm. Since elastase activity was distinctly detected in the sample solution from the 207-25 strain transformed with pBSEX-E2B, the production of active human elastase IIA in *Bacillus subtilis* was demonstrated.

(6) Production of human oancreatic elastase IIB using *Escherichia coli*

Various different promoters may be used, including for instance the tryptophan (trp) promoter, lactose (lac) promoter, tryptophan-lactose (tac) promoter, lipoprotein (lpp) promoter, lambda (λ) $P_L$ promoter derived from bacteriophage, or polypeptide chain elongation factor (tuf B) promoter. An example with the lactose promoter is as follows.

Figure 10:
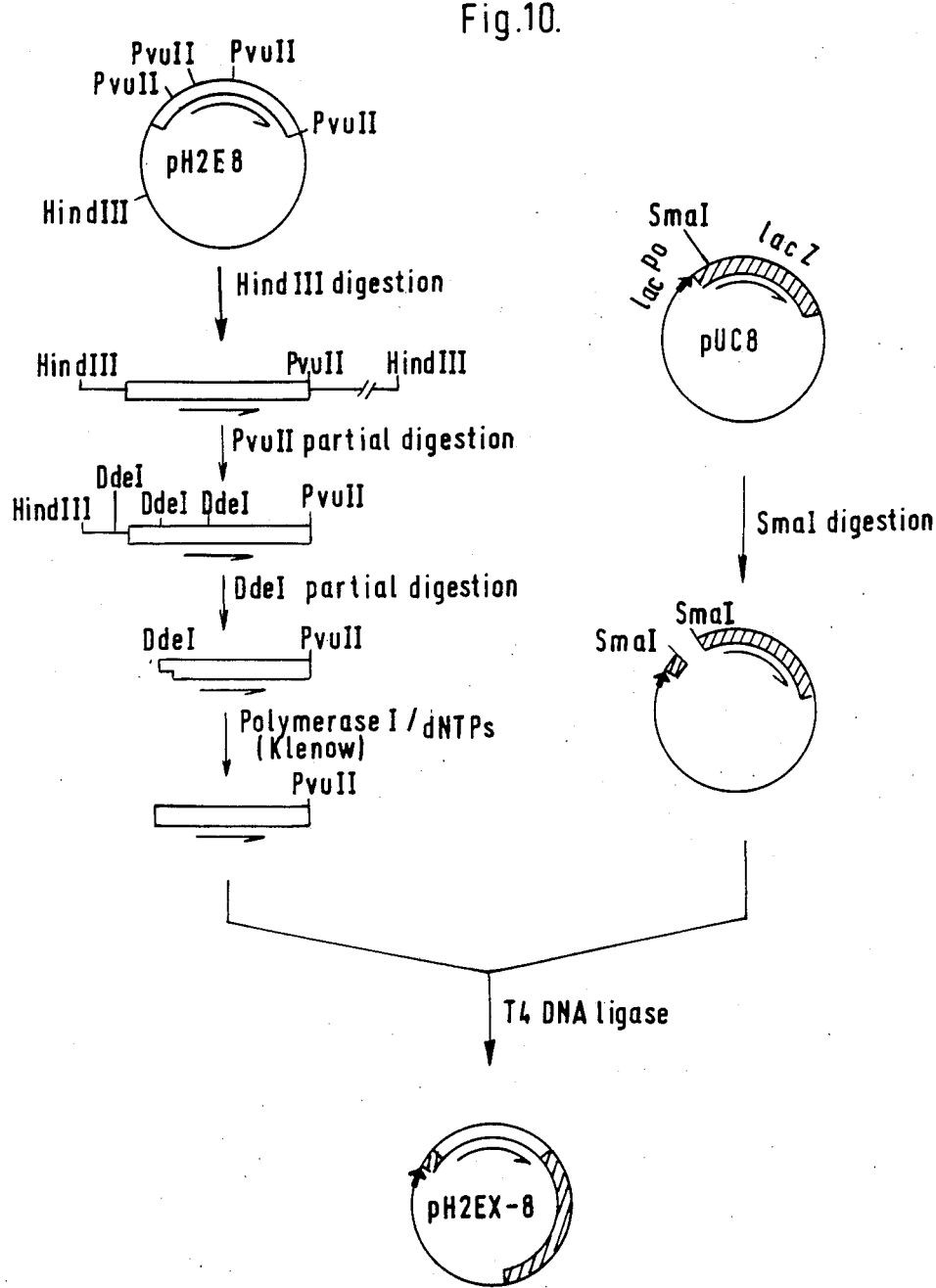
FIG. 10 illustrates the construction of plasmid pH2EX-8 in Example 2. The striped area represents the β-galactosidase gene. Broad arrows indicate the lactose promoter and operator, and narrow arrows show the direction of transcription.

As shown in FIG. 10, plasmid pH2E8 containing human elastase IIB cDNA was digested with restriction endonuclease HindIII to form a linear DNA, and then partially digested with restriction enzyme PvuII to isolate a DNA fragment of about 1.3 Kb containing elastase IIB cDNA.

This fragment was partially digested with restriction endonuclease DdeI to give a fragment containing cDNA coding for an amino acid sequence down stream from the activation peptide of elastase IIB. By treatment of this DNA fragment with DNA Polymerase Klenow fragment and four kinds of deoxyribonucleoside 5'-triphosphates (dATP, dCTP, dGTP, dTTP), both ends were converted to blunt ends. The resultant DNA fragment was inserted into the SmaI site of plasmid pUC8.

*Escherichia coli* strain JM103 was transformed with the plasmid. plasmid was extracted from several transformed strains, and through the use of restriction endonuclease mapping, plasmid with the same orientation of cDNA transcription and of the promoter for the lactose operon was selected. This elastase IIB expression plasmid was designated as pH2EX-8.

The base sequence and corresponding amino acid sequence for around the 5'-end of the elastase cDNA in pH2EX-2 are as follows.

and six amino acids derived from β-galactosidase combine at the N-terminal.

Several *Escherichia coli* strains were transformed with pH2EX-8 to give strains capable of producing human elastase IIB. The strains containing expression plasmid were inoculated in 2×TY-ampicillin medium (1.6% Bacto trypton; 1% yeast extract; 0.5% NaCl; hours. After completion of the culture, cell suspension was harvested by centrifugation of the culture medium, 2.4×10⁸ cells were suspended in 15 μl of SDS solution (2% SDS, 5% 2-mercaptoethanol; 10% glycerin; 60 mM Tris-HCl, pH 6.8). The cell suspension was heated at 100° C. for 3 minutes, and protein was analyzed by SDS polyacrylamide gel electrophoresis, according to the method of Laemmli et al [Nature, 227 680 (1970)].

As a result, a large quantity of elastase production was found in strain YA21. The production yield of elastase fusion protein was 20% of the total protein produced by the YA21 strain. Though a considerable production of elastase fusion protein in χ984 strain Was observed, the production yield was less than half that in the YA21 strain. The production yields in two other *Escherichia coli* strains (HB101 and MC4100 strains) were low.

Since the elastase fusion protein forms inclusion bodies in cells, purification was comparatively easy. Thus, from 1 l of a culture medium of YA21 strain transformed with plasmid pH2EX-8, 6.5 g of cells forming inclusion bodies could be obtained. The obtained cells (6.5 g) were lysed in 50 mM Tris-HCl buffer solution (pH 8.0) containing 0.2 mg/ml lysozyme and 1 mg/ml deoxycholic acid. Intact cells were removed by low speed centrifugation (1,500×G, 10 minutes) and inclusion bodies were recovered as a precipitate by high speed centrifugation (11,000×G, 20 minutes). Since the precipitate still contained much cell debris, the precipitate was suspended in 50 mM Tris-HCl buffer solution containing 5 mg/ml octylphenoxy polyethoxyethanol surfactant (Triton X-100, Trade Mark) and washed by high speed centrifugation (11,000×G, 20minutes). A washed pellet of inclusion bodies was suspended in a small amount of Tris-HCl buffer solution and stored at 4° C.

The purified inclusion body (300 mg) containing about 50% elastase IIB fusion protein could be obtained by this procedure. The inclusion body produced by YA21 strain transformed with pH2EX-8 was shown to contain the elastase fusion protein by immuno-blotting.

Though most of the elastase produced by *Escherichia coli* is in the insoluble fraction of the cells as inclusion bodies, a smaller proportion exists in a soluble state and retains enzym activity. Determination of the enzyme activity was carried out as follows. The strain χ984 strain transformed with plasmid pH2EX-8 was cultured with shaking in 1 l of 2 x TY-ampicillin medium at 37° C. for 15 hours. After completion of the culturing, the cells were harvested by centrifugation at 3000×G for 5

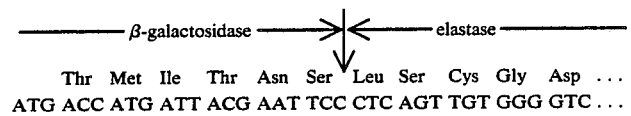

Thr Met Ile Thr Asn Ser Leu Ser Cys Gly Asp ...
ATG ACC ATG ATT ACG AAT TCC CTC AGT TGT GGG GTC ...

Therefore, the human elastase IIB expressed by pH2EX-8 is shown to be a fusion protein in which two amino acids (Leu, Ser) derived from the signal peptide minutes and suspended in 20 ml of buffer solution A (50 mM Tris-HCl, pH 8.0; 1 mM EDTA; 50 mM NaCl). 10 mg of lyzozyme was added, and the supension incubated at 5° C. for 20minutes. Deoxycholic acid to a final concentration of 1 mg/ml was added to the resultant suspension which was then incubated at 20° C. Deoxyribonuclease to a final concentration of 0.1 mg/ml was added, and the cells were disrupted in a polytron homogenizer. After removal of the cell debris by centrifugation at 80,000×G, 40 minutes, the lysate was subjected to column chromatography on high molecular weight, cross-linked dextran (Sephadex G-75). The fractions having elastase activity were purified by antibody affinity chromatography, and used for the following determination of elastase activity. proelastase was activated by trypsin treatment of the sample solution Next, P-nitroanilide liberated by the reaction with a synthetic substrate glutaryl-Ala-Ala-Pro-Leu-P-nitroanilide, was determined by measuring the absorbance at 410 nm. The reaction was carried out by incubation at 25° C. in 0.2M Tris-HCl buffer solution (pH 8.0) containing the synthetic substrate. As a result, elastase activity was distinctly detected in the sample solution of χ984 strain transformed with plasmid pH2EX-8, and therefore the production of active human elastase IIB in *E. coli* was demonstrated.

(7) production of human pancreatic elastase IIB using yeast

In the case of yeast as a host (and as with a *Escherichia coli, Bacillus subtilis* or mammalian cells), human pancreatic elastase IIB cDNA could be ligated to a suitable expression vector using known techniques, introduced into the host cells and expressed Elastase activity in the culture medium was confirmed Saccharomyces cerevisiae described in "Japanese Guidelines for Recombinant DNA Research" may be used as host, but S288C strain and other strains are practically suitable. On the other hand, YEp13 and other vectors were appropriate as a vector. As promoter, the ADHI gene coding for alcohol dehydrogenase gene, and other promoters, are suitable.

EXAMPLE 3:

Elastase IIIA (1) Separation of mRNA from human pancreas

Human pancreas (autopsy sample) weighing 5.5 g was homogenised and denatured in a homogeniser (a polytron homogeniser from Kinematica GmbH, Germany, Polytron being a Trade Mark) in an adequate amount of guanidine thiocyanate solution (4M guanidine thiocyanate; 1% detergent, Sarcosyl from Sigma Chemical Co, USA; 20 mM ethylenediaminetetraacetic acid (EDTA); 25 mM sodium citrate, pH 7.0; 100 mM 2-mercaptoethanol and 0.1% antifoaming agent, Antifoam A from Sigma Chemical Co USA), followed by centrifugation. to obtain a supernatant.

One volume of supernatant was added to 0.025 volumes of 1M acetic acid and 0.75 volumes of ethanol, and the mixture cooled to −20° C. for several hours, followed by centrifugation, to obtain a precipitate. The precipitate was suspended in a guanidine hydrochloride solution (7.5M guanidine hydrochloride; 25 mM sodium citrate, pH 7.0; and 5 mM dithiothreitol, DTT). To 1 volume of the suspension was added 0.025 volumes of 1M acetic acid and 0.5 volumes of ethanol, and the resultant mix cooled to −20° C. for several hours, followed by centrifugation. The resultant precipitate was suspended again in more of the guanidine hydrochloride solution, mixed as before with acetic acid and ethanol, cooled to −20° C. and centrifuged, followed by collection of the precipitate. Next, the precipitate was washed several times with ethanol to remove guanidine hydrochloride, and then dissolved in distilled water followed by precipitation of the RNA with ethanol. The precipitate was collected by centrifugation to give 53.9 mg of RNA.

The RNA thus obtained was adsorbed onto an oligo(dT) cellulose column in a high concentration salt solution (0.5M NaCl; 20 mM Tris-HCl, pH 7.5; 1 mM EDTA; and 0.1% sodium dodecyl sulfate, SDS). and the mRNA-containing poly(A) was eluted with an elution buffer (10 mM Tris-HCl, pH 7.5; 1 mM EDTA; and 0.05% SDS) to give 255 µg of mRNA.

(2) Preparation of cDNA bank

The preparation of a cDNA bank was carried out according to the Okayama-Berg method. 5 µg of the mRNA and 24 units of a reverse transcriptase were incubated at 42° C. for 60 minutes in 20 µl of a reaction solution (50 mM of Tris-HCl, pH 8.3; 8 mM of $MgCl_2$; 30 mM of KCl; 0.3 mM of DTT; 2 mM each of dATP, dGTP, dCTP and dTTP; 10 µCi of α-$^{32}$P-dCTP: and 1.4 µg of vector primer DNA, purchased from PL-Pharmacia).

The reaction was stopped by the addition of 2 µl of 0.25M EDTA and 1 µl of 10% SDS. Deproteinization was carried out with 20 µl of phenol-chloroform. After centrifugation of the reaction mixture. the aqueous layer was collected. 20 µl of 4M ammonium acetate and 80 µl of ethanol were added to the aqueous layer and the mixture cooled to −70° C. for 15 minutes. The precipitate was then collected by centrifugation and washed with 75% aqueous ethanol and dried under reduced pressure.

The resultant precipitate was dissolved in 15 µl of terminal transferase reaction solution (140 mM potassium cacodylate, of formula $C_2H_6AsKO_2$; 30 mM Tris-HCl, pH.h 6.8; 1 mM cobalt chloride; 0.5 mM DTT; 0.2 µg of poly(A); and 100 mM of dCTP). After incubating the solution at 37° C. for 3 minutes, 18 units of terminal deoxynucleotidyl transferase were added and allowed to react for 5 minutes.

The above reaction was stopped by addition of 1 µl of 0.25M EDTA and 0.5 µl of 10% SDS. Deproteinization was then carried out with phenol-chloroform. After centrifugation of the reaction mixture, the aqueous layer was collected. 15 µl of 4M ammonium acetate and 60 µl of ethanol were added to the aqueous layer and mixed well. After cooling the mixture to −70° C. for 15 minutes, the precipitate was collected by centrifugation.

The precipitate was dissolved in a buffer for restriction endonuclease (50 mM NaCl; 10 mM Tris-HCl, pH 7.5; 10 mM $MgCl_2$; and 1 mM DTT). 2.5 units of the restriction enzyme HindIII were added to the solution and the solution incubated at 37° C. for about 1 hour. After deproteinization with phenol-chloroform, precipitation was carried out with ethanol.

After cooling to −70° C. for 15 minutes, the precipitate was collected by centrifugation and dissolved in 10 µl of TE (10 mM Tris-HCl, pH 7.5; 1 mM EDTA). 1 µl of the above sample solution was then added to a reaction solution (10 mM Tris-HCl, pH 7.5; 1 mM EDTA; and 100 mM NaCl), followed by addition of 10 ng of linker (purchased from PL-Pharmacia) bearing oligo dG. The resulting mixture was heated at 65° C. for 5 minutes and maintained at 42° C. for 30 minutes.

After cooling the reaction solution in ice water, 10 µl of 10-fold ligase buffer solution (10 mM ATP; 660 mM Tris-HCl, pH 7.5; 66mM MgCl$_2$; and 100 mM DTT), 78 μl of distilled water and 8 units of T4 DNA ligase were added to the solution and the reaction mixture maintained at 12° C. overnight.

Then, to the thus prepared mixture, 10 μl of 1M KCl. 1 unit of ribonuclease H, 33 units of DNA polymerase I, 4 units of T4 DNA ligase, 0.5 μl of nucleotide solution (20 mM dATP, 20 mM dGTP, 20 mM dCTP and 20 mM dTTP) and 0.1 μl of 50 μg/μl bovine serum albumin (BSA) were added and the mixture maintained at 12° C. for 1 hour and then at 25° C. for 1 hour.

After diluting the reaction solution 5-fold, E. coli strain RR1 was transformed according to the method of Hanahan [Hanahan, D; J Mol Biol 166, 557 (1983)] to prepare a human pancreatic cDNA bank.

(3) Selection of transformed bacteria containing human pancreactic elastase IIIA cDNA The DNA from 4,700 clones of the human pancreactic cDNA bank was fixed onto nitrocellulose filter according to the method of Grunstein, M and Hogness, D S [Proc Natl Acad Sci, USA, 72, 3961 (1975)].

A porcine pancreatic elastase I cDNA fragment was excised with restriction endonuclease PstI and labelled with $^{32}$P according to the nick translation method [Rigby, P W et al:J. Mol. Biol 113, 237 (1977)]. Using the DNA fragment as probe, it was hybridized with the DNA fixed on the filter at 35° C. in a solution of 40% formamide, 0.75M sodium chloride of 5-fold concentration and 0.075M sodium citrate, along with a solution of 0.1% BSA, 0.1% polysucrose (Ficoll, Trade Mark), 0.1% polyvinyl pyrrolidone, 0.5% SDS, 10 mM sodium phosphate and 100 μg/ml of salmon spermatozoon DNA.

7 microorganism strains wh:ch hybridized with the probe were identified by autoradiography. A plasmid from one of the strains was named pCL2, and the inserted cDNA was named CL2.

(4) The amino acid sequence and elastase IIIA coded by plasmid pCL2

In CL2, there exists only one open reading frame. This sequence codes for 270 amino acids. The encoded amino acid sequence showed some homology with trypsin and chymotrypsin, to a degree of only about 30%. However, there was a higher homology, 57%, with porcine pancreatic elastase I. There also existed an amino acid sequence (Gly-AsP-Ser-Gly-Gly-Pro) around the active center which is be commonly found in the sam region in serine proteases such as trypsin, chymotrypsin, etc. Further, there is a 45th histidine residue, 95th aspartic acid residue and 189th serine residue which can participate in the characteristic charge relay of serine proteases.

Moreover, the encoded amino acid sequence adjacent the carboxyl terminal, which in elastase forms a pocket for binding with the substrate is very similar between human elastase IIIA and the porcine elastase I. There is also an encoded 211th valine residue and 223rd threonine residue, which are characteristic of a substrate-binding pocket of the porcine elastase I.

The base sequence was of the formula (5')- ATC ATC ACA
AAA CTC ATG <u>ATG</u> CTC CGG CTG CTC AGT TCC
CTC CTC CTT GTG GCC GTT GCC TCA GGC TAT
GGC CCA CCT TCC TCT CAC TCT TCC AGC CGC
GTT GTC CAT GGT GAG GAT GCG GTC CCC TAC -continued AGC TGG CCC TGG CAG GTT TCC CTG CAG TAT
GAG AAA AGT GGA AGC TTC TAC CAC ACG TGT
GGC GGT AGC CTC ATC GCC CCC GAT TGG GTT
GTG ACT GCC GGC CAC TGC ATC TCG AGG GAT
CTG ACC TAC CAG GTG GTG TTG GGT GAG TAC
AAC CTT GCT GTG AAG GAG GGC CCC GAG CAG
GTG ATC CCC ATC AAC TCT GAG GAG CTG TTT
GTG CAT CCA CTC TGG AAC CGC TCG TGT GTG
GCC TGT GGC AAT GAC ATC GCC CTC ATC AAG
CTC TCA CGC AGC GCC CAG CTG GGA GAT GCC
GTC CAG CTC GCC TCA CTC CCT CCC GCT GGT
GAC ATC CTT CCC AAC AAG ACA CCC TGC TAC
ATC ACC GGC TGG GGC CGT CTC TAT ACC AAT
GGG CCA CTC CCA GAC AAG CTG CAG CAG GCC
CGG CTG CCC GTG GTG GAC TAT AAG CAC TGC
TCC AGG TGG AAC TGG TGG GGT TCC ACC GTG
AAG AAA ACC ATG GTG TGT GCT GGA GGG TAC
ATC CGC TCC GGC TGC AAC GGT GAC TCT GGA
GGA CCC CTC AAC TGC CCC ACA GAG GAT GGT
GGC TGG CAG GTC CAC GGT GTG ACC AGC TTT
GTT TCT GCC TTT GGC TGC AAC TTC ATC TGG
AAG CCC ACG GTG TTC ACT CGA GTC TCC GCC
TTC ATC GAC TGG ATT GAG GAG ACC ATA GCA
AGC CAC TAG AAC CAA GGC CCA GCT GGC AGT
GCT GAT CGA TCC CAC ATC CTG AAT AAA GAA
TAA AGA TCT CTC AGA AAA -(3')

Beginning with the underlined ATG triplet, the encoded amino acid sequence is of the formula:

(N)-Met Met Leu Arg Leu Leu Ser Ser
Leu Leu Leu Val Ala Val Ala Ser GLy Tyr
Gly Pro Pro Ser Ser His Ser Ser Ser Arg
Val Val His Gly Glu Asp Ala Val Pro Tyr
Ser Trp Pro Trp Gln Val Ser Leu Gln Tyr
Glu Lys Ser Gly Ser Phe Tyr His Thr Cys
Gly Gly Ser Leu Ile Ala Pro Asp Trp Val
Val Thr Ala Gly His Cys Ile Ser Arg Asp
Leu Thr Tyr Gln Val Val Leu Gly Glu Tyr
Asn Leu Ala Val Lys Glu Gly Pro Glu Gln
Val Ile Pro Ile Asn Ser Glu Glu Leu Phe
Val His Pro Leu Trp Asn Arg Ser Cys Val
Ala Cys Gly Asn Asp Ile Ala Leu Ile Lys
Leu Ser Arg Ser Ala Gln Leu Gly Asp Ala
Val Gln Leu Ala Ser Leu Pro Pro Ala Gly
Asp Ile Leu Pro Asn Lys Thr Pro Cys Tyr
Ile Thr Gly Trp Gly Arg Leu Tyr Thr Asn
Gly Pro Leu Pro Asp Lys Leu Gln Gln Ala
Arg Leu Pro Val Val Asp Tyr Lys His Cys
Ser Arg Trp Asn Trp Trp Gly Ser Thr Val
Lys Lys Thr Met Val Cys Ala Gly Gly Tyr
Ile Arg Ser Gly Cys Asn Gly Asp Ser Gly
Gly Pro Leu Asn Cys Pro Thr Glu Asp Gly
Gly Trp Gln Val His Gly Val Thr Ser Phe
Val Ser Ala Phe Gly Cys Asn Phe Ile Trp
Lys Pro Thr Val Phe Thr Arg Val Ser Ala
Phe Ile Asp Trp Ile Glu Glu Thr Ile Ala
Ser His -(C)

The amino acid sequence of the coded protein appears at a glance to be analogous with the amino acid composition of the human pancreatic elastase I reported by Largman et al [Largman, C et al: Biochemistry 15, 2491 (1976)], However, the present elastase Was clearly different in detail from the known one, and the molecular weights were also different. The isoelectric point calculated according to the amino acid sequence was in the range of 7.5 to 7.8. This value was similar to the isoelectric point of 7.6 of the human pancreatic proelastase I reported by Scheele, G et al [Scheele et al Gastroenterology 80, 461(1981)].

The active form of the human elastase may be produced by cleaving at the carboxy group of the 28th arginine residue (counted from the N-terminal) and retaining the longer. C-terminal portion. Cleaving can be effected for example with trypsin.

Since pCL2 contains an entire cDNA coding for human pancreatic elastase IIIA, it is possible to produce large amounts of the elastase IIIA by transferring the cDNA to an appropriate expression vector and using, for example, E. coli, B. subtilis, yeast or mammalian cells as the host.

(5) production of human oancreatic elastase IIIA using animal cells

Construction of expression plasmid pSV2-CL2

Figure 11:
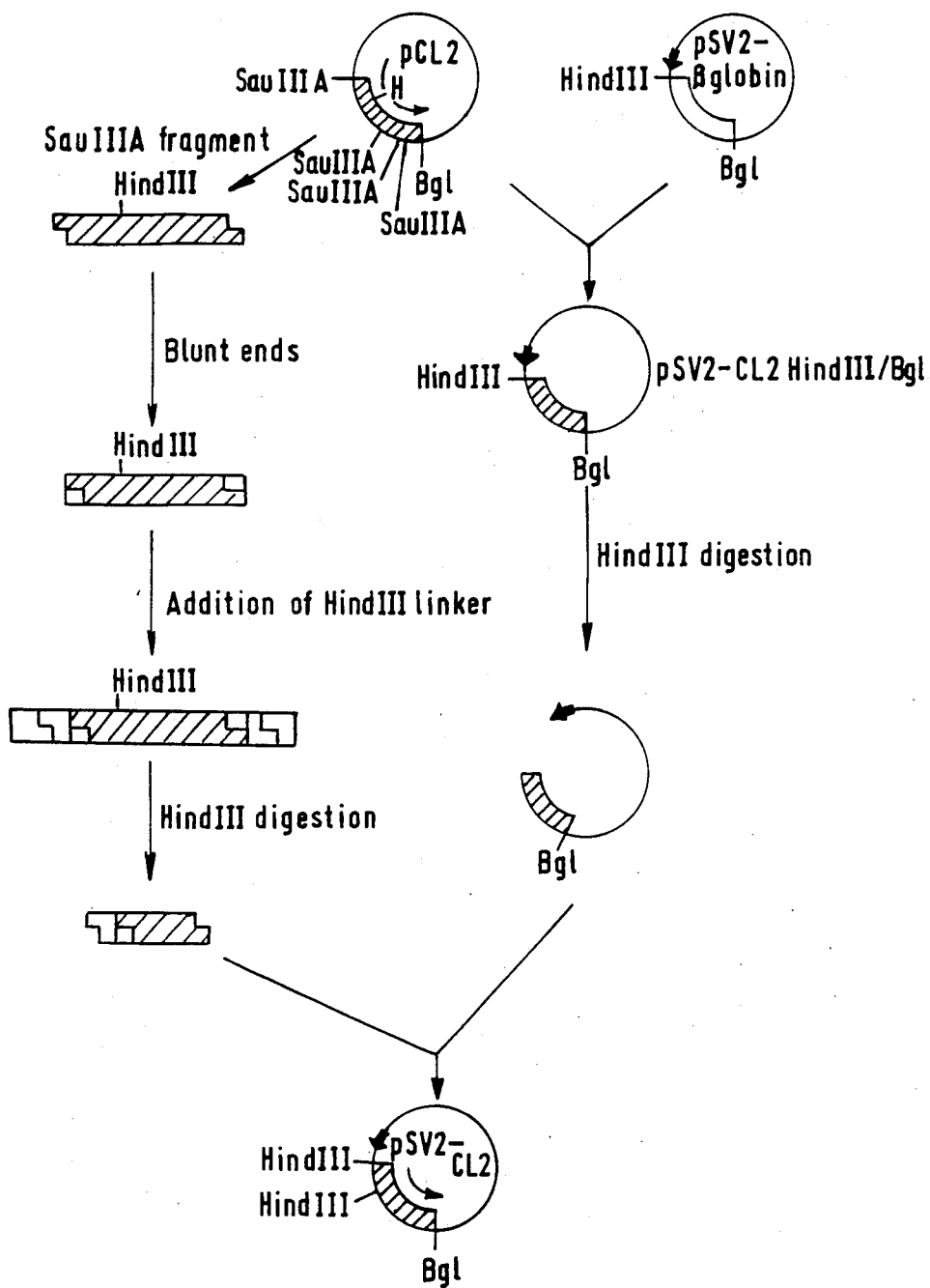
FIG. 11 illustrates the construction of plasmid pSV2-CL2 in Example 3.

In order to produce human elastase IIIA using mammalian cells as host, the cDNA was ligated to an expression vector according to the procedure indicated in FIG. 11. The known pSV2 plasmid containing the SV40 Small T antigen gene was used for construction of the expression vector. pSV2-$\beta$-globin is a plasmid based on the pSV2 vector with inserted $\beta$-globin cDNA. plasmid pCL2 is the plasmid with inserted human elastase IIIA cDNA. The reactions with S1 nuclease, etc, were carried out according to the methods described in "Molecular Cloning" [Maniatis, T et al (ed) "Molecular Cloning" Cold Spring Harbor Lab (1982)]. The broad arrows in FIG. 11 represent the promoter derived from SV40, and the narrow arrows show the direction of transcription.

From analysis of the restriction endonuclease cleavage pattern, an expression plasmid (pSV2-CL2) was selected which incorporated the desired fragments oriented in the correct sense for the transcription of the vector and cDNA.

Transfection of COS 1 cells with expression plasmid pSV2-CL2

The constructed expression plasmid pSV2-CL2 was transfected into COS 1 (mammalian cells) by the calcium phosphate method described in the literature [Graham and Van der Eb: Virology 52 456 (1973)].

Thus, $1 \times 10^6$ of COS 1 cells were seeded on petri dishes (10 cm in diameter), and cultured overnight on Dulbecco-modified Eagle medium containing 10% fetal calf serum.

Plasmid pSV2-CL2 (300 $\mu$g) was suspended in sterile distilled water (12.55 ml), then 2.5M $CaCl_2$ (0.75 ml) was added and the suspension mixed thoroughly. A pipette was used to bubble air through the system in order to maintain agitation, and 1.5 ml of $10 \times HeBS$ solution (HEPES, 210 mM; NaCl, 1.37M; KCl 4.7mM; $Na_2HPO_4$, 10.6 mM; glucose, 55.5 mM; pH 7.05) was dropped into the resulting solution to precipitate the DNA and calcium phosphate.

The precipitate was allowed to stand at room temperature for 30 minutes to mature the precipitate, and 1 ml of the solution for each petri dish was added to the COS 1 cells cultured in fresh medium containing 10% fetal calf serum.

After cultivation of these cells for 12 hours at 37° C. in the presence of 5% $CO_2$, the culture medium was discarded in favour of a fresh, Dulbecco-modified Eagle medium containing no fetal calf serum. The cells were cultured for a further 48 hours at 37° C. in the presence of 5% $CO_2$. The transfected COS 1 cells obtained by this procedure were tested to detect the presence of human elastase IIIA mRNA, while the supernatant of the culture medium was IesIed for elastase activity.

Extraction of mRNA from COS 1 cells

In order to confirm the existence of human elastase IIIA mRNA transcribed from the expression plasmid in the transfected COS 1 cells, mRNA was extracted from the COS 1 cells and assayed by the Northern blot hybridization according to the following procedure.

After cultivation of the COS 1 cells for 48 hours, 1 ml of guanidine thiocyanate solution (4M guanidine thiocyanate; 1% Sarcosyl; 20 mM EDTA; 25 mM sodium citrate. pH 7.0; 100 mM 2-mercaptoethanol; 0.1% Antifoam A) was added to each Petri dish in order to lyse the cells. High molecular DNA molecules were degraded to low molecular ones by passing the solution several times through a 21 guage injection needle. The resultant solution was layered on a solution containing 5.7M cesium chloride and 0.1M EDTA, and the solution centrifuged at 20° C., 30,000 rpm for 17 hours using a Hitachi RPS 40 swing rotor. The resultant RNA precipitate was washed with a small amount of ethanol and dissolved in distilled water (300 $\mu$l). 810 $\mu$g of total mRNA was isolated from about $10^8$ COS 1 cells.

According to the method of Aviv and Leder [Proc Natl Acad Sci, USA 69, 1408 (1972)], the extracted total RNA was purified on an oligo(dT) cellulose column to give several $\mu$g of purified mRNA. Half of the purified mRNA was used for Northern blot hydridization by the Thomas method [Proc Natl Acad Sci, USA 77 5201 (1980)]. $^{32}$P-Labelled human elastase IIIA cDNA was used as a probe by the nick translation method [Rigby, P W et al: J Mol Biol 113, 237 (1977)]. A major band at about 1.8 Kb and a minor band at about 1.0 Kb which hydridized with the probe were detected only in the mRNA of COS 1 cells transfected with plasmid pSV2-CL2. It was assumed that in the transcription of the plasmid pSV2-CL2, the 1.8 Kb mRNA is formed on termination of transcription at the poly(A) signal contained in the vector, while the 1.0 Kb mRNA is formed on termination of transcription at the poly(A) signal in the cDNA. The results from the Northern blot hybridization coincided with these assumptions.

The results thus show that using SV40 promoter in COS 1 cells, the plasmid pSV2-CL2 can synthesize large quantities of human elastase IIIA mRNA, and most of the transcribed mRNA is not terminated at the poly(A) signal in the cDNA but instead at the poly(A) signal in the vector.

Elastase activity in supernatant of the culture medium

Since the human elastase IIIA cDNA in pSV2-CL2 has a signal peptide region, secretion of expressed elastase into the medium as a proelastase was expected. Elastase activity in the medium after 48 hours cultivation was accordingly determined. The asssay was carried out using the method of Bieth et al using a synthetic substrate [Front Matrix Biol 6 1 (1978)].

200 $\mu$l of Tris-HCl buffer solution (pH 8.5) was added to the supernatant of the culture medium (1 ml). 10 mg/ml trypsin (50 $\mu$l) was added and an activation treatment of the proelastase was carried out for 15 minutes at 25° C. Next, 50 $\mu$l of soybean trypsin inhibitor solution (10 mg/ml) and 10.4 $\mu$l of a synthetic substrate, succinyl-Ala-Ala-P-nitroanilide (125M) dissolved in N-methylpyrrolidone were added. The enzyme reaction was carried out by incubation at 37° C. for one hour. After completion of the reaction. liberated p-nitroanilide was determined by measuring absorbance at 410 nm.

In this assay of the elastase activity using the culture broth of COS1 cells transfected with pSV2-CL2, an $OD_{410}$ value of 0.21 was found the presence of elastase was thus recognized in the culture broth. However, the hydrolytic activity for the synthetic substrate was 5.2%, when compared with the hydrolytic activity of a culture supernatant from COS1 cells transfected with an expression plasmid pSV2-PEL1 containing the porcine elastase I cDNA linked to the pSV2 vector.

It is also reported that the hydrolytic activity of the human elastase purified by Largman et al from human pancreas for the synthetic substrate Suc-Ala-Ala-Ala-P-nitroanilide is about 3.5%, when compared with porcine elastase [Largman. C et al Biochemistry 15, 2491 (1976)]. These results are summarized in the following table.

| Sample | Synthetic substrate hydrolytic activity (%) |
|---|---|
| Culture supernatant of cells transfected with pSV2-PEL1 | 100 |
| Culture supernatant of cells transfected with pSV2-CL2 | 5.2 |
| Purified porcine elastase | 100 |
| Purified human elastase | 3.5 |

Thus, Suc-Ala-Ala-Ala-p-nitroanilide which is a very sensitive substrate for porcine elastase, is not a sensitive substrate for assay of human elastase activity.

The production of human elastase IIIA in COS 1 cells if plasmid pSV2-CL2 is ligated to a suitable selection marker (for example, the neo gene, dihydrofolate reductase gene, or other resistance marker) and is introduced in to CHO or other cells, a cell line suitable for sustained production of human elastase IIIA can be prepared.

(6) Production of human pancreatic elastase IIIA using *Bacillus subtilis*

Construction of expression vector pHEX010

Figure 12:
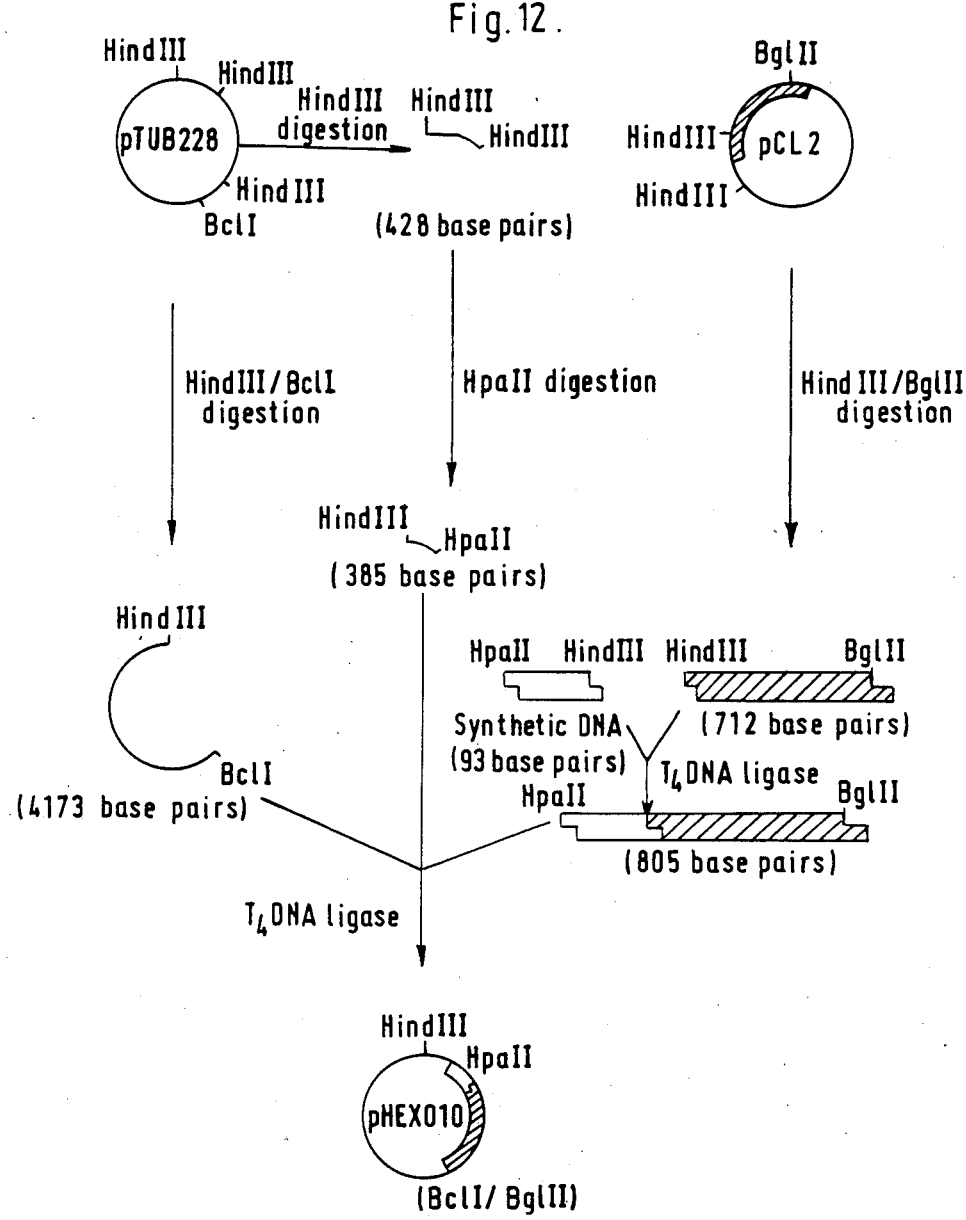
FIG. 12 illustrates the construction of plasmid pHEX010 in Example 3.

The construction method for the expression vector is illustrated in FIG. 12. Plasmid containing human elastase IIIA cDNA was digested with restriction endonucleases HindIII and BglII, and a DNA fragment of 712 base pairs containing a part of the elastase IIIA cDNA was isolated by agarose gel electrophoresis. This fragment was ligated using T4 DNA with a synthetic oligopeptide shown in FIG. 12 comprising 93 base pairs coding for a part of the signal peptide of α-amylase of *Bacillus subtilis* and 24 amino acids on the amino terminal side of elastase IIIA. A DNA fragment of 805 base pairs was isolated by agarose gel electrophoresis.

On the other hand, plasmid pTUB228 [Ohmura, K et al: J Biochem 95 87 (1984)]conIaining the α-amylase gene of *Bacillus subtilis* was digested with restriction endonuclease HindIII to isolate a DNA fragment of 428 base pairs containing the α-amylase promoter and a part of the signal peptide. and separately a DNA fragment of 5,100 base pairs containing the replication origin. The DNA fragment of 428 base pairs and the DNA fragment of 5,100 base pairs were further digested with restricticn endonuclease HpaII and BclI, respectively, to give DNA fragments of 385 base pairs and of 4173 base pairs.

The three DNA fragments were ligated with T4 DNA ligase, and incorporated into protoplasts of *Bacillus subtilis* 207 - 25 strain ($m_{168}^-$ hsrM recE4 amyE07 aroI906 leuA8 lys21; derived from Marburg strain) according to conventional procedures. After regeneration, cultivation on a medium containing 10 μg/ml of kanamycin allowed selection of the transformed strains which could grow on this medium. Selection of the desired plasmid was achieved through colony hybridization using as probe the synthetic oligonucleotide of FIG. 13. A positive clone was identified and the plasmid shown to be the intended one by determination of the base sequence.

The expression plasmid obtained in this manner was designated plasmid pHEX010.

Confirmation of the Product *Bacillus subtilis* 207-25 strain transformed with the human elastase IIIA expression plasmid pHEX010 was cultured on a reciprocal shaker in 1 l of LG medium (1% Bacto trypton, Difco; 0.5% yeast extract, Difco; 0.5% NaCl; 0.2% glucose; pH 7.0) containing 50 μg/ml of kanamycin. The culturing was performed at 35° C. for 48 hours.

After completion of the culture, the culture medium was cooled to 4° C. and centrifuged at 3000×G for 5 minutes, and the cells discarded. Ammonium sulfate was added to the supernatant to 55% saturation, and the solution was stirred at 4° C. for 12 hours. Insoluble material formed in this treatment was precipitated by centrifugation at 8000×G for 20 minutes, the supernatant was discarded, and the precipitate was dissolved in 50 mM of Tris-HCI buffer solution (pH 8.0). This solution was dialyzed against 500 ml of 50 mM Tris-HCl buffer solution (pH 8.0) for 16 hours, and insoluble material was removed by centrifugation at 8000×G for 20 minutes. The dialyzed solution was taken as a crude elastase IIIA sample solution, and the activity was determined by the following procedure.

Elastase activity in the sample solution was determined by the method described below.

The synthetic substrate, N-carbobenzoxy-L-alanine-p-nitrophenyl ester (Sigma), was dissolved in 50 mM Tris-HCl solution (pH 8.0) to give a 0.1 mM solution. To 0.25 ml of this substrate solution, 0.25 ml of the elastase sample solution was added and allowed to react for 30 minutes at 37° C. Then, the absorbance at 410 nm was determined. At the same time, to the sample solution was added elastatinal or α-b 1-antitrypsin, an elastase inhibitor, to a final concentration of 0.1 mg/ml, in order to examine the inhibition to the activity. The absorbance of the 207-25 strain inIo which the plasmid rightly oriented with the promoter was introduced increased by 0.32 in comparison with the control solution. The elastase activity could be inhibited by either of the above two inhibitors.

In this procedure, the reaction of the restriction endonuclease and the other enzymes was carried out using the buffer solutions and the reaction conditions mentioned in the literature accompanying the commercial enzyme products.

(7) Production of human pancreatic elastase IIIA using *Escherichia coli*

Various different promoters may be used, including for instance the tryptophan (trp) promoter, lactose (lac) promoter, tryptophan-lactose (tac) promoter, lipoprotein (lpp) promoter, lambda (λ) $P_L$ promoter derived from bacteriophage, or polypeptide chain elongation factor (tuf B) promoter. An example with the lactose promoter is as follows.

Figure 14:
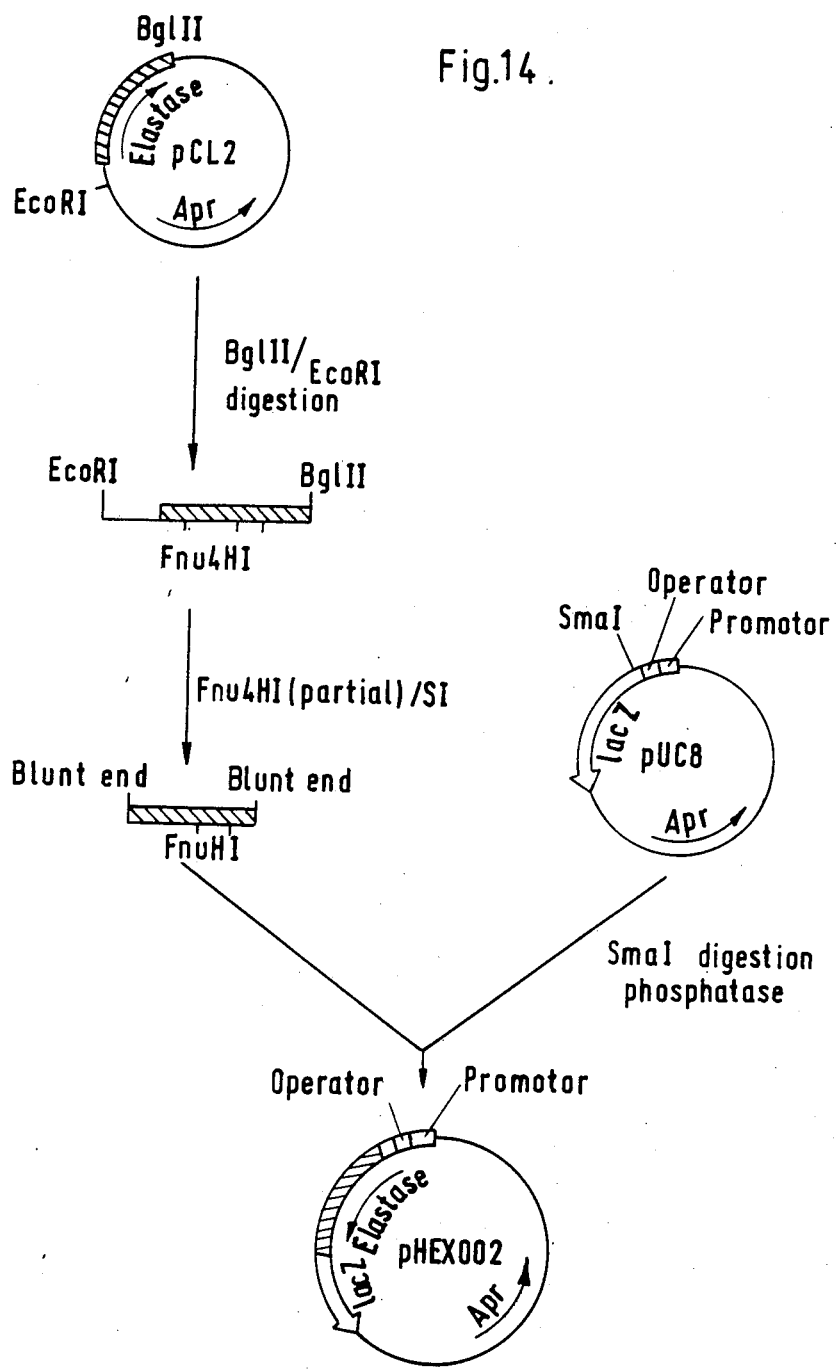
FIG. 14 illustrates the construction of plasmid pHEX002 in Example 3. The striped area represents the β-galactosidase gene. Broad arrows indicate the lactose promoter and operator, and narrow arrows show the direction of transcription.

As shown in FIG. 14, plasmid pCL2 the human elastase IIIA cDNA, CL2, was digested with restriction endonucleases EcoRI and BglII to give a DNA fragment of 1215 bp containing human elastase IIIA cDNA. This fragment was partially digested with restriction enzyme Fnu4HI and then treated with S1 nuclease to give a DNA fragment of 788 bP with blunt ends. Separately, plasmid pUC8 was digested with restriction endonuclease SmaI and treated with phosphatase to obtain a DNA fragment containing the promoter and operator region of the lactose operon and a part of the β-galactosidase coding region.

The two DNA fragments were added to 30 μl of a solution containing T4 DNA ligase (66 mM of Tris-HCl, pH 7.6; 6.6 mM of MgCl$_2$; 10 mM of DTT; 1 mM of ATP; 2.5 units of T4 DNA ligase) and incubated at 6° C. for 72 hours to ligate the fragmetns.

The thus constructed human elastase expression plasmid was named pHEX002. Various strains of *Escherichia coli* were transformed with pHEX002, and strains capable of producing human elastase could be obtained.

The human elastase expressed in this manner is a fused protein in which 8 amino acids originating from β-galactosidase combine with the N-terminal of mature human elastase, as shown below.

The DNA base sequence adjacent the 5'-terminal end of the elastase gene in plasmid pHEX002 and the encoded amino acid sequence are as follows:

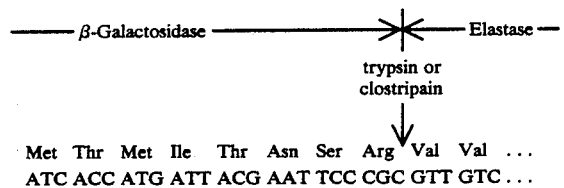

Figure 15:
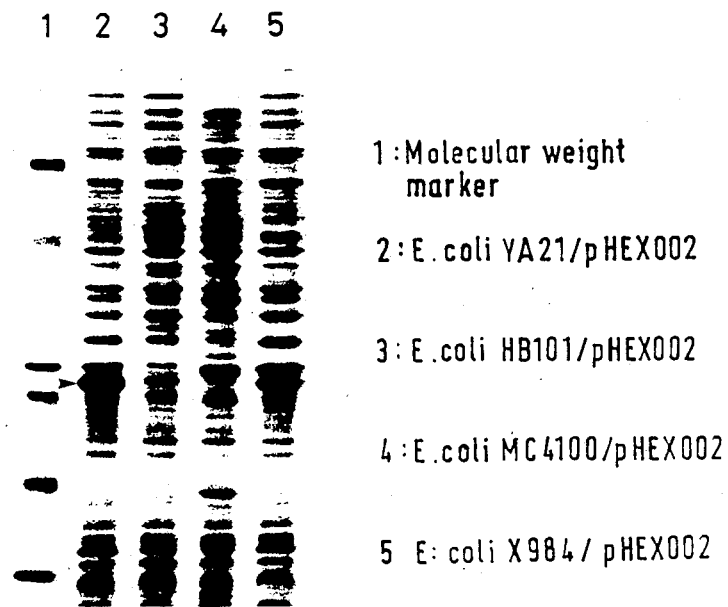
FIG. 15 reproduces the results of polyacrylamide gel electrophoresis carried out in example 3, where lane 1 corresponds to molecular weight markers, and lanes 2 to 5 correspond to *E. coli* YA21, HB101, MC4100 and χ984, respectively, when transformed with plasmid pHEX002.

The strain containing the elastase expression plasmid was inoculated on 2×TY-ampicillin medium (1.6% Bactotrypsin; 1% Yeast Extract; 0.5% NaCl; 50 μg/ml ampicillin) and cultured for 15 hours at 37° C. After completion of the culture, cells were harvested by centrifugation of the culture medium. 2.4×10$^8$ cells were suspended in 15 μl of SDS solution [2% SDS; 5% 2-mercaptoethanol; 10% glycerin; 60 mM Tris-HCl, pH 6.8]. After heating this solution at 100° C. for 3 minutes, product protein was analyzed by SDS polyacrylamide gel electrophoresis, according to the method of Laemmli et al [Nature 227, 680 (1970)]. As a result, a large amount of elastase production was found in the YA21 strain. In this respect, reference is made to FIG. 15, where lane 1 corresponds to molecular weight markers, and lanes 2 to 5 correspond to *E. coli* YA21, HB101, MC4100 and χ984, respectively, when transformed with plasmid pHEX002. The yield of elastase fused protein was 33% of the total protein produced by the YA21 strain. Though a considerable production of elastase fused protein was observed in χ984 strain, the yield was less than half that in the YA21 strain (14% of the total microorgansim cell protein). The yields of elastase fused protein in two other *Escherichia coli* strains (HB101 and MC4100 strains) were low.

Since the elastase fused protein forms inclusion bodies in cells, purification was comparatively easy. Thus, from 1 l of a culture medium of YA21 strain transformed with plasmid pHEX002, 6.5 g of cells forming inclusion bodies could be obtained. The cells (6.5 g) were lysed in 50 mM Tris-HCl buffer solution (pH 8.0) containing 0.2 mg/ml lysozyme and 1 mg/ml deoxycholic acid. Intact cells were removed by low speed centrifugation (1,500×G, 10 minutes) and inclusion bodies were recovered as a precipitate by high speed centrifugation (11,000×G, 20 minutes), Since the precipitate still contained much cell debris, the precipitate was suspended in 50 mM Tris-HCl buffer solution containing 5 mg/ml octylphenoxy polyethoxyethanol surfactant (Triton X-100, Trade Mark) and washed by high speed centrifugation (11,000×G, 20 minutes). A washed pellet of inclusion bodies was suspended in a small amount of Tris-HCl buffer solution and stored at 4° C.

The purified inclusion body (370 mg) containing about 58% elastase IIIA fused protein could be obtained by this procedure. The inclusion body produced by YA21 strain transformed with pH2EX-2 was shown to contain the elastase fused protein by immuno-blotting.

Most of the elastase produced by *Escherichia coli* is in insoluble parts of the cells as inclusion bodies, but a smaller proportion exists in a soluble state and retaihs enzyme activity. Determination of the enzyme activity was carried out as follows. The χ984 strain transformed with plasmid pHEX002 was cultured with shaking in 1 l of 2×TY-amplicillin medium at 37° C. for 15 hours. After completion of the culturing, the cells were harvested by centrifugation at 3000×G for 5 minutes and suspended in 20 ml of buffer solution A (50 mM Tris-HCl, pH 8.0; lmM EDTA; 50 mM NaCl). 10 mg of lysozyme was added, and the suspension incubated at 5° C. for 20 minutes. Deoxycholic acid to a final concentration of 1 mg/ml was added to the resultant suspension which was then incubated at 20° C. Deoxyribonuclease to a final concentration of 0.1 mg/ml was added, and the cells were disrupted in a polytron homogenizer. After removal of the cell debris by centrifugation at 80,000×G, 40 minutes, the lysate was subjected to column chromatography on high molecular weight, cross-linked dextran (Sephadex G-75). The fractions having elastase activity were purified by antibody affinity chromatography, and used for the following determination of elastase activity.

Elastase activity in the sample solution was determined by the following procedure. N-carbobenzoxy-L-alanine-p-nitrophenyl ester (Sigma), a sythetic substrate, was dissolved in 50 mM Tris-HCl (pH 8.0) to give a 0.1 mM solution. To 0.25 ml of this substrate solution, 0.25 ml of the elastase sample solution was added, and, after reaction for 30 minutes at 37° C., the absorbance at 410 nm was determined. The elastase activity was detected by the increase in the absorbance of 0.41. At the same time, when elastatinal or α-1-antitrypsin (an elastase inhibitor), was added to this sample solution to a final concentration of 0.1 mg/ml, it was found that the inhibitor inhibited the activity.

Production of human Pancreatic elastase IIIA using yeast

In the case of yeast as a host (and as with a *Escherichia coli, Bacillus subtilis* or mammalian cells), human pancreatic elastase IIIA cDNA could be ligated to a suitable expression vector using known technigues, inserted into the host cells and expressed. Elastase activity in the culture medium was confirmed.

*Saccharomyces cerevisiae* described in "Japanese Guidelines for Recombinant DNA Research" may be used as host, but S288C strain and other strains are practically suitable. On the other hand, YEP13 and other vectors were appropriate as a vector. As promoter, the ADH1 gene coding for alcohol dehydrogenase gene, and other promoters, are suitable.

Example 4:

Elastase IIIB (1) Separation of mRNA from human pancreas

Human pancreas (autopsy sample) weighing 5.5 g was homogenised and denatured in a homogeniser (a polytron homogeniser from Kinematica GmbH, Germany, polytron being a Trade Mark) in an adequate amount of guanidine thiocyanate solution (4M guanidine thiocyanate; 1% detergent, Sarcosyl from Sigma Chemical Co, USA; 20 mM ethylenediaminetetraacetic acid (EDTA); 25 mM sodium citrate, pH 7.0; 100 mM 2-mercaptoethanol and 0.1% antifoaming agent, Antifoam A from Sigma Chemical Co USA), followed by centrifugation, to obtain a supernatant.

One volume of supernatant was added to 0.025 volumes of 1M acetic acid and 0.75 volumes of ethanol, and the mixture cooled to $-20°$ C. for several hours, followed by centrifugation, to obtain a precipitate. The precipitate was suspended in a guanidine hydrochloride solution (7.5M guanidine hydrochloride; 25 mM sodium citrate, pH 7.0; and 5 mM dithiothreitol, DTT). To 1 volume of the suspension was added 0.025 volumes of 1M acetic acid and 0.5 volumes of ethanol, and the resultant mix cooled to $-20°$ C. for several hours, followed by centrifugation. The resultant precipitate was suspended again in more of the guanidine hydrochloride solution, mixed as before with acetic acid and ethanol, cooled to $-20°$ C. and cenrrifuged, followed by collection of the precipitate. Next, the precipitate was washed several times with ethanol to remove guanidine hydrochloride, and then dissolved in distilled water, followed by precipitation of the RNA with ethanol. The precipitate was collected by centrifugation to give 53.9 mg of RNA.

The RNA thus obtained was adsorbed onto an oligo(dT) cellulose column in a high concentration salt solution (0.5M NaCl; 20 mM Tris-HCl, pH 7.5; 1 mM EDTA; and 0.1% sodium dodecyl sulfate. SDS), and the mRNA-containing poly(A) was eluted with an elution buffer (10 mM Tris-HCl, pH 7.5; 1 mM EDTA; and 0.05% SDS) to give 255 $\mu$g of mRNA.

(2) Preparation of cDNA bank

The preparation of a cDNA bank was carried out according to the Okayama-Berg method. 5 $\mu$g of the mRNA and 24 units of a reverse transcriptase were incubated at 42° C. for 60 minutes in 20 $\mu$l of a reaction mixture (50 mM of Tris-HCl, pH 8.3; 8 mM of $MgCl_1$; 30 mM of KCl; 0.3 mM of DTT; 2 mM each of dATP, dGTP, dCTP and dTTP; 10 $\mu$Ci of $\alpha$-$^{32}$P-dCTP; and 1.4 $\mu$g of vector primer DNA, purchased from PL-Pharmacia).

The reaction was stopped by the addition of 2 $\mu$l of 0.25M EDTA and 1 $\mu$l of 10% SDS. Deproteinization was carried out with 20 $\mu$l of phenol-chloroform. After centrifugation of the reaction mixture, the aqueous layer was collected. 20 $\mu$l of 4M ammonium acetate and 80 $\mu$l of ethanol were added to the aqueous layer and the mixture cooled to $-70°$ C. for 15 minutes. The precipitate was then collected by centrifugation and washed with 75% aqueous ethanol and dried under reduced pressure.

The resultant precipitate was dissolved in 15 $\mu$l of terminal transferase reaction mix(ure (140 mM potassium cacodylate, of formula $C_2H_6AsKO_2$; 30 mM Tris-HCl, pH 6.8; 1 mM cobalt chloride; 0.5 mM DTT; 0.2 $\mu$g of poly(A); and 100 mM of dCTP). After incubating the solution at 37° C. for 3 minutes, 18 units of terminal deoxynucleotidyl transferase were added and allowed to react for 5 minutes.

The above reaction was stopped by addition of 1 $\mu$l of 0.25M EDTA and 0.5 $\mu$l of 10% SDS. Deproteinization was then carried out with phenol-chloroform. After centrifugation of the reaction mixture, the agueous layer was collected. 15 $\mu$l of 4M ammonium acetate and 60 $\mu$l of ethanol were added to the aqueous layer and mixed well. After cooling the mixture to $-70°$ C. for 15 minutes, the precipitate was collected by centrifugation.

The precipitate was dissolved in a buffer for restriction endonuclease (50 mM NaCl; 10 mM Tris-HCl, pH 7.5; 10 mM $MgCl_2$; and 1 mM DTT). 2.5 units of the restriction enzyme HindIII were added to the solution and the solution incubated at 37° C. for about 1 hour. After deproteinization with phenol-chloroform, precipitation was carried out with ethanol.

After cooling to $-70°$ C. for 15 minutes, the precipitate was collected by centrifugation and dissolved in 10 $\mu$l of TE (10 mM Tris-HCl, pH 7.5; 1 mM EDTA).

1 $\mu$l of the above sample solution was then added to a reaction solution (10 mM Tris-HCl, pH 7.5; 1 mM EDTA; and 100 mM NaCl), followed by addition of 10 ng of linker (purchased from PL-Pharmacia) bearing oligo dG. The resulting mixture was heated at 65° C. for 5 minutes and maintained at 42° C. for 30 minutes.

After cooling the reaction solution in ice water, 10 $\mu$l of 10-fold ligase buffer solution (10 mM ATP; 660 mM Tris-HCl, pH 7.5; 66 mM $MgCl_2$; and 100 mM DTT). 78 $\mu$l of distilled water and 8 units of T4 DNA ligase were added to the solution and the reaction mixture maintained at 12° C. overnight.

Then, to the thus prepared mixture, 10 $\mu$l of 1M KCl. 1 unit of ribonuclease H, 33 units of DNA polymerase I, 4 units of T4 DNA ligase. 0.5 $\mu$l of nucleotide solution (20 mM dATP, 20 mM dGTP, 20 mM dCTP and 20 mM dTTP) and 0.1 $\mu$l of 50 $\mu$g/$\mu$l bovine serum albumin (BSA) were added and the mixture maintained at 12° C. for 1 hour and then at 25° C. for 1 hour.

After diluting the reaction solution 5-fold, E. coli strain RR1 was transformed according to the method of Hanahan [Hanahan, D; J Mol Biol 166, 557 (1983)] to prepare a human pancreatic cDNA bank.

(3) Selection of transformed bacteria containing human pancreactic elastase IIIB cDNA The DNA from 4,700 clones of the human pancreactic cDNA bank was fixed onto nitrocellulose filter according to the method of Grunstein, M and Hogness, D S [Proc Natl Acad Sci, USA. 72, 3961 (1975)].

A porcine pancreatic elastase I cDNA fragment was excised with restriction endonuclease PstI and labelled with $^{32}$P according to the nick translation method [Rigby, P W et al:J. Mol. Biol 113, 237 (1977)]. Using the DNA fragment as probe, it was hybridized with the DNA fixed on the filter at 35° C. in a solution of 40% formamide 5-fold concentrated SSC (0.75M sodium chloride and 0.075M sodium citrate) (SSC), along with a solution of 0.1% BSA, 0.1% polysucrose (Ficoll, Trade Mark), 0.1% polyvinyl pyrrolidone. 0.5% SDS, 10 mM sodium phosphate and 100 $\mu$g/ml of salmon spermatozoon DNA.

10 microorganism strains which hybridized with the probe were identified by autoradiography. A plasmid from one of the strains was named pCL1, and the inserted cDNA was named CL1.

(4) The amino acid sequence and elastase IIIB coded by plasmid pCL1

In CL1, there exists only one open reading frame. This sequence codes for 270 amino acids. The encoded amino acid sequence showed some homology with trypsin and chymotrypsin, to a degree of only about 30%. However, there was a higher homology, 50%, with porcine pancreatic elastase I. There also existed an amino acid sequence (Gly-AsP-Ser-Gly-Gly-Pro) around the active center which is be commonly found in the same region in serine proteases such as trypsin, chymotrypsin, etc. Further, there is a 45th histidine residue, 95th aspartic acid residue and 189th serine residue which can participate in the characteristic charge relay of serine proteases.

Moreover. the encoded amino acid sequence adjacent the carboxyl terminal, which in elastase forms a pocket for binding with the substrate is very similar between human pancreatic elastase IIIB and the porcine elastase I. There is also an encoded 211th valine residue and 223rd threonine residue, which are characteristic of a substrate-binding pocket of the porcine elastase I. The base sequence was of the formula

```
(5')- CCT ATC ATC GCA
AAA CTC ATG ATG CTC CGG CTG CTC AGT TCC
CTC CTC CTT GTG GCC GTT GCC TCA GGC TAT
GGC CCA CCT TCC TCT CGC CCT TCC AGC CGC
GTT GTC AAT GGT GAG GAT GCG GTC CCC TAC
AGC TGG CCC TGG CAG GTT TCC CTG CAG TAT
GAG AAA AGC GGA AGC TTC TAC CAC ACC TGT
GGC GGT AGC CTC ATC GCC CCC GAC TGG GTT
GTG ACT GCC GGC CAC TGC ATC TCG AGC TCC
CGG ACC TAC CAG GTG GTG TTG GGC GAG TAC
GAC CGT GCT GTG AAG GAG GGC CCC GAG CAG
GTG ATC CCC ATC AAC TCT GGG GAC CTC TTT
GTG CAT CCA CTC TGG AAC CGC TCG TGT GTG
GCC TGT GGC AAT GAC ATC GCC CTC ATC AAG
CTC TCA CGC AGC GCC CAG CTG GGA GAC GCC
GTC CAG CTC GCC TCA CTC CCT CCG GCT GGT
GAC ATC CTT CCC AAC GAG ACA CCC TGC TAC
ATC ACC GGC TGG GGC CGT CTC TAT ACC AAC
GGG CCA CTC CCA GAC AAG CTG CAG GAG GCC
CTG CTG CCG GTG GTG GAC TAT GAA CAC TGC
TCC AGG TGG AAC TGG TGG GGT TCC TCC GTG
AAG AAG ACC ATG GTG TGT GCT GGA GGG GAC
ATC CGC TCC GGC TGC AAT GGT GAC TCT GGA
GGA CCC CTC AAC TGC CCC ACA GAG GAT GGT
GGC TGG CAG GTC CAT GGC GTG ACC AGC TTT
GTT TCT GCC TTT GGC TGC AAC ACC CGC AGG
AAG CCC ACG GTG TTC ACT CGA GTC TCC GCC
TTC ATT GAC TGG ATT GAG GAG ACC ATA GCA
AGC CAC TAG AAC CAA GGC CCA GCT GGC AGT
GCT GAT CGA TCC CAC ATC CTG AAT AAA GAA
TAA AGA TCT CTC AGA AAA A-(3')
```

Beginning with the underlined ATG triplet, the encoded amino acid sequence is of the formula:

(N)- Met Met Leu Arg Leu Leu Ser Ser
Leu Leu Leu Val Ala Val Ala Ser Gly Tyr
Gly Pro Pro Ser Ser Arg Pro Ser Ser Arg
Val Val Asn Gly Glu Asp Ala Val Pro Tyr
Ser Trp Pro Trp Gln Val Ser Leu Gln Tyr
Glu Lys Ser Gly Ser Phe Tyr His Thr Cys
Gly Gly Ser Leu Ile Ala Pro Asp Trp Val
Val Thr Ala Gly His Cys Ile Ser Ser Ser
Arg Thr Tyr Gln Val Val Leu Gly Glu Tyr
Asp Arg Ala Val Lys Glu Gly Pro Glu Gln

-continued

Val Ile Pro Ile Asn Ser Gly Asp Leu Phe
Val His Pro Leu Trp Asn Arg Ser Cys Val
Ala Cys Gly Asn Asp Ile Ala Leu Ile Lys
Leu Ser Arg Ser Ala Gln Leu Gly Asp Ala
Val Gln Leu Ala Ser Leu Pro Pro Ala Gly
Asp Ile Leu Pro Asn Glu Thr Pro Cys Tyr
Ile Thr Gly Trp Gly Arg Leu Tyr Thr Asn
Gly Pro Leu Pro Asp Lys Leu Gln Glu Ala
Leu Leu Pro Val Val Asp Tyr Glu His Cys
Ser Arg Trp Asn Trp Trp Gly Ser Ser Val
Lys Lys Thr Met Val Cys Ala Gly Gly Asp
Ile Arg Ser Gly Cys Asn Gly Asp Ser Gly
Gly Pro Leu Asn Cys Pro Thr Glu Asp Gly
Gly Trp Gln Val His Gly Val Thr Ser Phe
Val Ser Ala Phe Gly Cys Asn Thr Arg Arg
Lys Pro Thr Val Phe Thr Arg Val Ser Ala
Phe Ile Asp Trp Ile Glu Glu Thr Ile Ala
Ser His -(C)

The amino acid sequence of the coded protein appears at a glance to be analogous with the amino acid composition of the human pancreatic elastase I reported by Largman et al [Largman, C et al: Biochemistry 15, 2491 (1976) ]. However, the present elastase was clearly different in detail from the known one, and the molecular weights were also different. The active form of the human elastase may be produced by cleaving at the carboxy group of the 28th arginine residue (counted from the N-terminal) of the preproelastase, and retaining the longer, C-terminal portion. Cleaving can be effected for example with trypsin.

The degree of homology in encoded amino acid sequence between preproelastase IIIB of CL1 and preproelastase IIIA of CL2 is as high as 93.3%. The degree of homology in base sequence between preproelastase CL2 and CL1 is as high as 95.3%. Hence the elastases are closely related proteins. In the human pancreas, the amount of mRNA corresponding to CL1 is about 10% of that for CL2.

Since pCL1 contains an entire DNA coding for human pancreatic elastase IIIB, :t is possible to produce large amounts of the elastase IIIB by transferring the cDNA to an appropriate expression vector and using, for example, E. coli, B. subtilis, yeast or mammalian cells as the host.

(5) production of human pancreatic elastase IIIB using mammalian cells

Construction of expression plasmid pSV2-CL1

Figure 16:
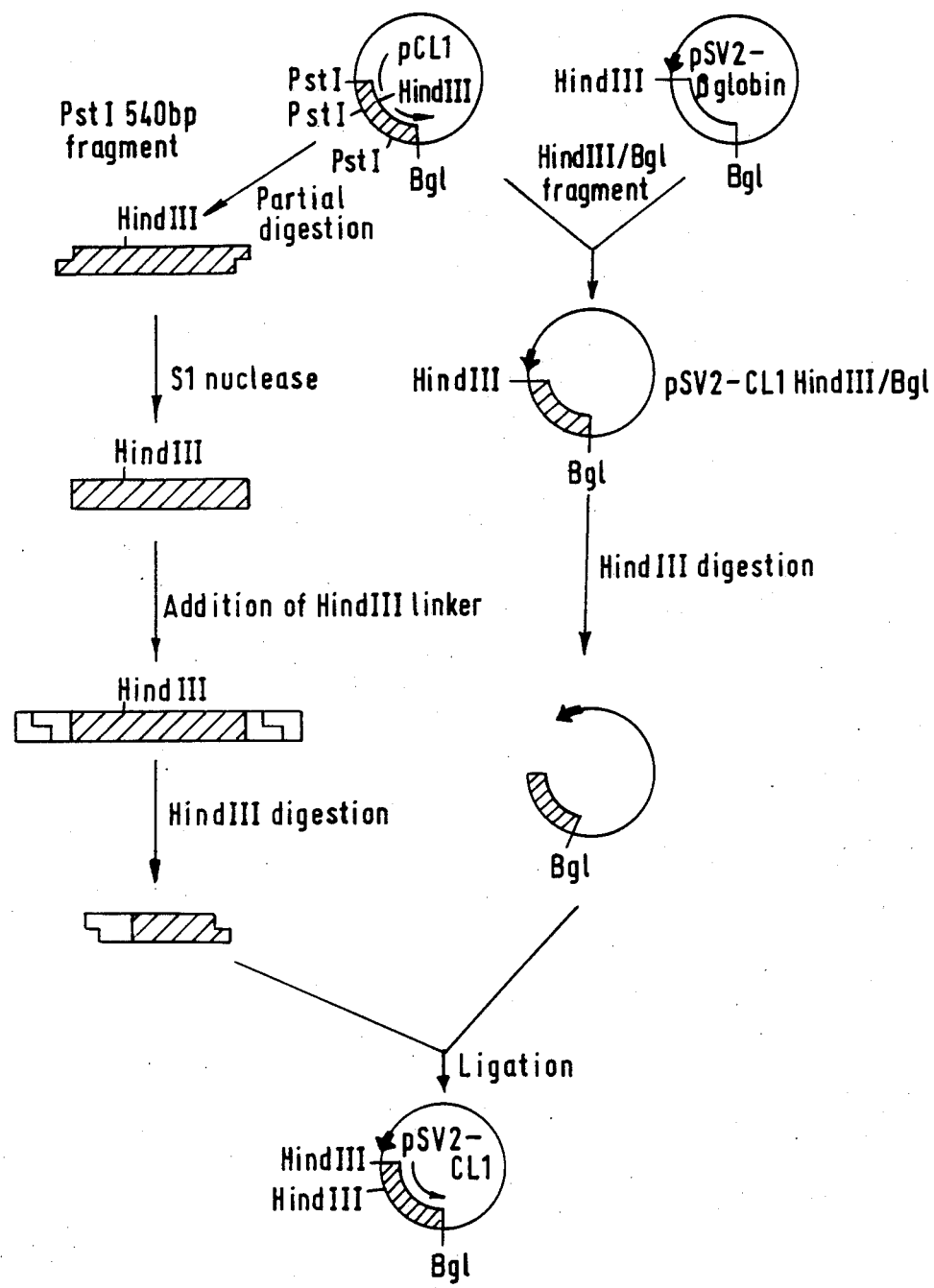
FIG. 16 illustrates the construction of plasmid pSV2-CL1 in Example 4.

In order to produce human elastase IIIB using mammalian cells as host, the cDNA was ligated to an expression vector according to the procedure indicated in FIG. 16. The known pSV2 plasmid containing the SV40 promoter, enhancer, poly(A) signal and introns of the Small T antigen gene was used for construction of the expression vector. pSV2-β-globin is a plasmid based on the pSV2 vector with inserted β-globin cDNA. plasmid pCL1 is the plasmid with inserted human elastase IIIB cDNA. The reactions with S1 nuclease, etc, were carried out according to the methods described in "Molecular Cloning" [Maniatis, T et al (ed) "Molecular Cloning" Cold Spring Harbor Lab (1982)]. The broad arrows in FIG. 16 represent the promoter derived from SV40 , and the narrow arrows show the direction of transcription.

From analysis of the restriction endonuclease excision pattern, an expression plasmid (pSV2-CL1) was selected which incorporated the desired fragments oriented in the correct sense for the transcription of the vector and cDNA.

Transfection of COS 1 cells with expression plasmid pSV2-CL1

The constructed expression plasmid pSV2-CL1 was transfected into COS 1 (mammalian cells) by the calcium phosphate method described in the literature [Graham and Thus, $1 \times 10^6$ of COS 1 cells were seeded on Petri dishes (10 cm in diameter), and cultured overnight on Dulbecco-modified Eagle medium containing 10% fetal calf serum.

Plasmid pSV2-CL1 (300 μg) was suspended in sterile distilled water (12.55 ml), then 2.5M $CaCl_2$ (0.75 ml) was added and the suspension mixed thoroughly. A pipette was used to bubble air through the system in order to maintain agitation, and 1.5 ml of 10×HeBS solution (HEPES, 210 mM; NaCl, 1.37M; KCl 4.7 mM; $Na_2HPO_4$, 10.6 mM; glucose, 55.5 mM; pH 7.05) was dropped into the resulting solution to precipitate the DNA and calcium phosphate.

The precipitate was allowed to stand at room temperature for 30 minutes to mature the precipitate, and 1 ml of the solution for each Petri dish was added to the COS 1 cells cultured in fresh medium containing 10% fetal calf serum.

After cultivation of these cells for 12 hours at 37° C. in the presence of 5% $CO_2$, the culture medium was discarded in favour of a fresh, Dulbecco-modified Eagle medium containing no fetal calf serum. The cells were cultured for a further 48 hours at 37° C. in the presence of 5% $CO_2$. The transfected COS 1 cells obtained by this procedure were tested to detect the presence of human elastase IIIB mRNA, while the supernatent of the culture medium was tested for elastase activity.

Extraction of mRNA from COS 1 cells

In order to confirm the existence of human elastase IIIB mRNA transcribed from the expression plasmid in the transfected COS 1 cells, mRNA was extracted from the COS 1 cells and assaYed by the Northern blot hybridization according to the following procedure.

After cultivation of the COS 1 cells for 48 hours, 1 ml of guanidine thiocyanate solution (4M guanidine thiocyanate; 1% Sarcosyl; 20 mM EDTA; 25 mM sodium citrate, pH 7.0; 100 mM 2-mercaptoethanol; 0.1% Antifoam A) was added to each Petri dish in order to dissolve the cells.

High molecular DNA molecules were degraded to low molecular ones by passing the solution several times through a 21 guage injection needle. The resultant solution was layered on a solution containing 5.7M cesium chloride and 0.1M EDTA, and the solution Hitachi RPS 40 swing rotor. The resultant RNA precipitate was washed with a small amount of ethanol and dissolved in distilled water (300 μl).

According to the method of Aviv and Leder [Proc Natl Acad Sci, USA 69, 1408 (1972)], the extracted total RNA was purified on an oligo(dT) cellulose column to give several μg of purified mRNA. Half of the purified mRNA was used for Northern blot hybridization by the Thomas method [Proc Natl Acad Sci, USA 77 5201 (1980)]. $^{32}P$-Labelled human elastase IIIA cDNA was used as a probe by the nick translation method [Rigby, P W et al: J Mol Biol 113, 237 (1977)]. A major band at about 1.8 Kb and a minor band at about 1.0 Kb which hydridized with the probe were detected only in the mRNA of COS 1 cells transfected with plasmid pSV2-CL1. It was assumed that in the transcription of the plasmid pSV2-CL1, the 1.8 Kb mRNA is formed on termination of transcription at the poly(A) signal contained in the vector, while the 1.0 Kb mRNA is formed on termination of transcription at the poly(A) signal in the cDNA. The results from the Northern blot hybridization coincided with these assumptions.

The results thus show that using SV40 promoter in COS 1 cells, the plasmid pSV2-CL1 can synthesize large quantities of human elastase IIIB mRNA, and most of the transcribed mRNA is not terminated at the poly(A) signal in the cDNA but instead at the poly(A) signal in the vector.

Elastase activity in supernatant of the oulture medium Since the human elastase IIIB cDNA in pSV2-CL1 has a signal peptide region, secretion of expressed elastase into the medium as a proelastase was expected. Elastase activity in the medium after 48 hours cultivation was accordingly determined. The asssay was carried out using the method of Bieth et al using a synthetic substrate [Front Matrix Biol 6 1 (1978)].

200 μl of 1M Tris-HCl buffer solution (pH 8.5) was added to the supernatant of the culture medium (1 ml). 10 mg/ml trypsin (50 μl) was added, and an activation treatment of the proelastase was carried out for 15 minutes at 25° C. Next, 50 μl of soybean trypsin inhibitor solution (10 mg/ml) and 10.4 μl of a synthetic substrate, succinyl-Ala-Ala-Ala-P-nitroanilide (125 mM) dissolved in 125 mM of N-methylpyrrolidone were added. The enzyme reaction was carried out by incubation at 37° C. for one hour. After completion of the reaction, liberated p-nitroanilide was determined by measuring absorbance at 410 nm.

Elastase activity in the culture medium of COS 1 cells transfected with pSV2-CL1 was found, after activation with trypsin.

The production of human elastase IIIB in COS 1 cells transfected with plasmid pSV2-CL1 was transient. However, if plasmid pSV2-CL1 is ligated to a suitable selection marker (for example, the neo gene, dihydrofolate reductase gene, or other resistance marker) and is introduced in to CHO or other cells, a cell line suitable for sustained production of human elastase IIIB can be prepared.

(6) Production of human pancreatic elastase IIIB using *Bacillus subtilis*

Construction of expression vector pHAM001

Figure 17:
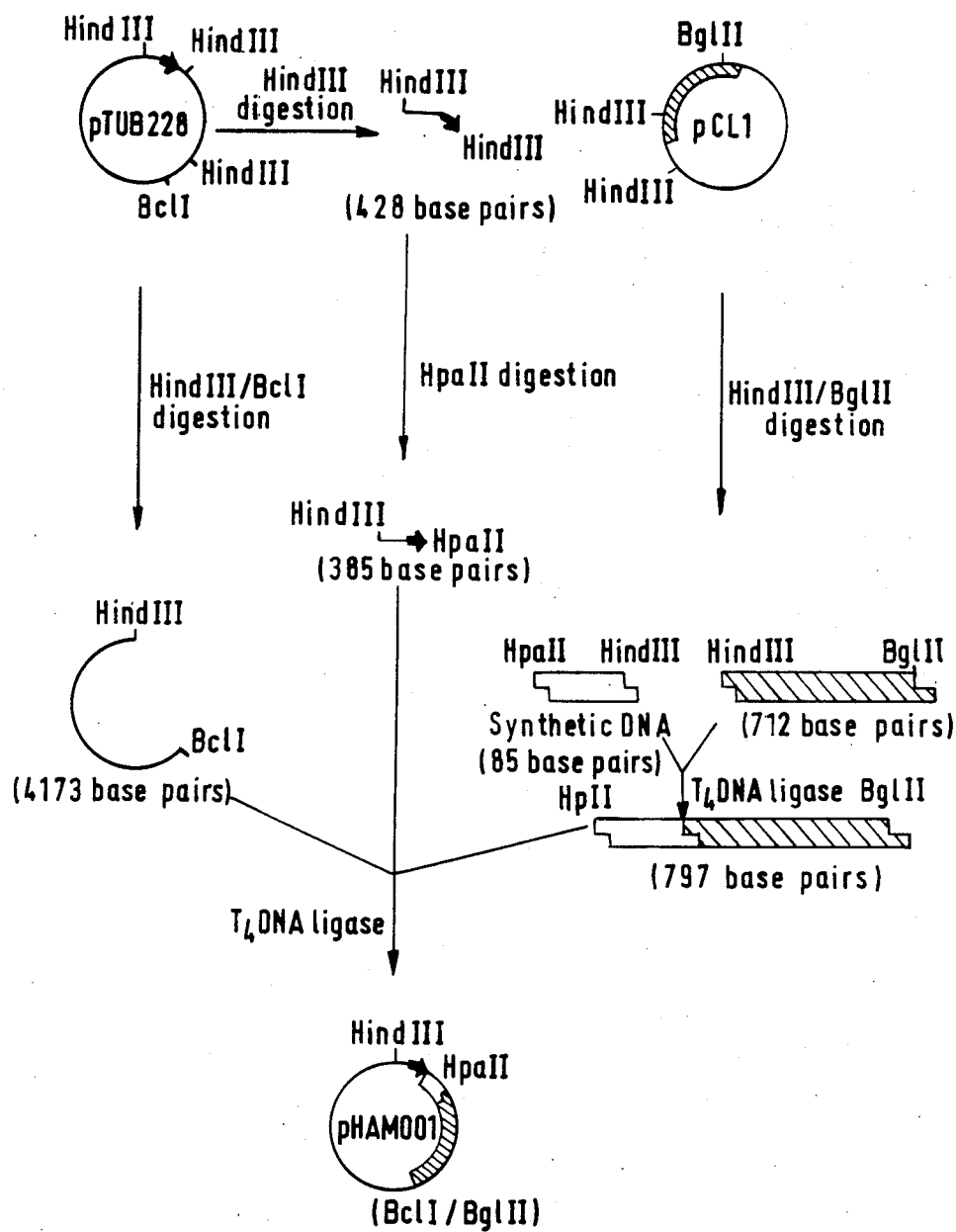
FIG. 17 illustrates the construction of plasmid pHAM001 in Example 4.

The construction method for the expression vector is illustrated in FIG. 17. Plasmid containing human elastase IIIB cDNA was digested with restriction endonucleases HindIII and BglII, and a DNA fragment of 712 base pairs containing a part of rhe elastase IIIB cDNA was isolated by agarose gel electrophoresis. This fragment was ligated using T4 DNA ligase with a synthetic oligonucleotide of 85 base pairs shown in FIG. 18 which codes for a part of the signal peptide of α-amylase of *Bacillus subtilis* and for 24 Amino acids residues on the amino terminal side of elastase IIIB. A DNA fragment of 797 base pairs was isolated by agarose gel electrophoresis. On the other hand, plasmid pTUB228 [Ohmura. K et al: J Biochem 95 87 (1984)] containing the α-amylase gene of *Bacillus subtilis* was digested with restriction endonuclease HindIII to isolate a DNA fragment of 428 base pairs containing the α-amylase promoter and a part of the signal peptide, and separately a DNA fragment of 5,100 base pairs containinq the replication origin. The DNA fragment of 428 base pairs and the DNA fragment of 5,100 base pairs were further digested with restriction endonuclease HPaII and BcII, respectively, to give DNA fragments of 385 base pairs and of 4173 base pairs.

The three DNA fragments were ligated with T4 DNA ligase, and incorporated into protoplasts of *Bacillus subtilis* 207-25 strain (m-$_{168}^-$ hsrM recE4 amyE07 aroI906 leuA8 lys21; derived from Marburg strain) according to oonventional procedures. After regeneration, cultivation on a medium containing 10 μg/ml of kanamycin allowed selection of the transformed strains which could grow on this medium. Selection of the desired plasmid was achieved through colony hybridization using as probe the synthetic oligonucleotide of FIG. 18. A positive clone was identified and the plasmid shown to be the intended one by determination of the base sequence. The expression plasmid obtained in this manner was designated plasmid pHAM001.

Confirmation of the Product

*Bacillus subtilis* 207-25 strain transformed with the human elastase IIIB expression plasmid pHAM001 was cultured on a reciprocal shaker in 1 l of LG medium (1% Bacto trypton, Difco; 0.5% yeast extract, Difco; 0.5% NaCl; 0.2% glucose; pH 7.0) containing 50 μg/ml of kanamycin. The culturing was performed at b 35° C. for 48 hours.

After completion of the culture, the culture medium was cooled to 4° C. and centrifuged at 3000×G for 5 minutes, and the cells discarded. Ammonium sulfate was added to the supernatant to 55% saturation, and the solution was stirred at 4° C. for 12 hours. Insoluble material formed in this treatment was precipitated by centrifugation at 8000×G for 20 minutes, the supernatant was discarded, and the precipitate was dissolved in 50 mM Tris-HCl buffer solution (pH 8.0). This solution was dialyzed against 500 ml of 50 mM Tris-HCl buffer solution (pH 8.0) for 16 hours, and insoluble material was removed by centrifugation at 8000×G for 20 minutes. The dialyzed solution was taken as a crude elastase IIIB sample solution, and the activity was determined by the following procedure.

Elastase activity in the sample solution was determined by the method described below.

The synthetic substrate, N-carbobenzoxy-L-alanine-p-nitrophenyl ester (Sigma), was dissolved in 50 mM Tris-HCl solution (pH 8.0) to give a 0.1 mM solution. To 0.25 ml of this substrate solution, 0.25 ml of the elastase sample solution was added and allowed to react for 30 minutes at 37° C. Then, the absorbance at 410 nm was determined. At the same time to tbe sample soluticn was added elastatinal or α-1-antitrypsin, an elastase inhibitor, to a final concentration of 0.1 mg/ml, in order to examine the inhibition to the activity. The absorbance of the 207-25 strain into which the plasmid rightly oriented with the promoter was introduced increased by 0.24 in comparison with the control solution. The elastase activity could be inhibited by either of the above two inhibitors.

In this procedure, the reaction of the restriction endonuclease and the other enzymes was carried out using the buffer solutions and the reaction conditions mentioned in the literature accompanying tbe commercial enzyme products.

(7) Production of human pancreatic elastase IIIB using *Escherichia coli*

Various different promoters may be used, including for instance the tryptophan (trp) promoter, lactose (lac) promoter, tryptophan-lactose (tac) promoter, lipoprotein (lpp) promoter, lambda (λ) P$_L$ promoter derived from bacteriophage, or polypeptide chain elongation factor (tuf B) promoter. An example with the lactose promoter is as follows.

Figure 19:
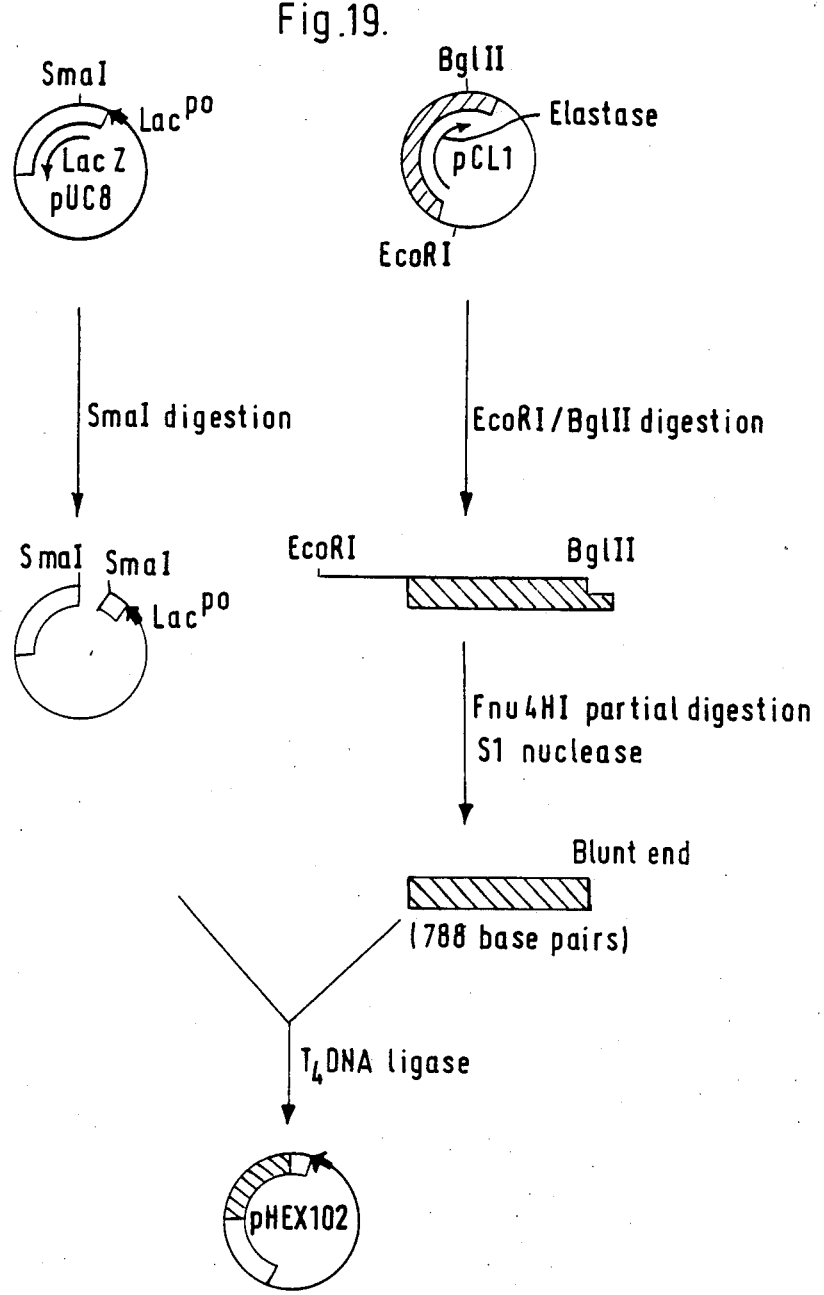
FIG. 19 illustrates the construction of plasmid pHEX102 in Example 4. The striped area represents the β-galactosidase qene. Broad arrows indicate the lactose promoter and operator, and narrow arrows show the direction of transcription.

As shown in FIG. 19, the human elastase IIIB cDNA, CL1, was digested with restriction endonucleases EcoRI and BglII to give a DNA fragment of 1640 bP containing human elastase IIIB cDNA. This fragment was partially digested with restriction enzyme Fnu4HI and then treated with S1 nuclease to give a DNA fragment of 788 bP with blunt ends. Separately, plasmid PUC8 was digested with restriction endonuclease SmaI and treated with phosphatase to obtain the DNA fragment containing the promoter and operator region of the lactose operon and a part of the β-galactosidase coding region.

The two DNA fragments were added to 30 μl of a solution containing T4 DNA ligase (66 mM of Tris-HCl, pH 7.6; 6.6 mM of MgCl$_2$; 10 mM of DTT; 1 mM of ATP; 2.5 units of T4 DNA ligase) and incubated at 6° C. for 72 hours to ligate the fragments.

The thus constructed human elastase expression plasmid was named pHEX102. Various strains of *Escherichia coli* were transformed with pHEX102, and strains capable of producing human elastase could be obtained.

The human elastase expressed in this manner is a fused protein in which 8 amino acids originating from β-galactosidase combine with the N-terminal of mature human elastase, as shown below.

The DNA base sequence adjacent the 5'-terminal end of the elastase gene in plasmid pHEX102 and the encoded amino acid sequence are as follows:

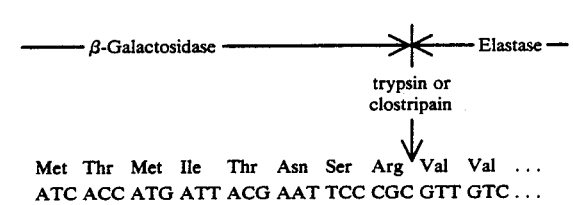

```
————— β-Galactosidase —————>|<————— Elastase ——
                             trypsin or
                             clostripain
                                 ↓
Met Thr Met Ile  Thr Asn Ser Arg  Val Val ...
ATC ACC ATG ATT  ACG AAT TCC CGC  GTT GTC ...
```

The strain containing the elastase expression plasmid was inoculated on 2×TY-ampicillin medium (1.6% Bactotryptone; 1% yeast Extract; 0.5% NaCl; 50 μg/ml ampicillin) and cultured for 15 hours at 37° C. After completion of the culture, cells were harvested by centrifugation of the oulture medium. 2.4×10$^8$ cells were suspended in 15 μl of SDS solution [2% SDS; 5% 2-mercaptoethanol; 10% glycerin; 60 mM Tris-HCl. pH 6.8]. After heating this solution at 100° C. for 3 minutes, product protein was analyzed by SDS polyacrylamide gel electrophoresis, according to the method of Laemmli et al [Nature 227, 680 (1970)].

Since the elastase fused protein forms inclusion bodies in cells, purification was comparatively easy. Thus, from 1 l of a culture medium of YA21 strain transformed with plasmid pHEX102, 6.6 g of cells forming inclusion bodies could be obtained. The cells (6.6 g) were lysed 0.2 mg/ml lysozyme and 1 mg/ml deoxycholic acid. Intact cells were removed by low speed centrifugation (1,500×G, 10 minutes) and inclusion bodies were recovered as a precipitate by high speed centrifugation (11,000×G, 20 minutes). Since the precipitate still contained much cell debris, the precipitate was suspended in 50 mM Tris-HCl buffer solution containing 5 mg/ml octylphenoxy polyethoxyethanol surfactant (Triton X-100, Trade Mark) and washed by high speed centrifugation (11,000×G, 20 minutes). A washed pellet of inclusion bodies was suspended in a small amount of Tris-HCl buffer solution and stored at 4° C. The purified inclusion body (350 mg) containing nearly 50% elastase IIIB fused protein could be obtained by this procedure. The inclusion body produced by YA21 strain transformed with pHEX102 was shown to contain the elastase fused protein by immuno-blotting.

Most of the elastase produced by *Escherichia coli* is in insoluble parts of the cells as inclusion bodies, but a smaller proportion exists in a soluble state and retains enzyme activity. Determination of the enzyme activity was carried out as follows.

The strain χ984 transformed with plasmid pHEX102 was cultured with shaking in 1 l of 2×TY-ampicillin medium at 37° C. for 15 hours. After completion of the culturing, the cells were harvested by centrifugation at 3000×G for 5 minutes and suspended in 20 ml of buffer solution A (50 mM Tris-HCl, pH 8.0; 1 mM EDTA; 50 mM NaCl). 10 mg of lyzozyme was added, and the suspension incubated at 5° C. for 20 minutes. Deoxycholic acid to a final conoentration of 1 mg/ml was added to the resultant suspension which was then incubated at 20° C. Deoxyribonuclease to a final concentration of 0.1 mg/ml was added, and the cells were disrupted in a polytron homogenizer. After removal of the cell debris by centrifugation at 80,000×G, 40 minutes, the lysate was subjected to column chromatography on high molecular weight, cross-linked dextran (Sephadex G-75). The fractions having elastase activity were purified by antibody affinity chromatography, and used for the following determination of elastase activity.

Elastase activity in the sample solution was determined by the following procedure. N-carbobenzoxy-L-alanine-p-nitrophenyl ester (Sigma), a sythetic substrate, was dissolved in 50 mM Tris-HCl (pH 8.0) to give a 0.1 mM solution. To 0.25 ml of this substrate solution, 0.25 ml of the elastase sample solution was added, and, after reaction for 30 minutes at 37° C., the absorbance at 410 nm was determined. The elastase activity was detected by the increase in the absorbance of 0.36. At the same time, when elastatinal or α-1-antitrypsin (an elastase inhibitor), was added to this sample solution to a final concentration of 0.1 mg/ml, it was found that the inhibitor inhibited the activity.

(8) production of human pancreatic elastase IIIB using yeast

In the case of yeast as a host (and as with a *Escherichia coli, Bacillus subtilis* or mammalian cells). human pancreatic elastase IIIB cDNA could be ligated to a suitable expression vector using known techniques, introduced into the host cells and expressed. Elastase activity in the culture medium was confirmed.

*Saccharomyces cerevisiae* described in "Japanese Guidelines for Recombinant DNA Research" may be used as host, but S288C strain and other strains are practically suitable. On the other hand, YEP13 and other vectors were appropriate as a vector. As promoter, the ADH1 gene coding for alcohol dehydrogenase gene, and other promoters, are suitable.

We claim:
1. A human elastase which comprises an amino acid sequence selected from the group consisting of human pancreatic elastase IIB, human pancreatic elastase IIIA, human pancreatic elastase IIIB, human pancreatic said amino acid sequences of human pancreatic elastase IIB, human pancreatic elastase IIIA, and human pancreatic elastase IIIB respectively being;

human pancreatic elastase IIB:

(N)-Cys Gly Val Ser Thr Tyr Ala Pro Asp Met
Ser Arg Met Leu Gly Gly Glu Glu Ala Arg
Pro Asn Ser Trp pro Trp Gln Val Ser Leu
Gln Tyr Ser Ser Asn Gly Gln Trp Tyr His
Thr Cys Gly Gly Ser Leu Ile Ala Asn Ser
Trp Val Leu Thr Ala Ala His Cys Ile Ser
Ser Ser Arg Ile Tyr Arg Val Met Leu Gly
Gln His Asn Leu Tyr Val Ala Glu Ser Gly
Ser Leu Ala Val Ser Val Ser Lys Ile Val
Val His Lys Asp Trp Asn Ser Asn Gln Val
Ser Lys Gly Asn Asp Ile Ala Leu Leu Lys
Leu Ala Asn Pro Val Ser Leu Thr Asp Lys
Ile Gln Leu Ala Cys Leu Pro Pro Ala Gly
Thr Ile Leu Pro Asn Asn Tyr Pro Cys Tyr
Val Thr Gly Trp Gly Arg Leu Gln Thr Asn
Gly Ala Leu Pro Asp Asp Leu Lys Gln Gly
Arg Leu Leu Val Val Asp Tyr Ala Thr Cys
Ser Ser Ser Gly Trp Trp Gly Ser Thr Val
Lys Thr Asn Met Ile Cys Ala Gly Gly Asp
Gly Val Ile Cys Thr Cys Tyr Asn Gly Asp Ser
Gly Gly Pro Leu Asn Cys Gln Ala Ser Asp
Gly Arg Trp Glu Val His Gly Ile Gly Ser
Leu Thr Ser Val Leu Gly Cys Asn Tyr Tyr
Tyr Lys Pro Ser Ile Phe Thr Arg Val Ser
Asn Tyr Asn Asp Trp Ile Asn Ser Val Ile
Ala Asn Asn-(C)

human pancreatic elastase IIIA:

(N)-Val Val His Gly Glu Asp Ala Val Pro Tyr
Ser Trp Pro Trp Gln Val Ser Leu Gln Tyr
Glu Lys Ser Gly Ser phe Tyr His Thr Cys
Gly Gly Ser Leu Ile Ala Pro Asp Trp Val
Val Thr Ala Gly His Cys Ile Ser Arg Asp
Leu Thr Tyr Gln Val Val Leu Gly Glu Tyr
Asn Leu Ala Val Lys Glu Gly Pro Glu Gln
Val Ile Pro Ile Asn Ser Glu Glu Leu Phe
Val His Pro Leu Trp Asn Arg Ser Cys Val
Ala Cys Gly Asn Asp Ile Ala Leu Ile Lys
Leu Ser Arg Ser Ala Gln Leu Gly Asp Ala
Val Gln Leu Ala Ser Leu Pro Pro Ala Gly
Asp Ile Leu Pro Asn Lys Thr Pro Cys Tyr
Ile Thr Gly Trp Gly Arg Leu Tyr Thr Asn
Gly Pro Leu Pro Asp Lys Leu Gln Gln Ala
Arg Leu Pro Val Val Asp Tyr Lys His Cys
Ser Arg Trp Asn Trp Trp Gly Ser Thr Val
Lys Lys Thr Met Val Cys Ala Gly Gly Tyr
Ile Arg Ser Gly Cys Asn Gly Asp Ser Gly
Gly Pro Leu Asn Cys Pro Thr Glu Asp Gly
Gly Trp Gln Val His Gly Val Thr Ser Phe
Val Ser Ala Phe Gly Cys Asn Phe Ile Trp
Lys Pro Thr Val Phe Thr Arg Val Ser Ala
Phe Ile Asp Trp Ile Glu Glu Thr Ile Ala
Ser His-(C)

or human pancreatic elastase IIIB (N)-Val Val Asn Gly Glu Asp Ala Val Pro Tyr
Ser Trp Pro Trp Gln Val Ser Leu Gln Tyr
Glu Lys Ser Gly Ser Phe Tyr His Thr Cys
Gly Gly Ser Leu Ile Ala Pro Asp Trp Val
Val Thr Ala Gly His Cys Ile Ser Ser Ser
Arg Thr Tyr Gln Val Val Leu Gly Glu Tyr
Asp Arg Ala Val Lys Glu Gly Pro Glu Gln
Val Ile Pro Ile Asn Ser Gly Asp Leu Phe
Val His Pro Leu Trp Asn Arg Ser Cys Val

```
Ala Cys Gly Asn Asp Ile Ala Leu Ile Lys
Leu Ser Arg Ser Ala Gln Leu Gly Asp Ala
Val Gln Leu Ala Ser Leu Pro Pro Ala Gly
Asp Ile Leu Pro Asn Glu Thr Pro Cys Tyr
Ile Thr Gly Trp Gly Arg Leu Tyr Thr Asn
Gly Pro Leu Pro Asp Lys Leu Gln Glu Ala
Leu Leu Pro Val Val Asp Tyr Glu His Cys
Ser Arg Trp Asn Trp Trp Gly Ser Ser Val
Lys Lys Thr Met Val Cys Ala Gly Gly Asp
Ile Arg Ser Gly Cys Asn Gly Asp Ser Gly
Gly Pro Leu Asn Cys Pro Thr Glu Asp Gly
Gly Trp Gln Val His Gly Val Thr Ser Phe
Val Ser Ala Phe Gly Cys Asn Thr Arg Arg
Lys Pro Thr Val Phe Thr Arg Val Ser Ala
Phe Ile Asp Trp Ile Glu Glu Thr Ile Ala
Ser His-(C).
```

2. The human elastase of claim 1 which comprises said human pancreatic elastase IIB amino acid sequence.

3. The human elastase of claim 1 which comprises said human elastase IIIA amino acid sequence.

4. The human elastase of claim 1 which comprises said human pancreatic elastase IIIB amino acid sequence.

* * * * *

UNITED STATES PATENT AND TRADEMARK OFFICE
CERTIFICATE OF CORRECTION

PATENT NO. : 4,985,361
DATED : January 15, 1991
INVENTOR(S) : TAKIGUCHI et al

It is certified that error appears in the above-identified patent and that said Letters Patent is hereby corrected as shown below:

Column 48, line 5:

Delete "human pancreatic" (second occurrance).

Title page, Section [56] References Cited, insert the following:

FOREIGN PATENT DOCUMENTS -

0 157 604   10/1985   EUROPE

Signed and Sealed this

First Day of June, 1993

Attest:

MICHAEL K. KIRK

*Attesting Officer*    Acting Commissioner of Patents and Trademarks